US011602606B2

(12) United States Patent
Amarasinghe et al.

(10) Patent No.: US 11,602,606 B2
(45) Date of Patent: *Mar. 14, 2023

(54) RESPIRATORY MASK

(71) Applicant: ResMed Pty Ltd, Bella Vista (AU)

(72) Inventors: Amal Shirley Amarasinghe, Sydney (AU); Angelene Marie Ozolins, Sydney (AU); Lee James Veliss, Rotterdam (NL); Alicia Kristianne Wells, Sydney (AU); Eric Siu, Strathfield (AU); Ian Fredrick Johnson, Sydney (AU); Alison Ruth Norcott, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 498 days.

This patent is subject to a terminal disclaimer.

(21) Appl. No.: 16/365,724

(22) Filed: Mar. 27, 2019

(65) Prior Publication Data
US 2019/0217040 A1 Jul. 18, 2019

Related U.S. Application Data

(63) Continuation of application No. 13/097,501, filed on Apr. 29, 2011, now Pat. No. 10,265,492.
(Continued)

(51) Int. Cl.
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0616* (2014.02);
(Continued)

(58) Field of Classification Search
CPC .............. A61M 16/06; A61M 16/0683; A61M 16/0616; A61M 16/0633; A61M 16/0816;
(Continued)

(56) References Cited

U.S. PATENT DOCUMENTS

| 4,231,675 A | 11/1980 | Scozzafava |
| 4,641,646 A * | 2/1987 | Schultz ............. A61M 16/0463 128/204.18 |

(Continued)

FOREIGN PATENT DOCUMENTS

| GB | 2 200 281 A | 8/1988 |
| WO | WO 2005/063326 A1 | 7/2005 |

(Continued)

*Primary Examiner* — Colin W Stuart
*Assistant Examiner* — Douglas Y Sul
(74) *Attorney, Agent, or Firm* — Nixon & Vanderhye P.C.

(57) ABSTRACT

A respiratory mask assembly for use with a patient, and that is suited for use with children ranging in age from about 2-7 years, includes a flexible patient interface structure arranged to interface with and deliver air to the patient's nose, the patient interface structure including cylindrical protrusions extending from respective opposite sides of the patient interface structure adjacent the patient's nares; a frame configured to support the patient interface structure, the frame including a pair of cylinders, each cylinder configured to receive a respective cylindrical protrusion of the patient interface structure; headgear arranged for releasable attachment to the frame; an air delivery tube connected to either one of the cylindrical protrusions; and a plug connected to the other one of the cylindrical protrusions.

27 Claims, 62 Drawing Sheets

Related U.S. Application Data

(60) Provisional application No. 61/330,039, filed on Apr. 30, 2010, provisional application No. 61/418,037, filed on Nov. 30, 2010.

(52) U.S. Cl.
CPC .... *A61M 16/0633* (2014.02); *A61M 16/0816* (2013.01); *A61M 16/0858* (2014.02); *A61M 2210/0618* (2013.01)

(58) Field of Classification Search
CPC .......... A61M 16/0858; A61M 16/0141; A61M 16/085; A61M 16/20; A61M 16/206; A61M 16/208; A61M 2210/0618; A61B 5/6803
See application file for complete search history.

(56) References Cited

U.S. PATENT DOCUMENTS

| | | | |
|---|---|---|---|
| 4,848,334 A | 7/1989 | Bellm | |
| 4,971,051 A | 11/1990 | Toffolon | |
| 5,471,769 A | 12/1995 | Sink | |
| 5,474,060 A * | 12/1995 | Evans | A61B 5/097 128/204.22 |
| 5,598,840 A | 2/1997 | Iund et al. | |
| 5,709,664 A | 1/1998 | Vandenbroek et al. | |
| 5,937,851 A | 8/1999 | Serowski et al. | |
| 5,951,519 A | 9/1999 | Utterberg | |
| 6,067,983 A * | 5/2000 | Stenzler | A61B 5/097 128/204.23 |
| 6,273,087 B1 * | 8/2001 | Boussignac | A61M 16/12 128/200.12 |
| 6,418,928 B1 | 7/2002 | Bordewick et al. | |
| 6,588,427 B1 | 7/2003 | Carlsen et al. | |
| 6,595,214 B1 | 7/2003 | Hecker et al. | |
| 6,631,718 B1 | 10/2003 | Lovell | |
| 7,047,972 B2 | 5/2006 | Ging et al. | |
| 7,066,178 B2 | 6/2006 | Gunaratnam et al. | |
| 7,066,179 B2 | 6/2006 | Eaton et al. | |
| 7,100,249 B2 | 9/2006 | Hurn | |
| 7,156,826 B2 | 1/2007 | Ishii et al. | |
| 7,318,437 B2 | 1/2008 | Gunaratnam et al. | |
| 7,318,439 B2 | 1/2008 | Raje et al. | |
| 7,631,643 B2 | 12/2009 | Morrison et al. | |
| 7,640,933 B1 | 1/2010 | Ho | |
| 2002/0162397 A1 * | 11/2002 | Orr | A61B 5/087 73/700 |
| 2003/0116160 A1 | 6/2003 | Kwok | |
| 2006/0042629 A1 | 3/2006 | Geist | |
| 2006/0081250 A1 | 4/2006 | Bordewick et al. | |
| 2006/0201514 A1 * | 9/2006 | Jones | A61M 16/0683 128/206.21 |
| 2007/0137653 A1 | 6/2007 | Wood | |
| 2007/0221228 A1 | 9/2007 | Ho et al. | |
| 2008/0060653 A1 | 3/2008 | Hallett et al. | |
| 2008/0178875 A1 | 7/2008 | Henry | |
| 2008/0196768 A1 * | 8/2008 | Steffan | F16L 55/1152 137/232 |
| 2008/0295846 A1 * | 12/2008 | Han | A61M 16/0858 128/207.13 |
| 2009/0044808 A1 | 2/2009 | Guney et al. | |
| 2009/0050156 A1 | 2/2009 | Ng et al. | |
| 2009/0173350 A1 * | 7/2009 | Swanson | A61M 16/085 128/207.18 |
| 2009/0202207 A1 * | 8/2009 | Grzegorzewska | H01R 13/746 385/88 |
| 2009/0299158 A1 * | 12/2009 | Boatner | A61M 16/0666 600/301 |
| 2010/0116276 A1 | 5/2010 | Bayasi | |
| 2010/0313891 A1 | 12/2010 | Veliss et al. | |
| 2011/0247616 A1 * | 10/2011 | Von Hollen | A61M 16/0816 128/203.12 |

FOREIGN PATENT DOCUMENTS

| | | |
|---|---|---|
| WO | WO 2005/086943 A2 | 9/2005 |
| WO | WO 2006/074516 A1 | 7/2006 |
| WO | WO 2007/131267 A1 | 11/2007 |
| WO | WO 2008/106716 A1 | 9/2008 |
| WO | WO-2008106716 A1 * | 9/2008 ........ A61M 16/0622 |
| WO | WO 2009/052560 A1 | 4/2009 |

* cited by examiner

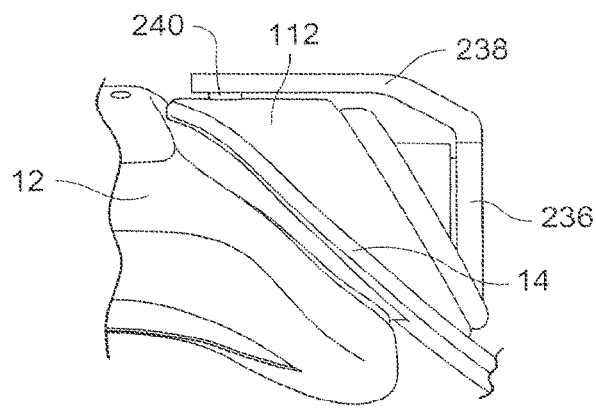
Fig. 96
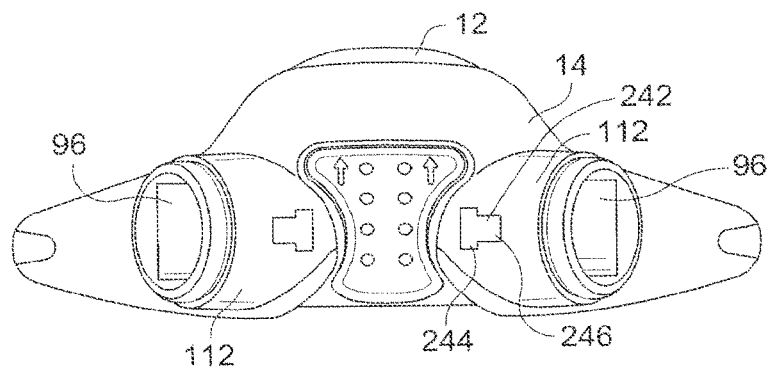
Fig. 97
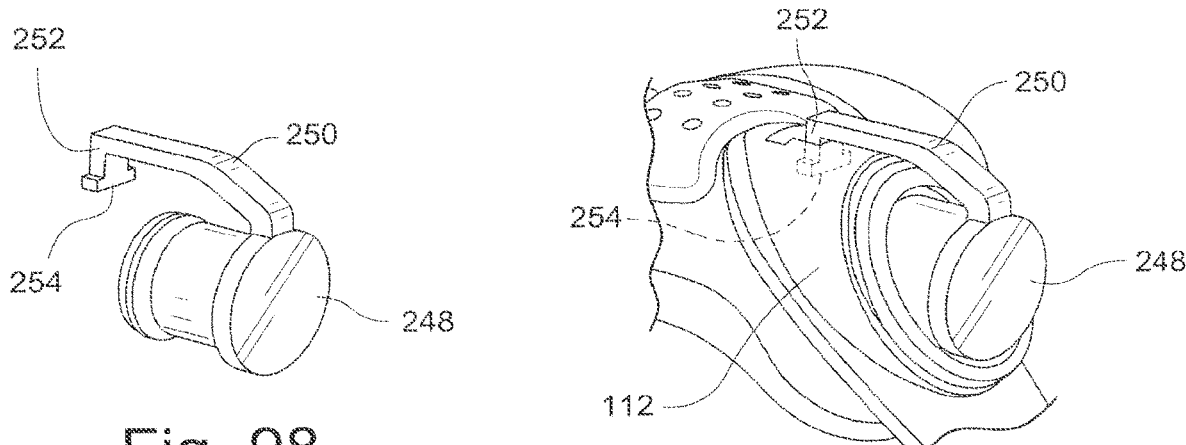
Fig. 98
Fig. 99

RESPIRATORY MASK

CROSS REFERENCE TO RELATED APPLICATIONS

This application is a continuation of U.S. application Ser. No. 13/097,501, now allowed, filed Apr. 29, 2011, which application claims the benefit of U.S. Applications 61/330,039 and 61/418,037, filed Apr. 30, 2010 and Nov. 30, 2010, respectively, the entire contents of each being incorporated herein by reference.

BACKGROUND OF THE TECHNOLOGY

Patient interfaces, such as a nasal mask assembly, for use with Continuous Positive Airway Pressure Devices (CPAP), flow generators or blowers in the treatment of sleep disordered breathing (SDB), such as Obstructive Sleep Apnea (OSA), typically include a soft-patient contacting portion, such as a cushion, and a rigid shell or frame. In use, the patient interface is held in a sealing position by headgear so as to enable a supply of air at positive pressure to be delivered to the patient's airways.

Factors in the efficacy of therapy and compliance of patients with therapy include: mask comfort; sealing; stability (e.g. aids in sealing); fit; and ease of use.

Another factor of the prior art is manufacturability.

While there are a large number of patient interfaces designed for adults, there are relatively few designed to suit infants and children. Prior art masks for treating children are deficient in several areas. For example, infants may lie on their stomachs when they sleep. The configuration of prior art masks are too large and/or bulky on the infant's face or forehead to readily allow for this. Other mask designs are too flexible and might collapse (e.g. Sullivan et al.—WO 01/32250 A1).

It is desirable for parents to have a clear view of their child when the child is wearing a mask. Some prior art masks do not allow for this (e.g. mask covers too much of child's face). It is also desirable for clinicians and caregivers to have a clear view of the nares to ensure that they are not obstructed.

Some prior art masks include hard/rigid components. This may cause pressure sores and can be perceived negatively by patients/clinicians/parents.

Prior art masks designed for adults are also generally not designed to be fitted by a third party (e.g. clips are difficult to operate), such as would be useful in a mask for a child or infant.

SUMMARY OF THE TECHNOLOGY

An aspect of the present technology relates to a respiratory mask assembly designed to suit infants and children.

Another aspect of the present technology relates to a respiratory mask assembly in which an air delivery tube is connectable to either a right side or a left side of the mask assembly.

Another aspect of the present technology relates to a respiratory mask assembly in which an air delivery tube is connectable to either a right side or a left side of the mask assembly, and a plug is connectable to the other side of the mask assembly opposite from the air delivery tube.

Another aspect of the present technology relates to a respiratory mask assembly that includes a patient interface (e.g., flexible) and a frame (e.g., rigid) adapted to receive and support the patient interface, where at least one of the patient interface and the frame includes at least one orientation element adapted to indicate a correct orientation between a patient interface and the frame.

Another aspect of the present technology relates to a respiratory mask assembly that includes a patient interface structure (e.g., flexible) arranged to interface with and deliver air to a patient, the patient interface having one or more protrusions (e.g., cylindrical), extending from respective opposite sides of the patient interface structure adjacent the patient's nares, and a frame configured to support the patient interface structure, the frame including one or more receiving members, e.g., cylinders, each receiving member configured to receive a respective protrusion of the patient interface structure.

Another aspect of the present technology relates to a respiratory mask assembly that includes a patient interface, (e.g., flexible) arranged to interface with a deliver air to patient, and a frame configured to support the patient interface, where the patient interface is generally trapezoidally shaped with one or more protrusions (e.g., cylindrical) extending from each side of the patient interface.

Another aspect of the present technology relates to a respiratory mask assembly that includes a patient interface (e.g., flexible) arranged to interface with an deliver air to a patient, the patient interface having one or more protrusions (e.g., cylindrical) extending from respective opposite sides of the patient interface adjacent the patient's nares, and a frame configured to support the patient interface, where each of the protrusions comprises an inner protrusion and an outer protrusion (e.g., cylindrical).

Another aspect of the present technology relates to a respiratory mask assembly that includes a patient interface (e.g., flexible) arranged to interface with and deliver air to a patient, the patient interface having one or more protrusions (e.g., cylindrical) extending from respective opposite sides of the patient interface adjacent the patient's nares, a frame configured to support the patient interface and an air delivery tube connected to either one of the protrusions, where at least one said protrusion decouples movement of the air delivery tube from the patient interface and/or from the frame.

Another aspect of the present technology relates to a respiratory mask assembly that includes a patient interface structure arranged to interface with and deliver air to a patient, the patient interface having one or more protrusions extending from respective opposite sides of the patient interface structure adjacent the patient's nares, a frame configured to support the patient interface structure, a plug adapted to be sealingly connectable to one of the protrusions, and a post extending from the frame adapted to receive and retain the plug when the plug is removed from the respective protrusion.

Another aspect of the present technology relates to a respiratory mask assembly for use with a patient and that is particularly suited for use with children, e.g. for treatment of SDB, such as obstructive sleep apnea (OSA), or congenital abnormalities. The respiratory mask assembly may include a cushion arranged to interface with and deliver air to the patient's nose. The cushion may have a tube connection portion at one or both sides adjacent the patient's nares, the tube connection portion being arranged to connect to an air delivery tube. This location also reduces destabilising moments produced by tube drag forces. A more rigid support structure adjacent the cushion may be provided to stabilize the cushion and prevent it from collapsing. Headgear may also be provided and arranged for releasable attachment to the support structure.

Another aspect of the present technology provides a respiratory mask for use with a patient including a cushion arranged to interface with and deliver air to the patient's nose, a support structure adjacent the cushion, and headgear arranged for releasable attachment to the support structure. The support structure extends over the patient's nasal bridge but not over the apex of the patient's nose, such that the support structure substantially stops the cushion from collapsing when a force is applied to a front side of the mask. This allows a patient to sleep on their face and still receive effective respiratory treatment.

Another aspect of the present technology is that the cushion may be translucent to the extent that the patient's nares can be inspected through the cushion, or the cushion may be substantially transparent (e.g., water clear).

Another aspect of the present technology is that the cushion can seal across the nose bridge at any point along its length (i.e. from the top of the nose bridge to the nose tip) so that the cushion can seal on a variety of different size noses. This is desirable as the size of a child's nose can differ depending on their age.

Another aspect of the present technology relates to a patient interface system for delivering breathable gas to a patient comprising a patient interface structure arranged to interface with and deliver air to the patient's nose, the patient interface structure comprising one or more protrusions extending from respective opposite sides of the patient interface structure adjacent the patient's nares; a frame configured to support the patient interface structure, the frame comprising one or more protrusion, each protrusion having an inner surface configured to receive a respective protrusion of the patient interface structure; headgear arranged for releasable attachment to the frame; and an air delivery tube connected to either one of the protrusions.

Another aspect of the present technology relates to a patient interface system for delivering breathable gas to a patient comprising a patient interface structure arranged to interface with and deliver air to a nose of the patient in use, the patient interface structure having a generally polygonal shape, e.g., trapezoidal shape, with one or more protrusions extending from respective opposite sides of the patient interface structure, a frame configured to support the patient interface structure, the frame comprising one or more receiving members, (e.g., cylinders) each configured to receive a respective cylindrical protrusion of the patient interface structure, headgear arranged for releasable attachment to the frame, and an air delivery tube connected to either one of the cylindrical protrusions.

Another aspect of the present technology relates to a patient interface system for delivering breathable gas to a patient comprising a flexible patient interface structure arranged to interface with and deliver air to a nose of the patient in use, the patient interface structure having one or more protrusions extending from respective opposite sides of the patient interface structure, each said cylindrical protrusion having an inner protrusion and an outer protrusion, and the patient interface structure having a thickened portion with an exhalation vent, a frame configured to support he patient interface structure, the frame configured to receive the one or more protrusions of the patient interface structure, the frame including an aperture adapted to receive the thickened portion of the flexible patient interface structure, headgear arranged for releasable attachment to the frame, and an air delivery tube connected to at least one of the cylindrical protrusions, wherein the thickened portion of the flexible patient interface structure is shaped to conform to the shape of the aperture of the frame so that the flexible patient interface structure is correctly assembled to the frame, e.g., when the aperture of the frame receives the thickened portion of the flexible patient interface structure.

According to another aspect of the present technology a plug or cap may be provided to one or more protrusions. The plug may be tethered to the frame or patient interface structure. The tether may be separately or integrally formed with the respiratory mask assembly. Alternatively, or additionally, a valve may be provided to one or several cylindrical protrusions. The valve may be integrally formed with the patient interface structure. The valve may be provided in the cap or plug. The plug may be connected to the patient interface structure, for example by a living hinge. Alternatively, the plug or cap with the valve may be permanently, or removably, snapped into the frame.

According to another aspect of the present technology, an exhalation vent may be provided to the patient interface. The exhalation vent may comprise at least one aperture, or at least one array of apertures. The exhalation vent may be disposed on a thickened portion of the patient interface. The exhalation vent may be disposed on an elbow, frame or plug portion of the mask system, According to another aspect of the present technology, one or more protrusion and/or a plug may include at least one element adapted to retain the plug in the respective protrusion.

According to another aspect of the present technology, one ore more protrusions and/or an elbow may include at least one element adapted to retain the elbow in the respective cylindrical protrusion.

According to another aspect of the present technology, a headgear is provided that may be adjustable from the front or towards the face of the patient to enable easier adjustment of the headgear when it is being worn by a child.

According to another aspect of the present technology is a quick release buckle to allow a caregiver to fit the headgear as well as remove the headgear quickly in an emergency.

Other aspects, features, and advantages of this invention will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of the technology. In such drawings:

FIG. 96 schematically depicts a partial side view of a mask assembly illustrating connection of a tether between a frame and a plug according to another sample embodiment of the technology;

FIG. 97 schematically depicts a front view of a mask assembly illustrating an aperture for connection of a tether between a frame and a plug according to another sample embodiment of the technology;

FIG. 98 schematically depicts a perspective view illustrating connection of a tether to a plug according to another sample embodiment of the technology;

FIG. 99 schematically depicts a partial perspective view of a mask assembly illustrating connection of the tether and plug of FIG. 98 to a frame;

DETAILED DESCRIPTION

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

It should be noted that the terms "mask" and "mask assembly" and the term "patient interface system" are used interchangeably in this specification. It should also be appreciated that the terms "cushion" and "patient interface structure" are used interchangeably in this specification. It should further be appreciated that the terms "headgear" and "patient interface positioning and support system" are used interchangeably in this specification.

An air delivery tube, for interconnection between a Continuous Positive Airway Pressure Device and a Patient Interface, may have an internal diameter of between 4 mm and 15 mm Preferably, the air delivery tube may have an internal diameter of between 4 mm and 10 mm Preferably, the air delivery tube may have an internal diameter of between 4 mm and 8 mm One benefit of this sample embodiment is that it reduces the weight and/or bulk of the tube and the friction that results from movement of the tube across a surface and therefore reduces the pull (i.e., "tube drag") on the patient interface.

The present technology relates to a respiratory system that has been designed for pediatric use (i.e. with infants or children) although aspects of the system may be used advantageously by adults. The respiratory system comprises a mask and a blower (e.g. a flow generator, a Continuous Positive Airway Pressure (CPAP), or a Variable Positive Airway Pressure Device (VPAP) device) and an air delivery tubing arrangement connecting the two.

1. Respiratory Mask Assembly

Figure 1:
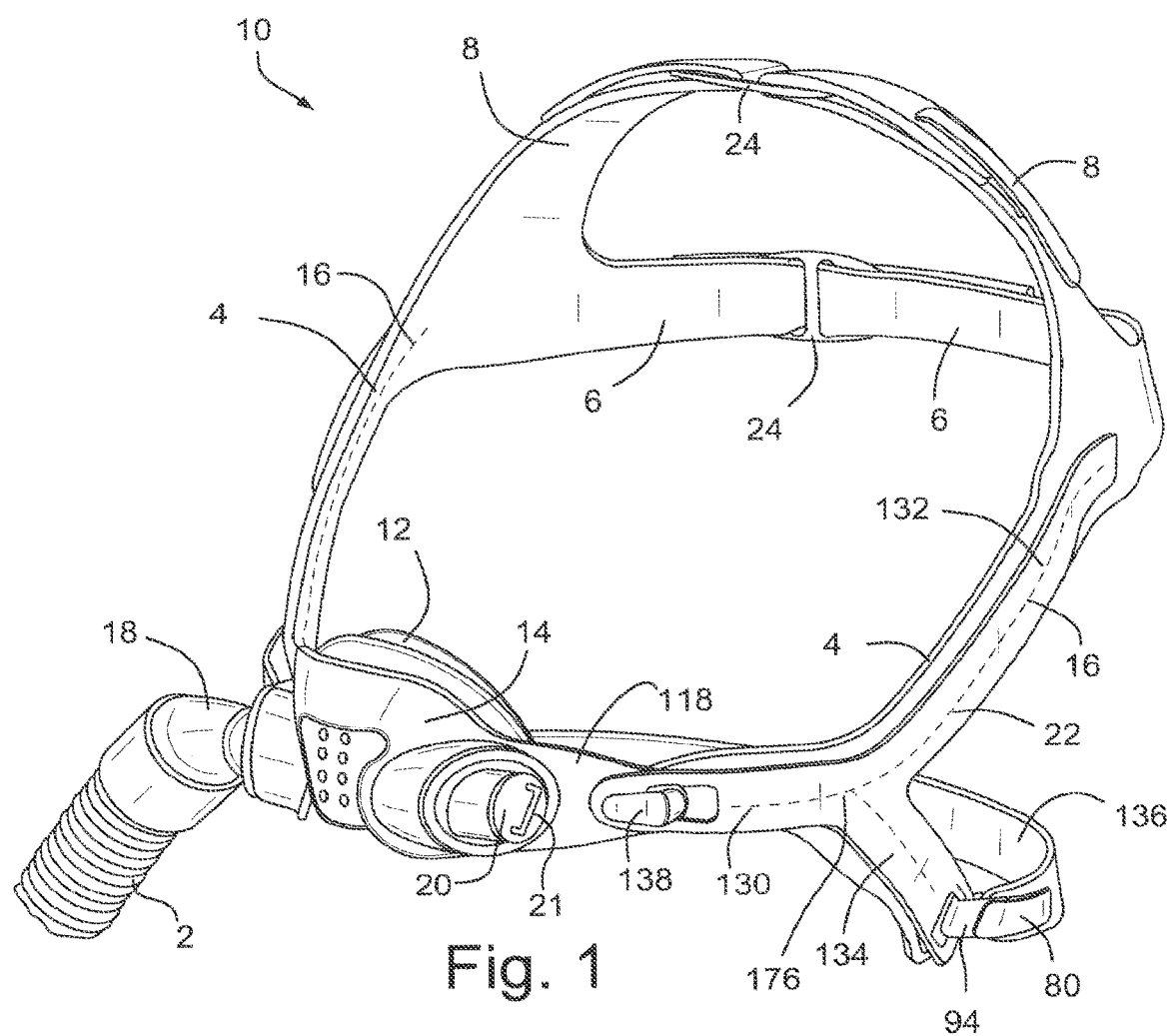
FIG. 1 schematically depicts a front perspective view of a respiratory mask assembly according to a first embodiment of the technology.

Referring to FIG. 1, a respiratory mask assembly 10 comprises a support structure, or frame, 14 which supports a patient interface structure, or cushion, 12 configured to sealingly engage the face of the patient. A tube, or hose, or conduit 2 is connected to the cushion 12 by an elbow 18 for delivering a flow of breathable gas to the patient. A patient interface positioning and support system, or headgear, 16 is configured to position and support the cushion 12 in sealing engagement with the face of the patient.

The tube 2 is connected to the cushion 12 at a side portion of the cushion by the elbow 18. The opposite side portion of the cushion 12 is provided with a plug, or cap 20 that seals the opening in the left side of the cushion 12 or provides a port to receive an oxygen tube for example. It should be appreciated that the configuration shown in FIG. 1 may be changed so that the tubes 2 is connected to the side portion of the cushion 12 by the elbow 18 and the opposite side portion of the cushion 12 may be sealed by the plug 20. The plug 20 may have a handle 21 that is adapted to be gripped by a user, to be pulled out of or pressed into the cushion 12.

1.1 Headgear

The headgear 16 may comprise side straps 4 that are configured to extend along the sides of the face of the patient in use. The side straps 4 may be configured to extend or be positioned between the patient's eyes and ears in use. The ends of the side straps 4 are connected by a rear, or back, or middle strap 6 and top straps 8. The top straps 8 may be configured to extend from a first lateral side to a second lateral side of the patient's head, and extend over the top of the patient's head to engage a crown of the patient's head in use. The rear straps 6 may be configured to extend around a back of the patient's head in use. A lower rear strap 136 may be connected to the side straps 4. The lower rear strap 136 may be configured to extend around a back of the neck of the patient in use.

The rear straps 6 and the top straps 8 may each be adjusted by a buckle 24. A buckle suitable for use to adjust the lengths of the rear straps 6 and the top straps 8 is disclosed, for example, in U.S. Patent Application Publication 2009/0044808 A1, the entire contents of which are hereby incorporated by reference.

The side straps 4 of the headgear 16 may be provided with rigidizers, yokes, or reinforcing and/or stiffening structures 22, which are configured to reinforce and/or provide a degree of rigidity to the side straps 4. The reinforcing structures 22 may include a forward finger or extension 130, each connected to a wing portion 118 of the frame 14, an upper finger or extension 132, and a lower finger or extension 134. The lower fingers 134 of the reinforcing structures 22 may be connected by the lower rear strap 136 of the headgear 16. The reinforcing structures 22 may be formed of, for example, nylon, polypropylene, polyurethane or other flexible material and have a thickness of, for example, about 0.9 mm to 1.1 mm, for example about 1.0 mm. The forward fingers 130 may have a thickness of, for example, about 1.4 mm to 1.6 mm, for example about 1.5 mm.

The straps 4, 6, 8, 136 may be formed of soft, flexible material, for example a fabric laminate. The straps 4, 6, 8, 136 may have a plurality of layers, for example a composite of a plurality of layers of different materials. The ends of the straps 4, 6, 8, 136 may include hook material that allows the ends of the straps to be fastened to a loop material on a surface of the strap.

The reinforcing structures 22 may be attached to the straps 4 by, for example, stitching 176, as shown in FIG. 1. The stitching 176 may not extend the entire length of the reinforcing structures 22 so that ends of the reinforcing structures 22 may diverge from the straps. The reinforcing structures 22 may also be attached to the straps by, for example, adhesive, or placed in a pocket formed in the straps. The reinforcing structures may also be provided as part of a composite laminate with the reinforcing structure placed between two layers of soft, flexible strap material.

The ends of the straps may have hooks to engage the loop material of the strap material. The hooks may be provided at the end of the straps of the headgear to prevent patients under the age of, for example, four years old from peeling the attached ends of the strap away and loosening the straps and/or headgear.

Referring to FIG. 1, the headgear is configured such that the buckles 24 are positioned away from the sensitive area of the patient's face. The sensitive area of the patient's face is the area generally including the mouth, the nose, and the eyes. The buckles 24 may be adjusted for a young patient by a caregiver, parent or clinician by adjusting the ends of the rear straps 6 and the top straps 8 in a direction away from the sensitive area of the patient's face. According to one method of fitting the respiratory mask assembly 10 on the patient, the top straps 8 and the rear straps 6 are adjusted through the buckles 24 to an increased length. Then an end of the lower rear strap 136 is released from connection with the headgear, e.g. released from connection with a reinforcing structure 22. The mask assembly is then placed over the patient's head until the top straps 8 and the rear straps 6 engage the patient's head and the cushion generally covers/engages the patient's nose. The end of the lower rear strap 136 is then reconnected to, for example, the reinforcing structure 22. The lower rear strap 136, the rear straps 6, and the upper straps 8 are then adjusted to provide a comfortable fit with the cushion 12 in sealing engagement with the patient's face. The configuration of the respiratory mask assembly allows a caregiver, clinician or parent to don the mask and the headgear on the child while facing the child, in that the headgear adjustment points are conveniently arranged and adjustable as the parent or clinician is face-to-face with the child patient.

1.1.1 Quick Release Buckle

Figure 17:
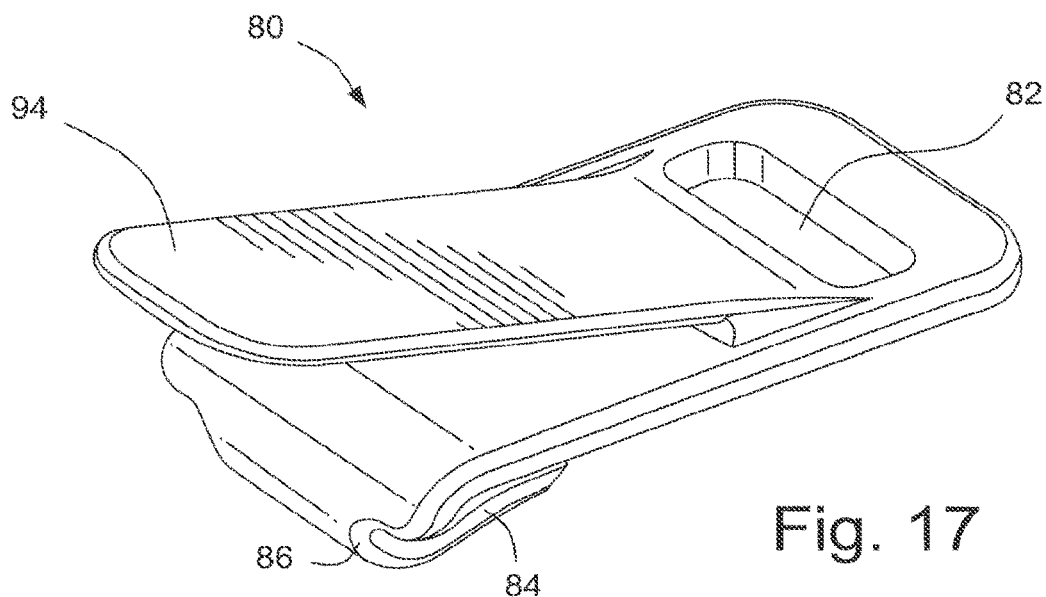
Figure 18:
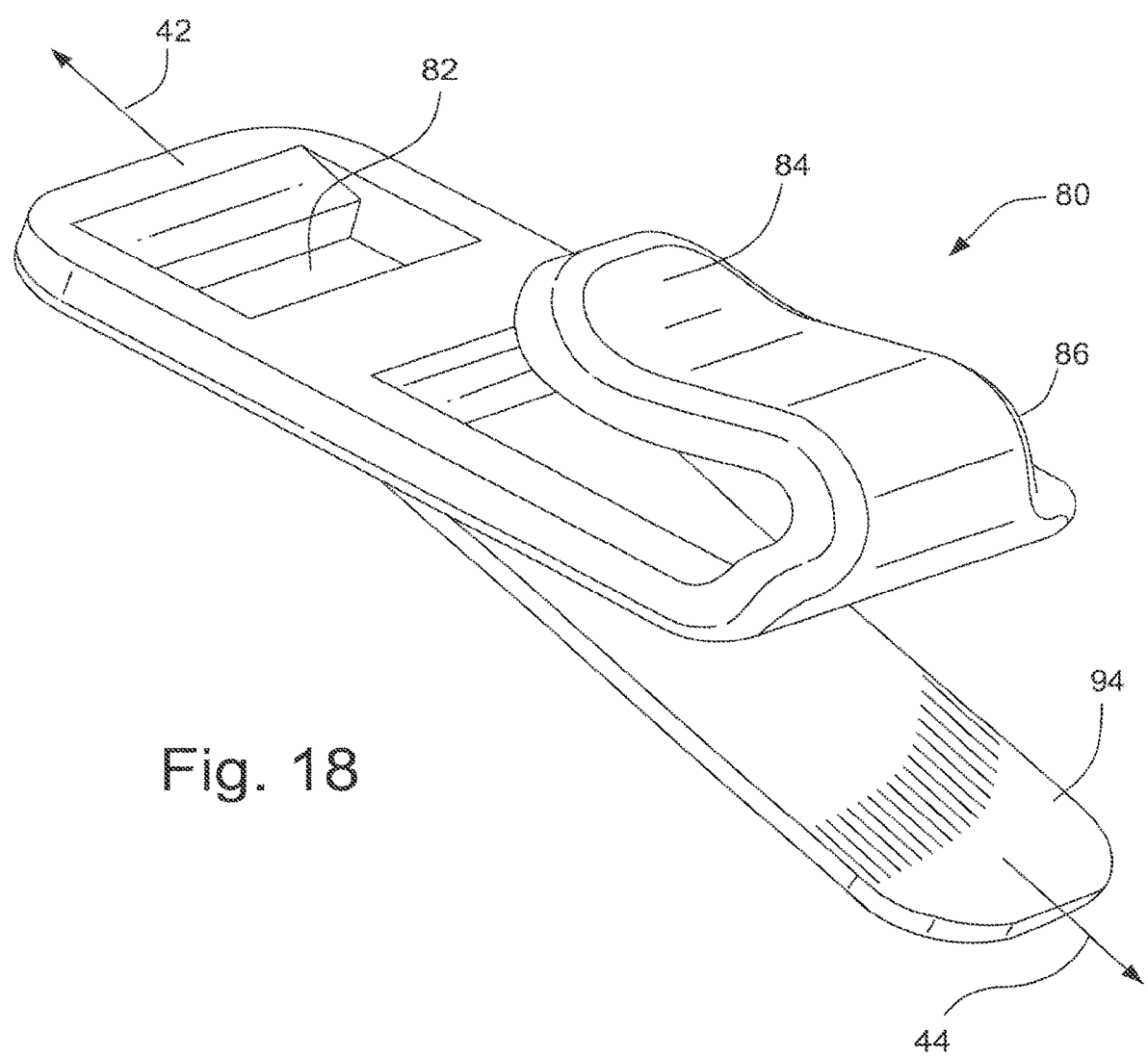
Figure 19:
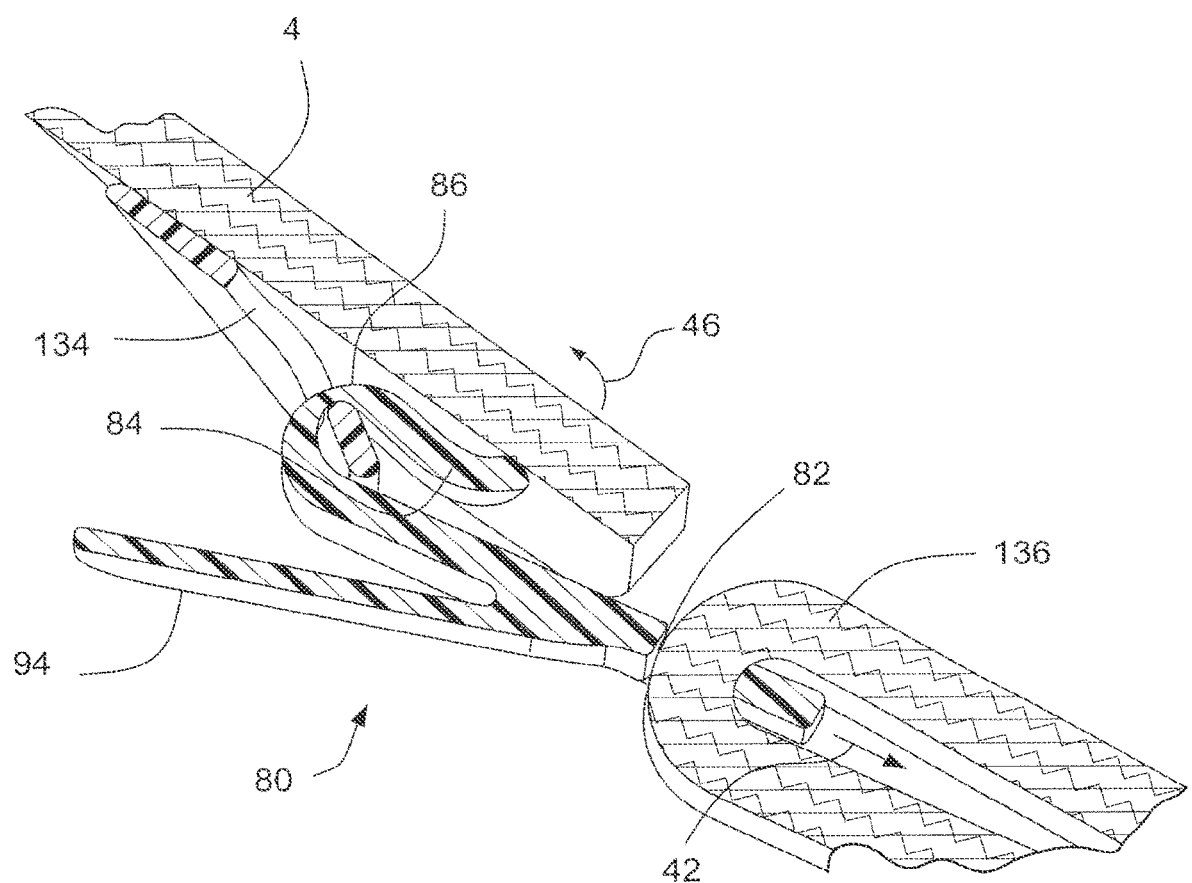
FIG. 19 schematically depict a connection of straps of a patient interface positioning and support structure, or headgear, by the quick release buckle of FIGS. 16-18.

Referring to FIGS. 16-19, a quick release buckle 80 may provide a quick and easy way to attach or remove the respiratory mask assembly 10. As shown in FIGS. 17 and 18, the quick release buckle 80 may comprise a slot 82 configured to accept a strap of the headgear, for example, as shown in FIG. 19. The other end of the quick release buckle 80 may include a hook 84 that is connected to the quick release buckle 80 by section 86. A tab 94 is provided for the user or another such as a caregiver, a parent, a clinician, etc., to grasp the quick release buckle 80 to attach or remove the respiratory mask assembly 10 from the patient.

As shown in FIG. 19, the quick release buckle 80 may connect, for example, the lower rear strap 136 to the lower finger 134 of the reinforcing structure 22. The lower rear strap 136 may be received through the slot 82 of the quick release buckle 80. As shown in FIG. 18, a pulling force 44 applied to the tab 94, for example by the caregiver or clinician, will permit the hook 84 of the quick release buckle 80 to be separated from the reinforcing structure 22. The tab 94 is connected to the reinforcing structure 22 via hook 84. Tab 94 may be adapted so as to be engageable by the fingers of the caregiver, patient or clinician, but not to interfere with the face of the patient. Tab 94 may have a gripping region that may for example include ribs or bumps to make it easier to grab the tab.

The quick release buckle 80 may also be adapted to function as an emergency latch, where the user or another such as a caregiver, a parent, a clinician, etc., may pull on the lower rear strap 136 to cause the hook 84 of the quick release buckle 80 to be separated from the reinforcing structure 22. Tension 42 on the lower rear strap 136 will cause the hook 84 of the quick release buckle 80 to flex or bend as shown by arrow 46 sufficiently to release the hook 84 from the reinforcing structure 22.

1.2 Support Structure/Frame

Figure 2A:
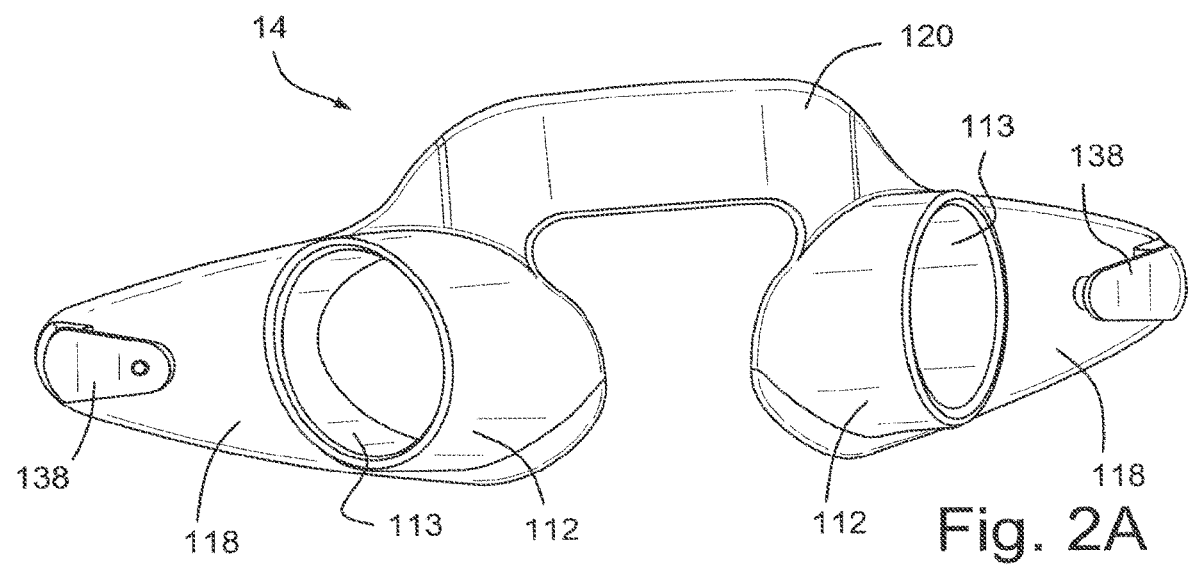
FIGS. 2A-2C schematically depict a support structure, or frame, of the respiratory mask assembly of FIG. 1.
Figure 2B:
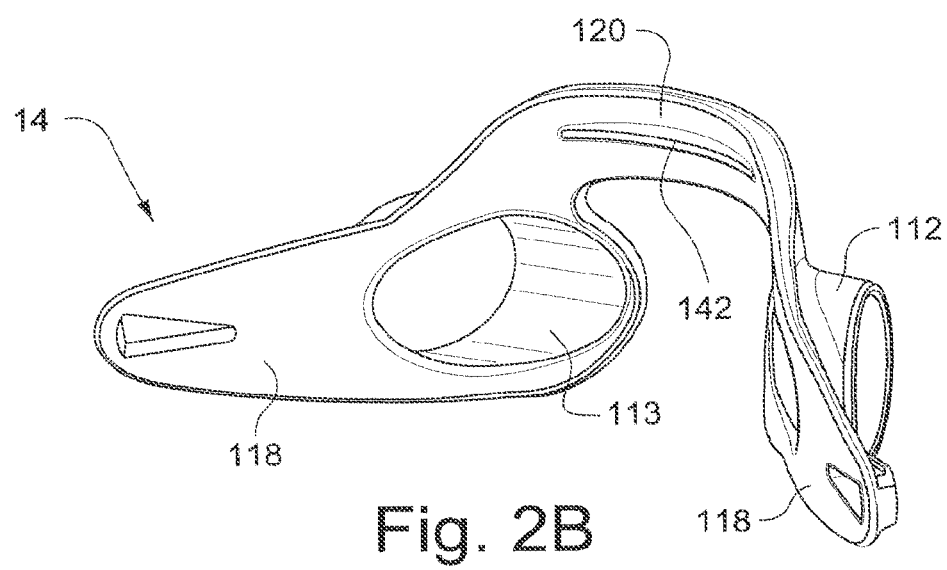
Figure 2C:
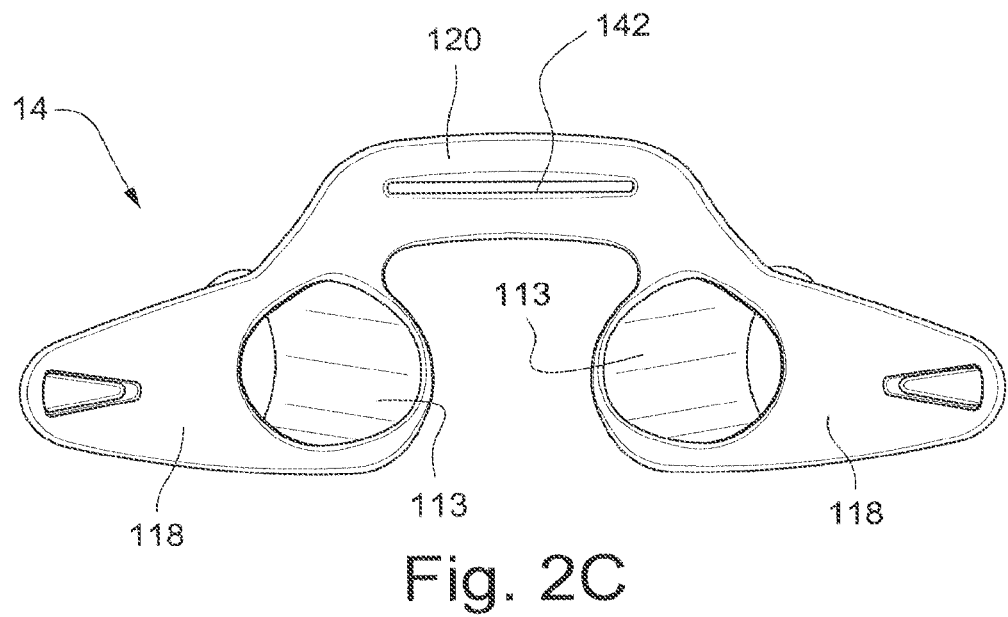

Referring to FIGS. 2A-2C, the support structure, or frame, 14 of the respiratory mask assembly 10 may be formed of a resilient material. The frame 14 comprises cylinders 112 which receive cylindrical portions of the cushion 12 as will be described in more detail below. The cylinders 112 are connected by abridge 120 which is configured to extend across the nose of the patient in use. The wing portions 118 of the frame 14 comprise connectors 138 that are configured to connect the frame 14 to the headgear 16. Suitable connectors 138 for the frame 14 are disclosed in, for example, International Application PCT/AU2008/001557 (WO 2009/052560 A1), the entire contents of which are incorporated herein by reference.

Each of the cylinders 112 includes an inner circumferential surface 113. The inner circumferential surface 113 is configured to receive the outer cylinder 98 of the cushion 12. In this way, the cylinders 112 of the frame 14 receive within them the cylindrical protrusions, including the outer cylinder 98, and thus provide support to the cushion 12.

1.2.1 Reinforcing Rib

The rear side of the bridge 120, i.e. the side facing the patient in use, may include a reinforcing rib 142 that stiffens, or reduces the flexibility of the bridge 120. The reinforcing rib 142 may prevent excessive pressure from being applied to the face of the patient in the event the headgear is over tightened. It should be appreciated that the reinforcing rib 142 may be provided on the front side of the frame 14 instead of, or in addition to, being placed on the rear side.

1.2.2 Cross Bar

Figure 21:
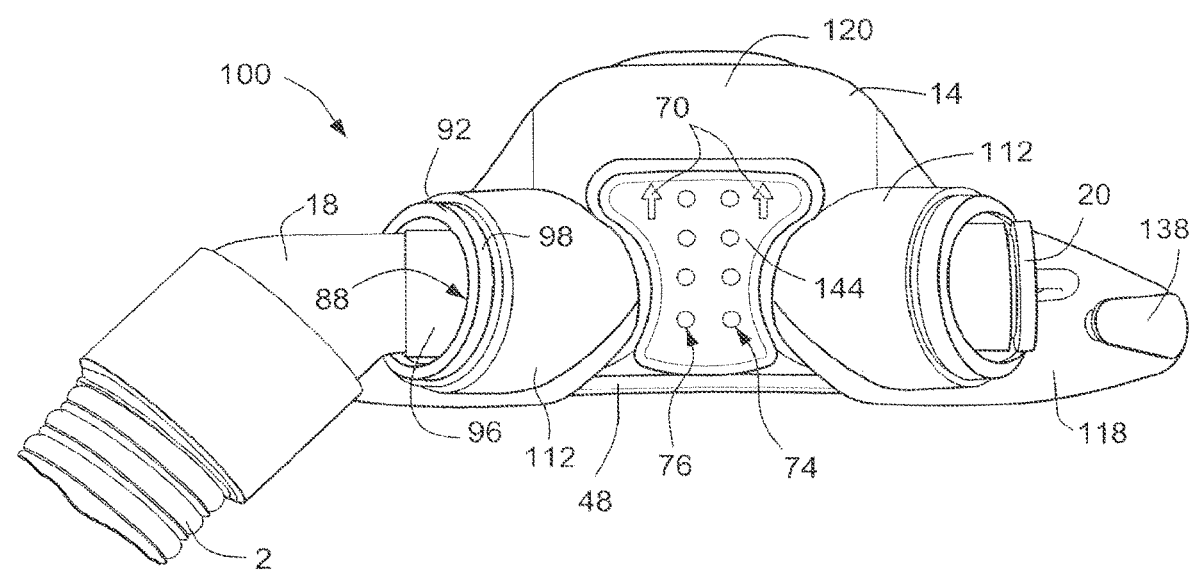
Figure 22:
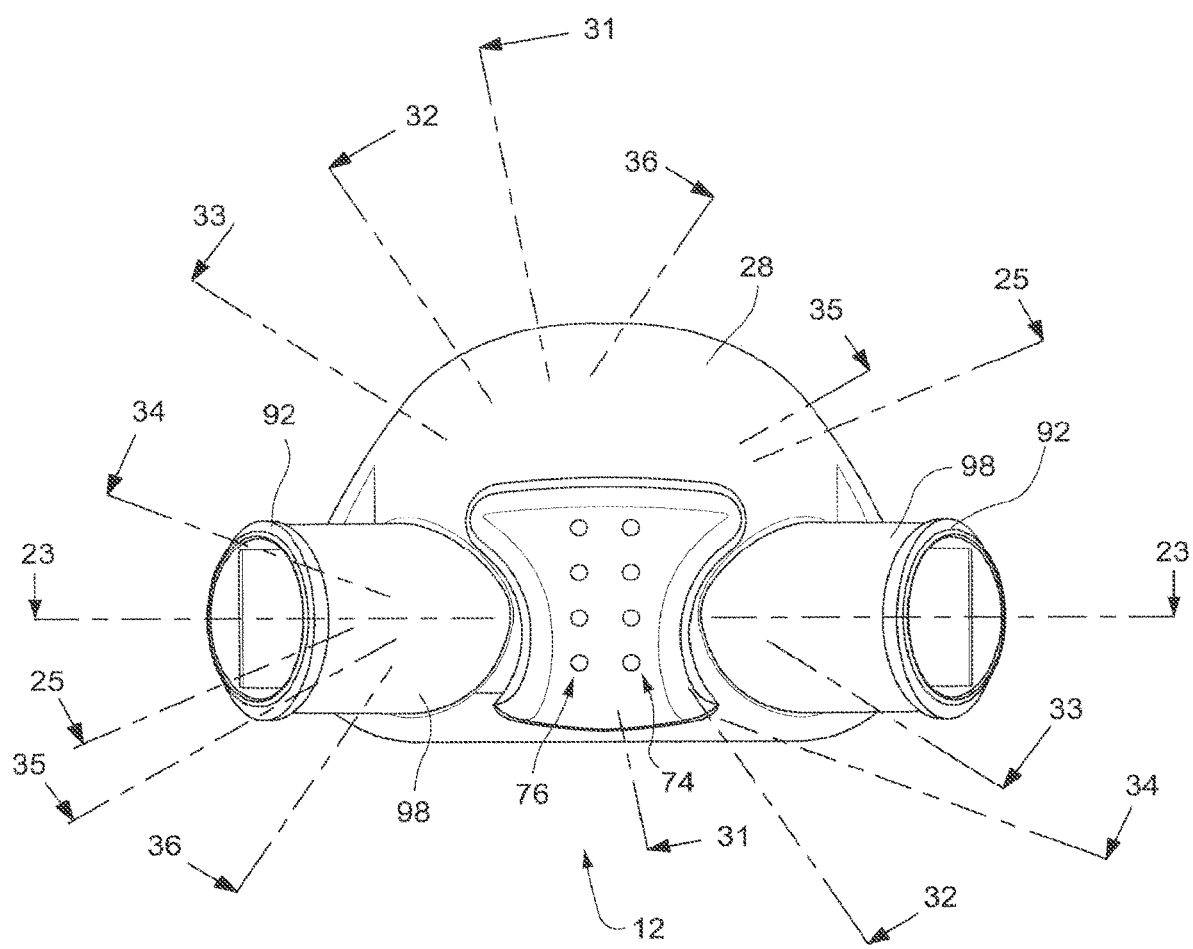
FIG. 22 schematically depicts a front view of a cushion, or patient interface structure, according to an embodiment of the technology.
Figure 23:
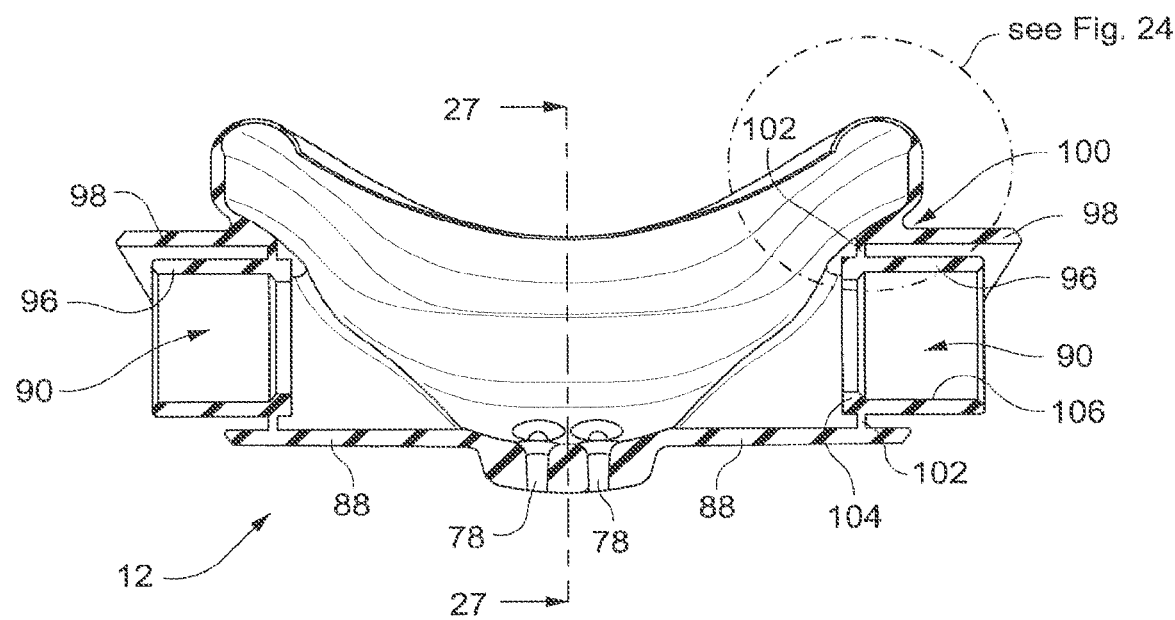
FIG. 23 schematically depicts a cross-sectional view of the cushion of FIG. 22 along line 23-23.
Figure 24:
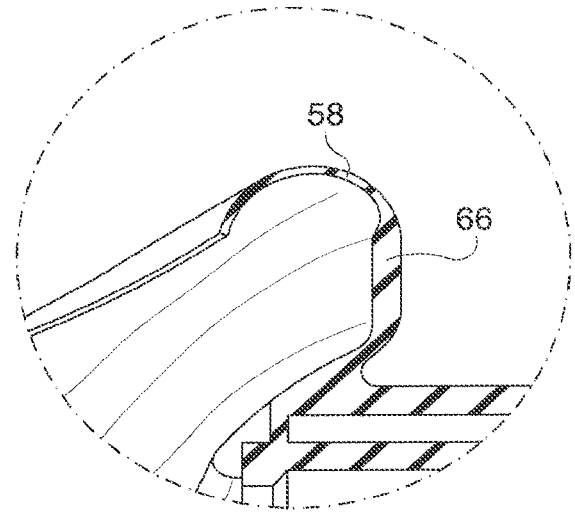
FIG. 24 schematically depicts a detailed cross-sectional view of side portions of the base wall and membrane of the section of FIG. 23.
Figure 25:
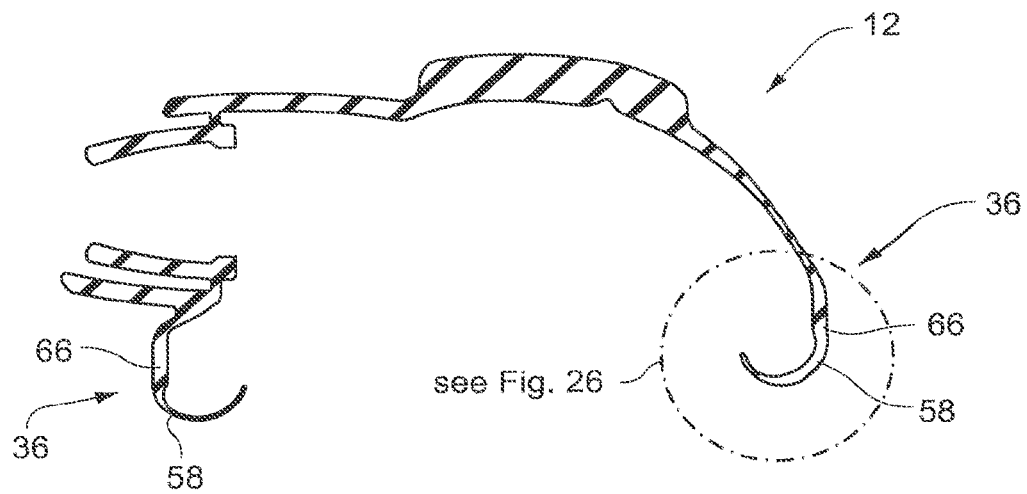
FIG. 25 schematically depicts a cross-sectional view of the cushion of FIG. 22 along line 25-25.
Figure 26:
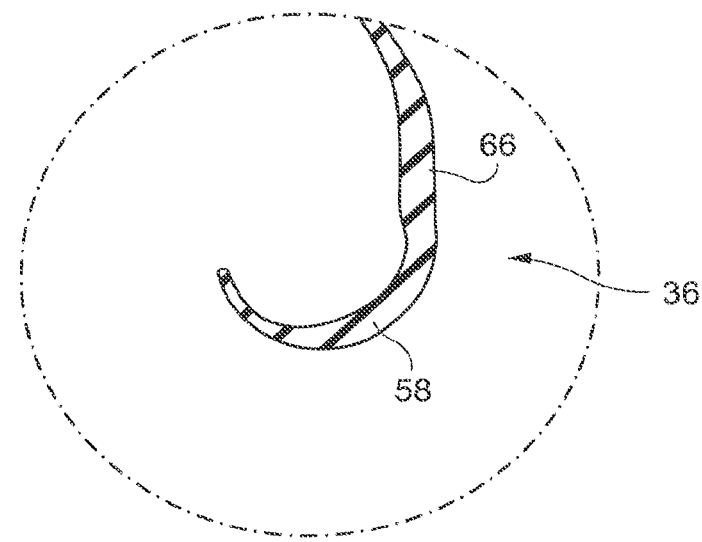
FIG. 26 schematically depicts a detailed cross-sectional view of side portions of the base wall and membrane of the section of FIG. 25.
Figure 27:
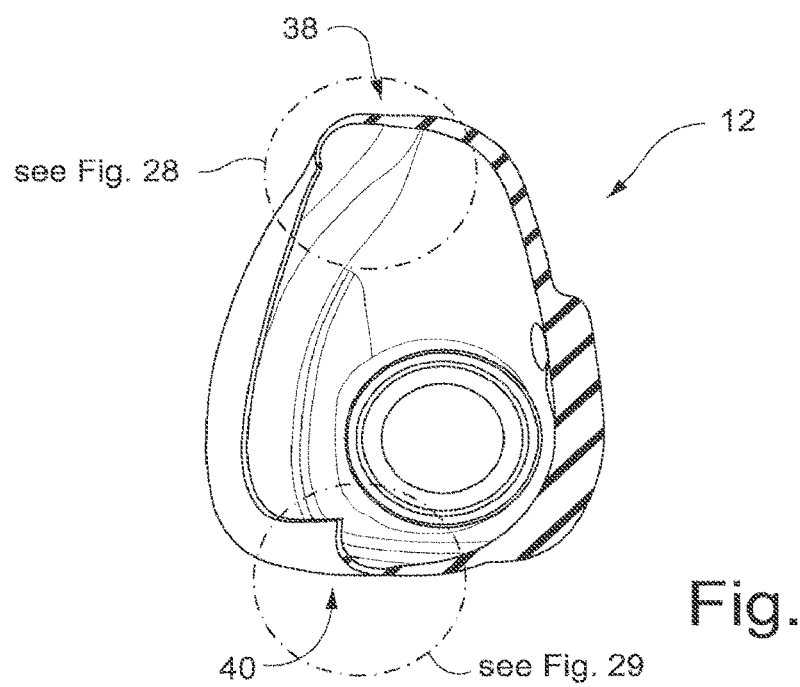
FIG. 27 schematically depicts a cross-sectional view of the cushion of FIG. 22 along line 27-27.
Figure 28:
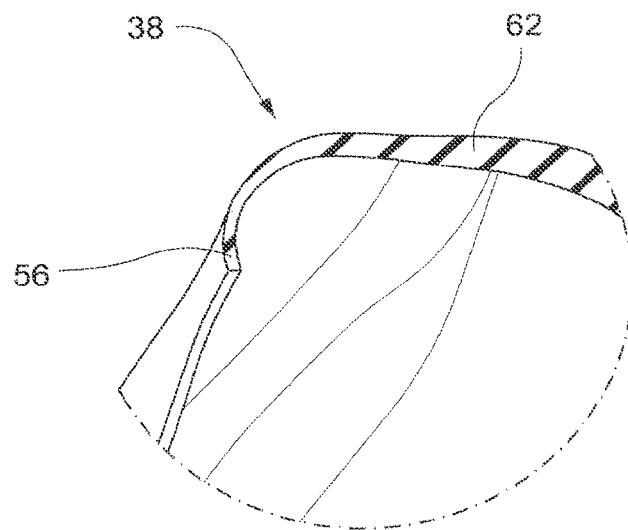
FIG. 28 schematically depicts a detailed cross-sectional view of the top portion of the base wall and membrane of the section of FIG. 27.
Figure 29:
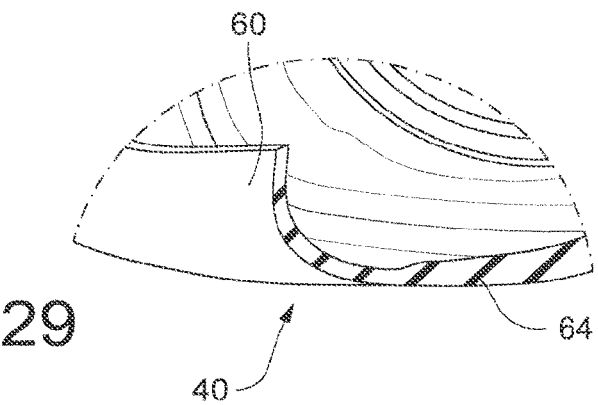
FIG. 29 schematically depicts a detailed cross-sectional view of the bottom portion of the base wall and membrane of the section of FIG. 27.
Figure 30:
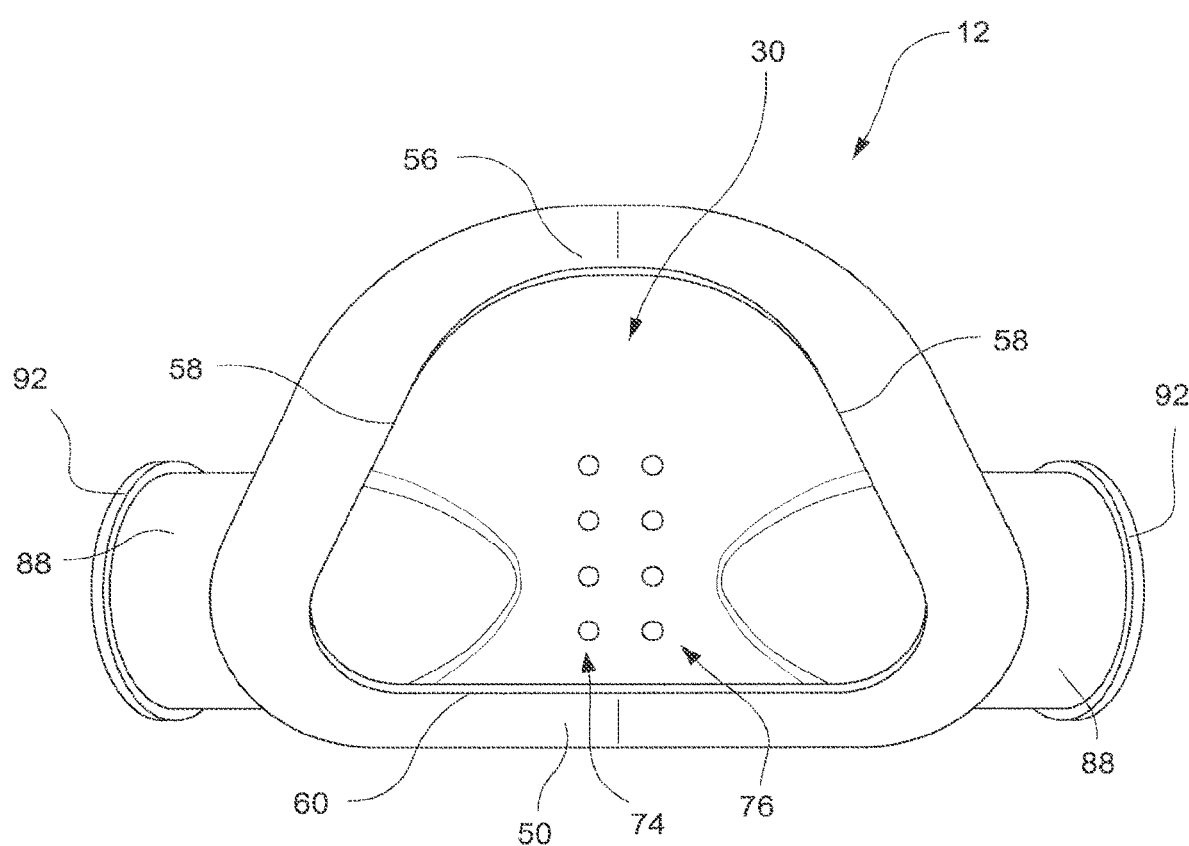
FIG. 30 schematically depicts a rear view of the cushion of FIG. 22.
Figure 31:
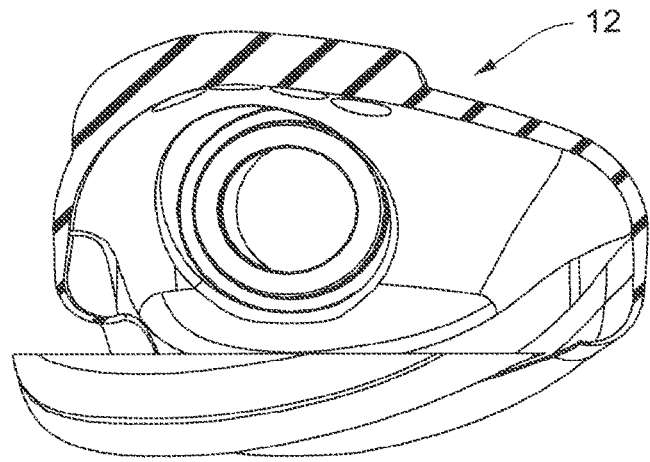
FIG. 31 schematically depicts a cross-sectional view of the cushion of FIG. 22 along line 31-31.
Figure 32:
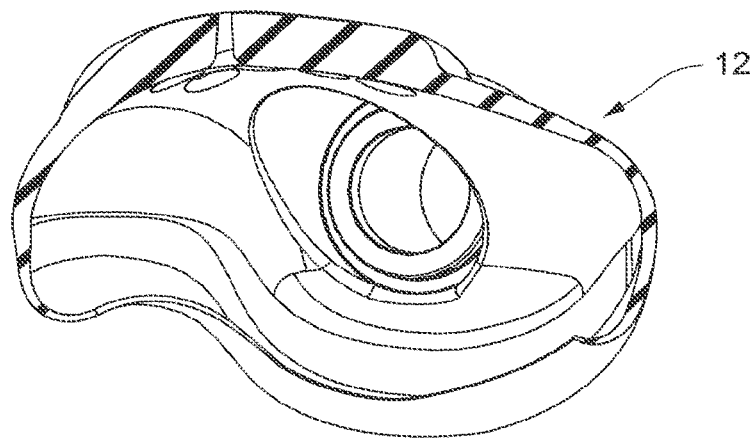
FIG. 32 schematically depicts a cross-sectional view of the cushion of FIG. 22 along line 32-32.
Figure 33:
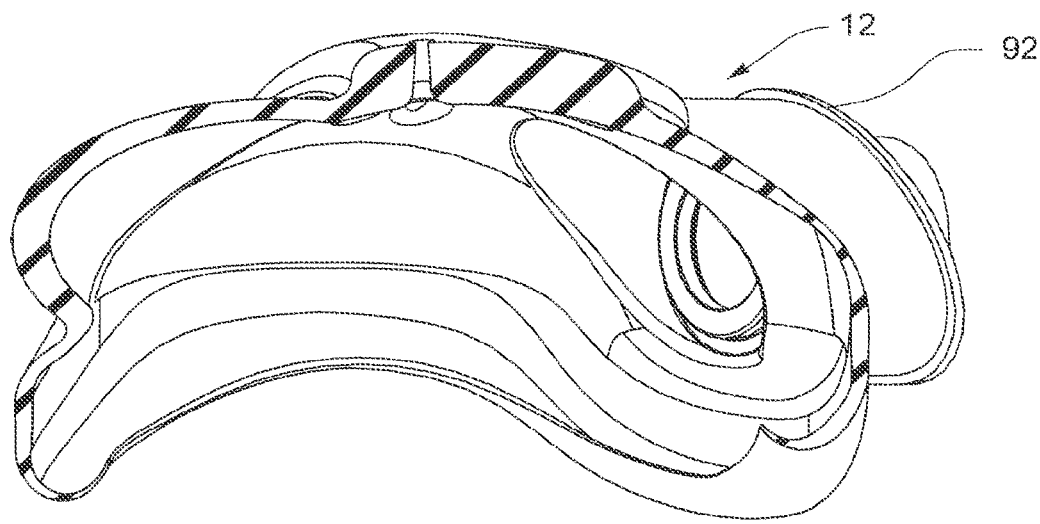
FIG. 33 schematically depicts a cross-sectional view of the cushion of FIG. 22 along line 33-33.
Figure 34:
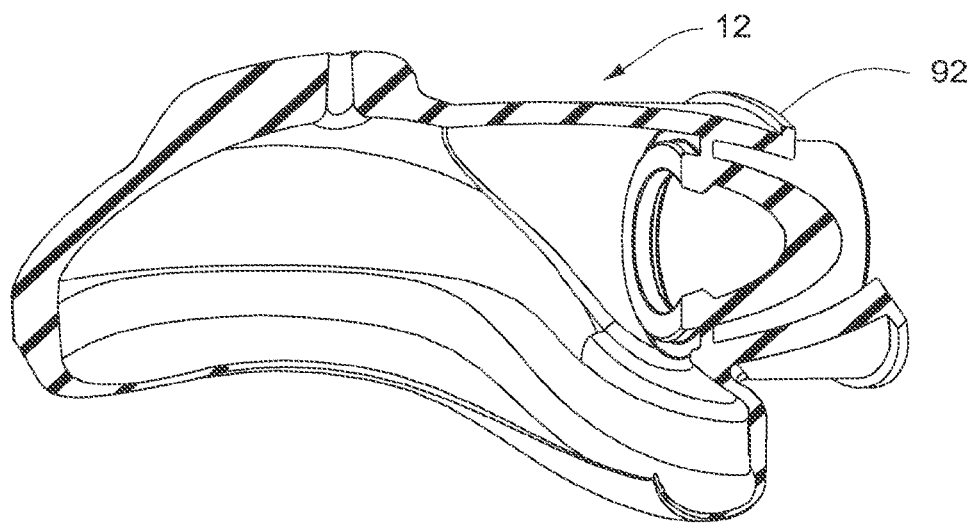
FIG. 34 schematically depicts a cross-sectional view of the cushion of FIG. 22 along line 34-34.
Figure 35:
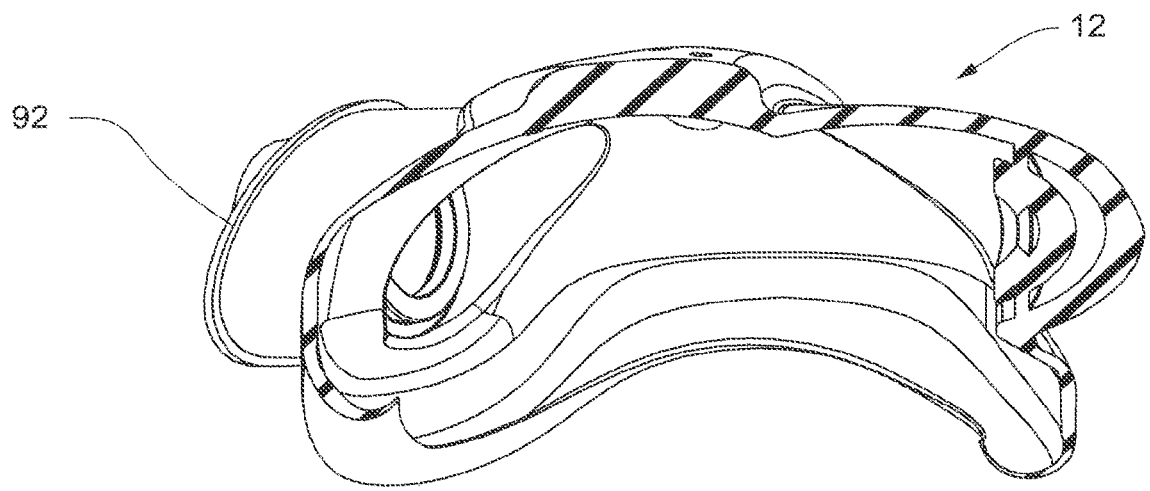
FIG. 35 schematically depicts a cross-sectional view of the cushion of FIG. 22 along line 35-35.
Figure 36:
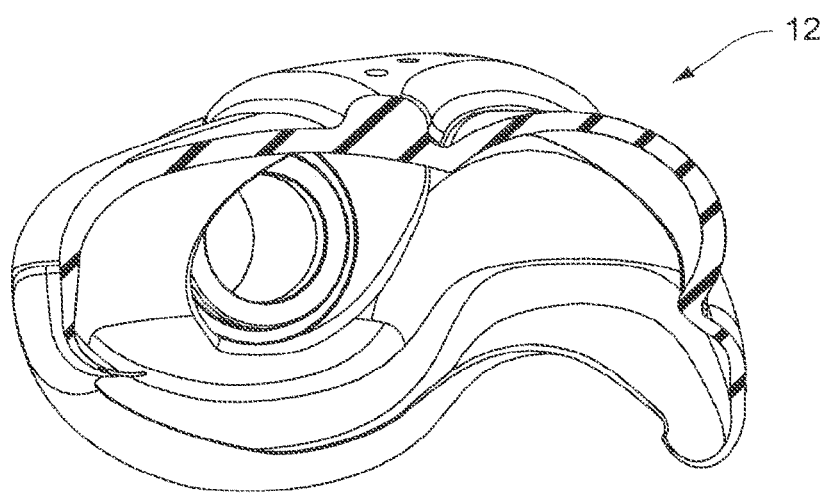
FIG. 36 schematically depicts a cross-sectional view of the cushion of FIG. 22 along line 36-36.
Figure 37:
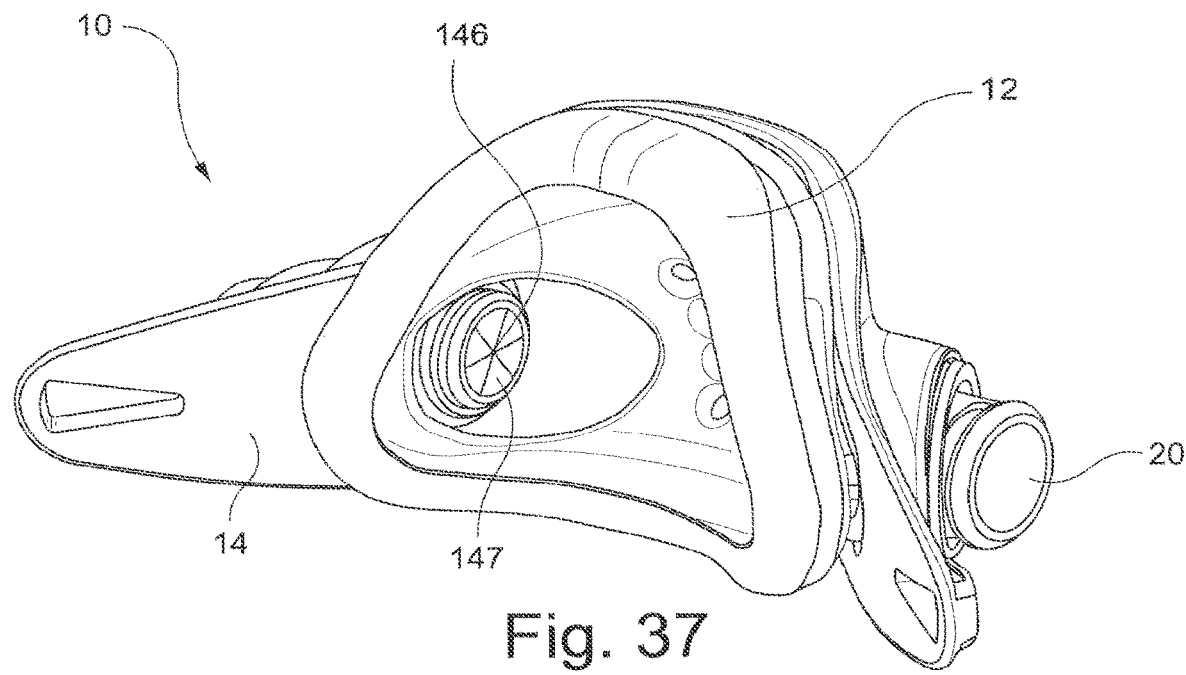
FIG. 37 schematically depicts a rear perspective view of a respiratory mask assembly with closed valve flaps according to another embodiment of the technology.

Referring to FIG. 21, a frame 14 according to another sample embodiment comprises a cross bar 48 extending between the wing portions 118 and the cylinders 112. The cross bar provides rigidity to the frame 14 and prevents creep of the frame 14 due to repeated bending of the frame 14.

1.2.3 Support Structure/Frame and Headgear Connection

Figure 72A:
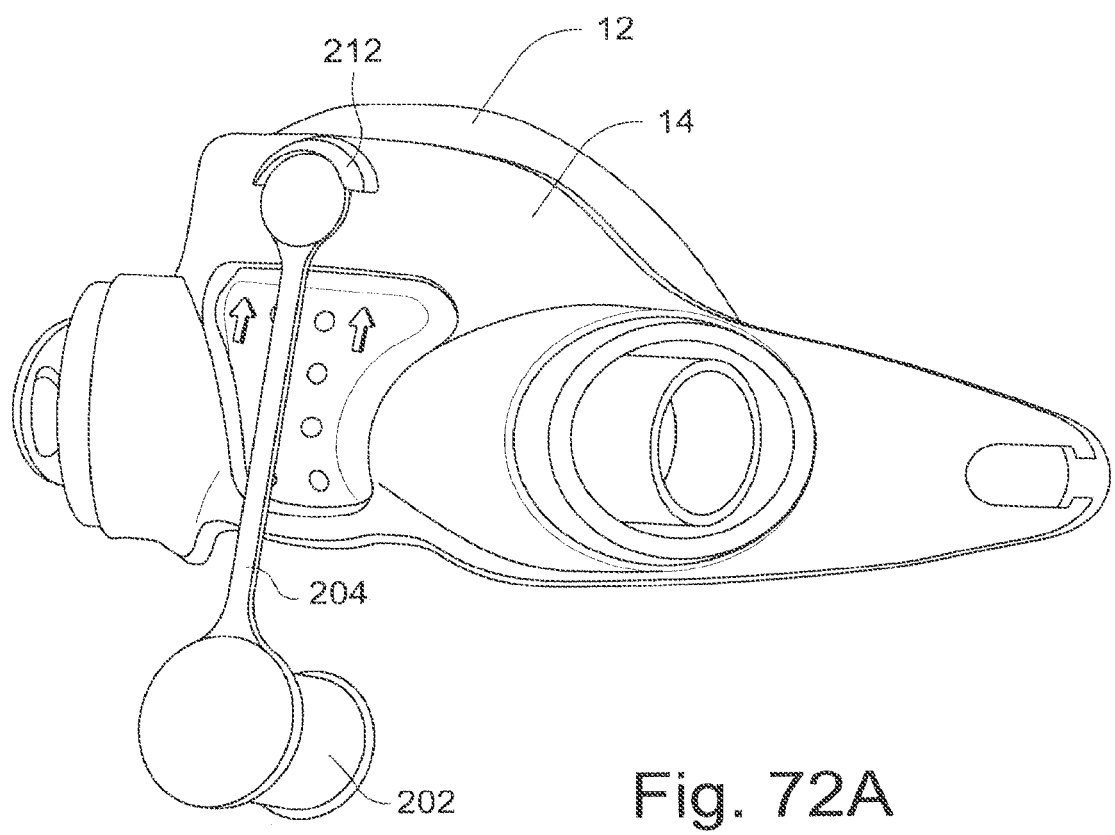
FIG. 72A schematically depicts a tether connecting a plug to a frame according to another sample embodiment of the technology.
Figure 72B:
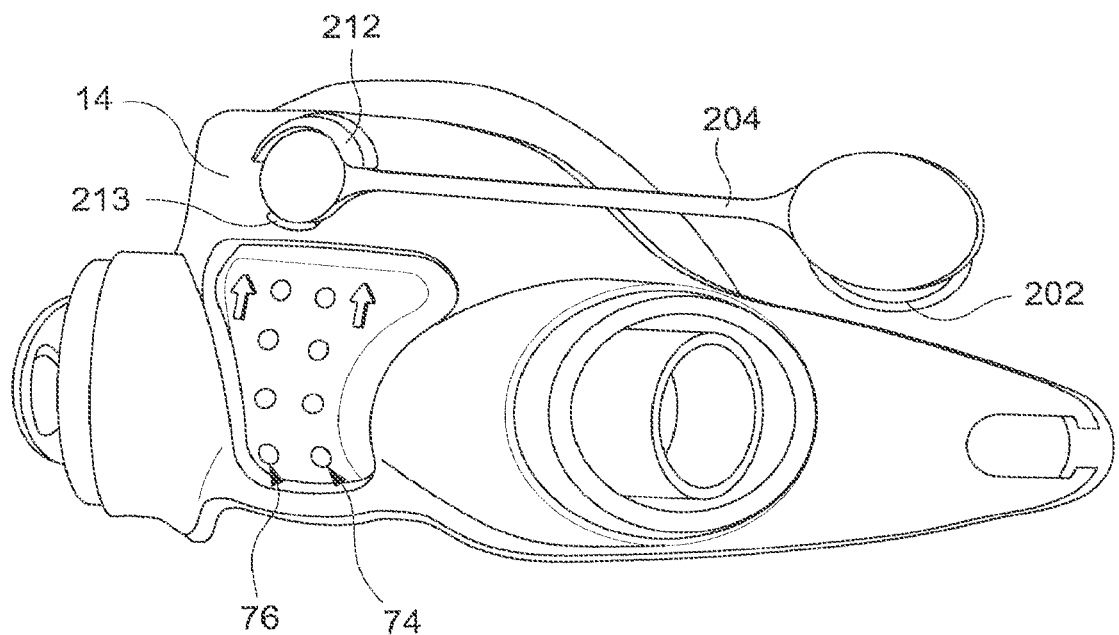
FIG. 72B schematically depicts a tether connecting a plug to a frame according to another sample embodiment of the technology.
Figure 72C:
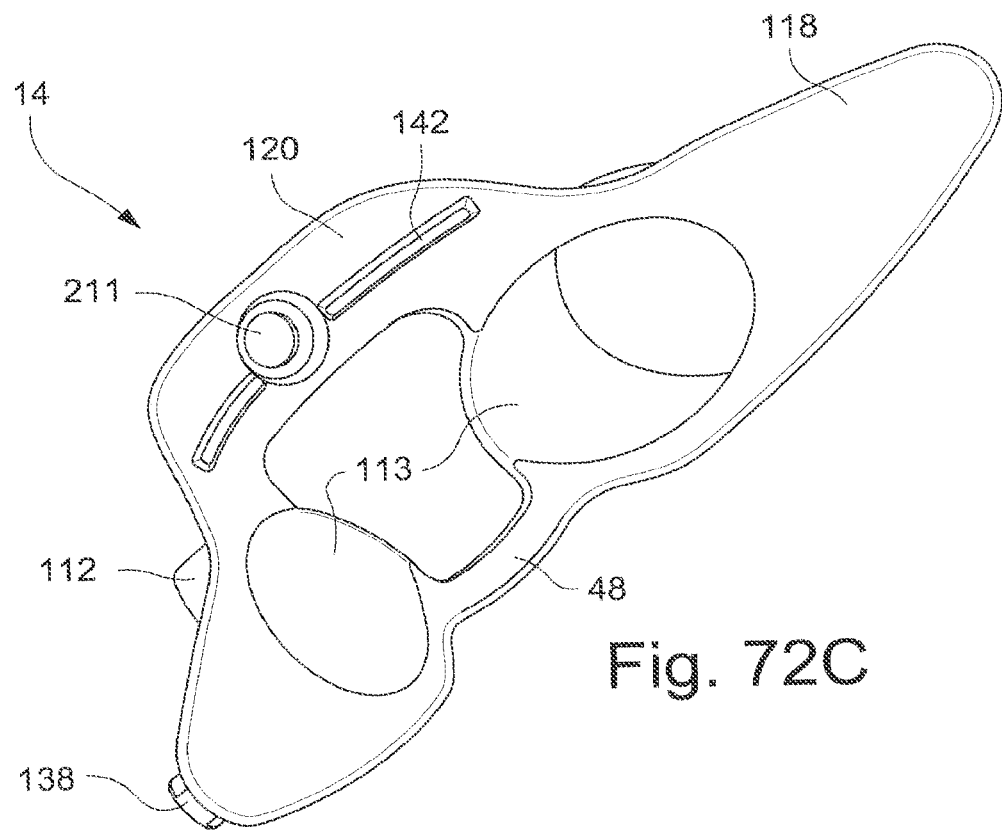
FIGS. 72C-72I depict a patient interface system (e.g. respiratory mask assembly) according to another sample embodiment of the technology.
Figure 72D:
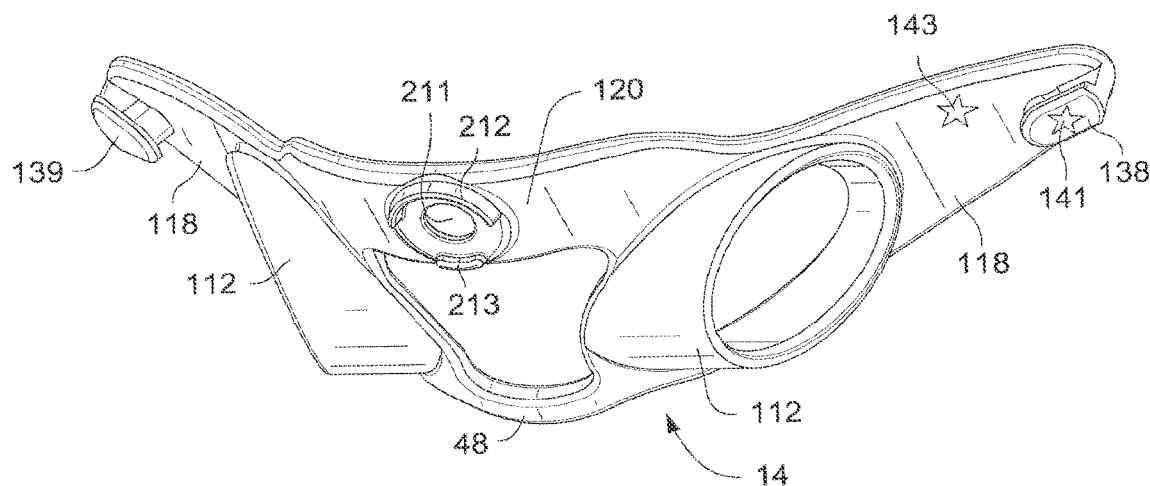
Figure 72E:
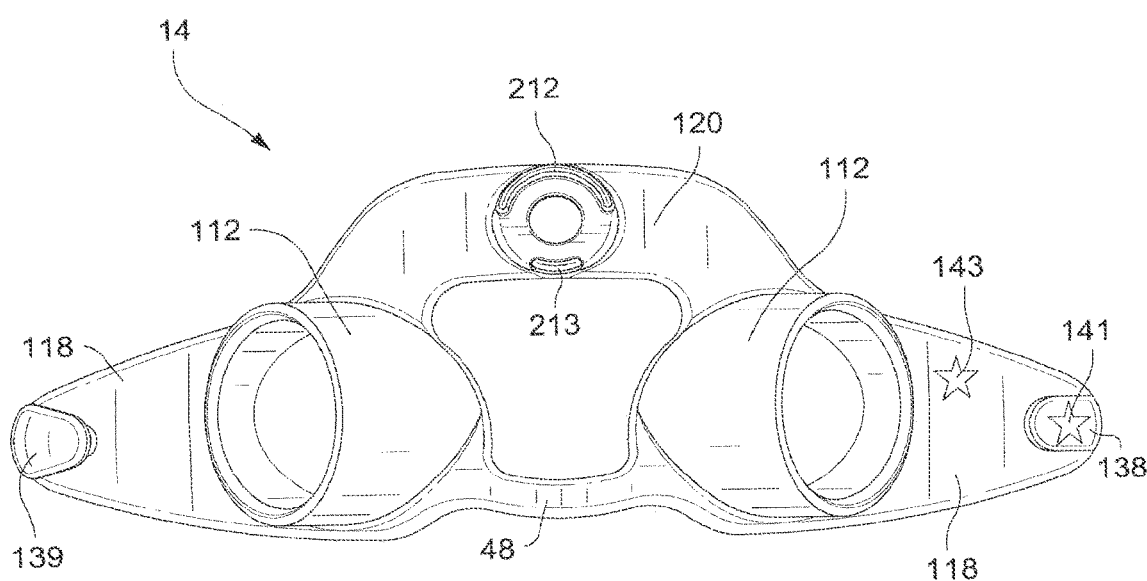
Figure 72F:
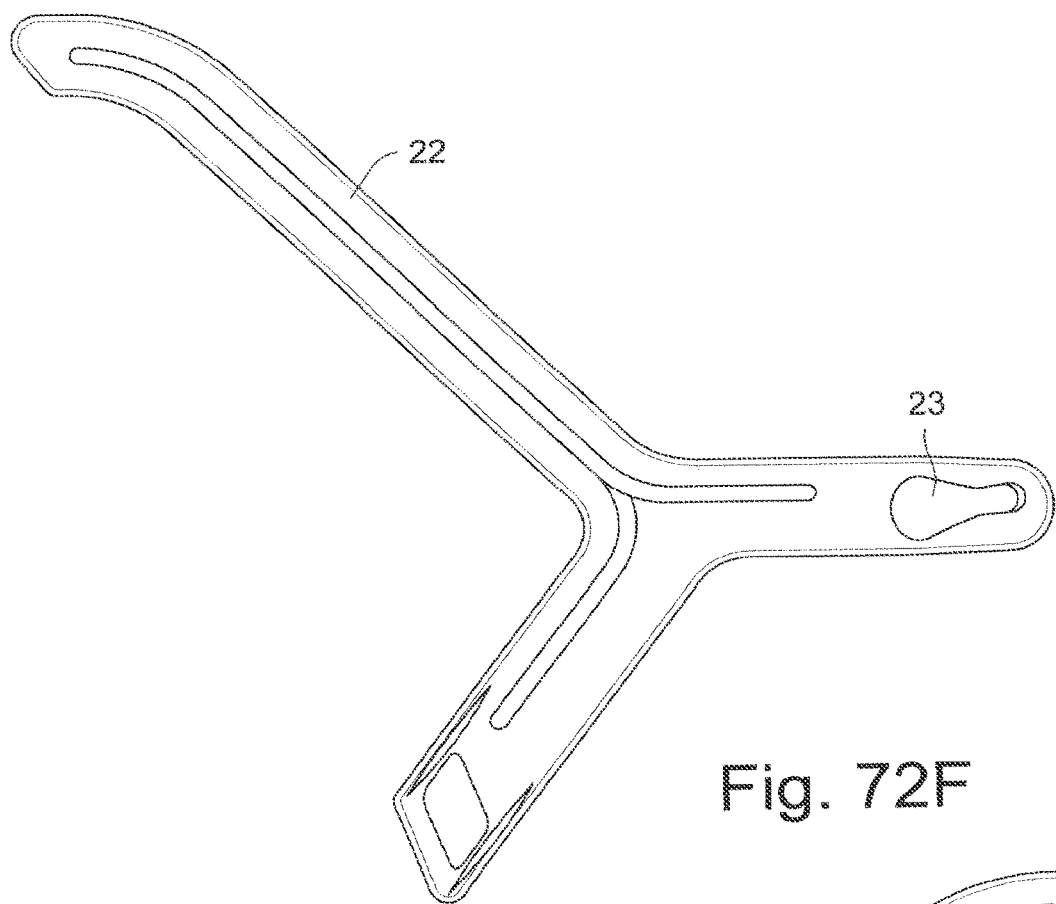
Figure 72G:
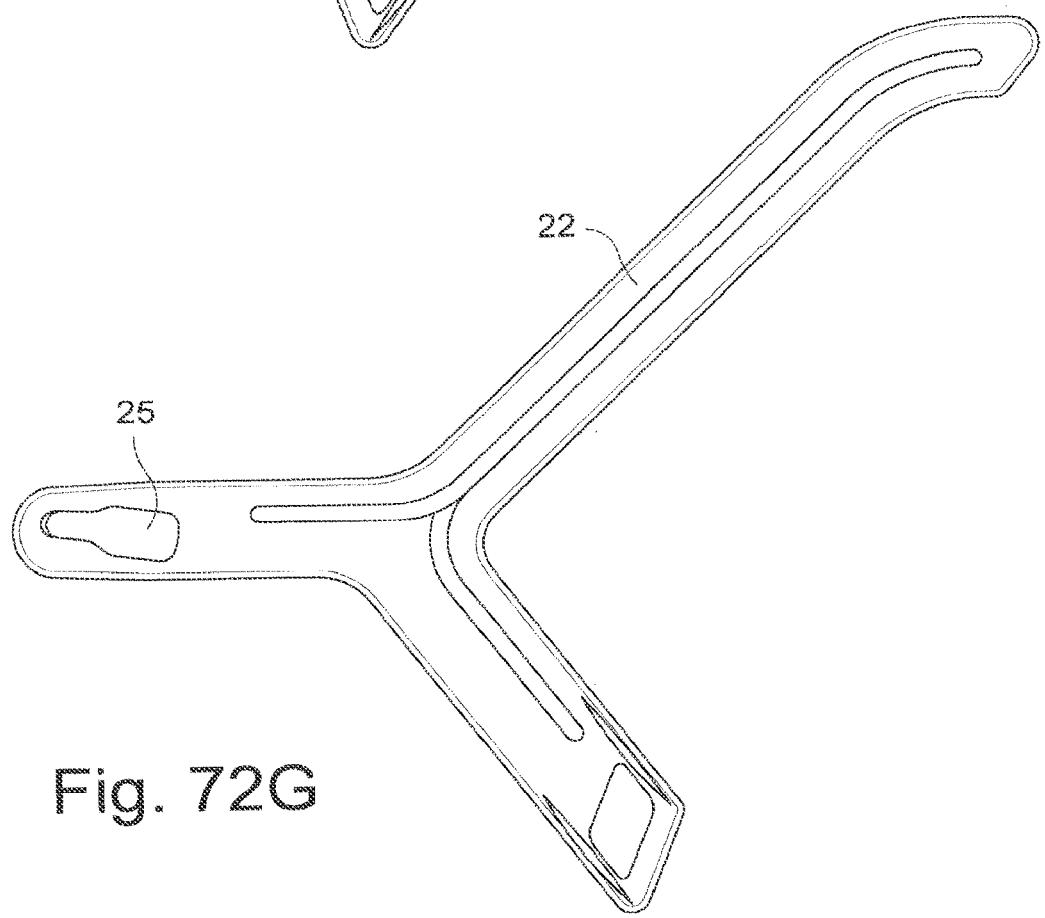

Referring to FIGS. 72C-72I, a patient interface system according to another exemplary embodiment includes a first indicia 141 on a left side connector 138 provided on the wing portion 118 of the frame 14. A second indicia 143 is also provided on the wing portion 118 and an angle to the first indicia 141. As shown in FIGS. 72E-72G, the right side rigidizer 22 (FIG. 72F) includes a hole 23 that is configured to receive the right side headgear connector 139 and the left side rigidizer 22 (FIG. 72G) includes a hole 25 that is configured to receive the left side headgear connector 138.

The right side headgear connector, or lug, 139 is larger than the hole 25 in the left side rigidizer 22. This prevents the left side rigidizer 22 from engaging with the right side headgear connector 139 and forces the user to assembly the left side rigidizer 22 with the left side headgear connector 138.

Figure 72H:
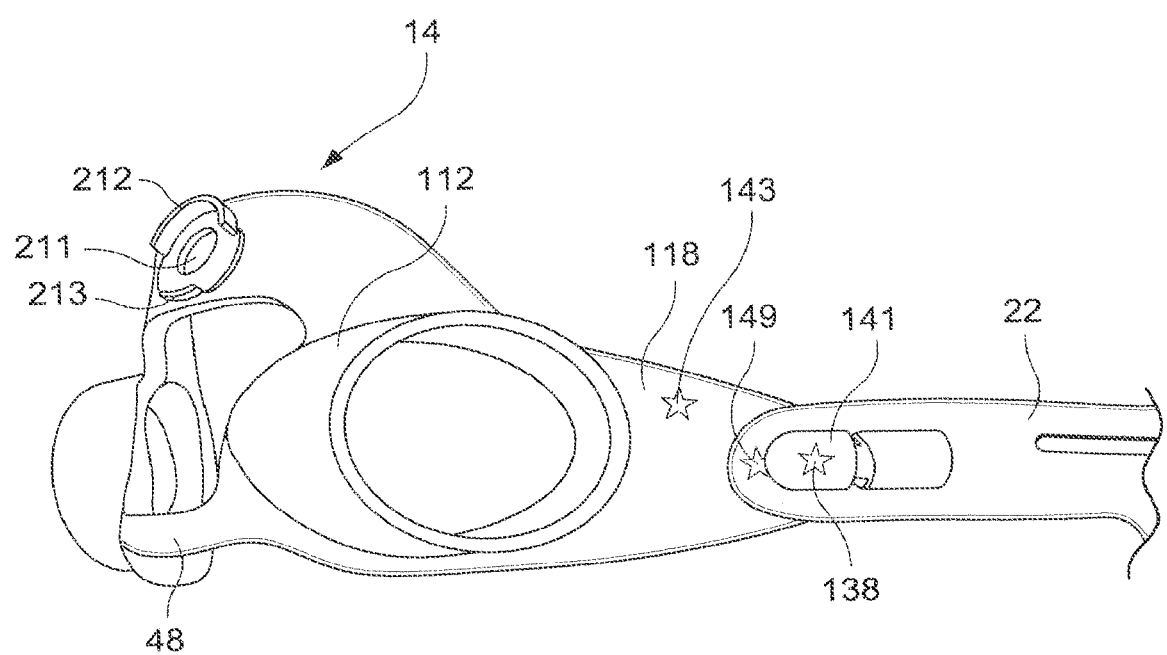

Referring to FIG. 72H, the left rigidizer 22 may also include an indicia 149 in addition to, or in place of, the indicia 143 on the wing portion 118 to indicate the correct connection between the left side rigidizer 22 and the left side connector portion, or lug, 138.

Figure 72I:
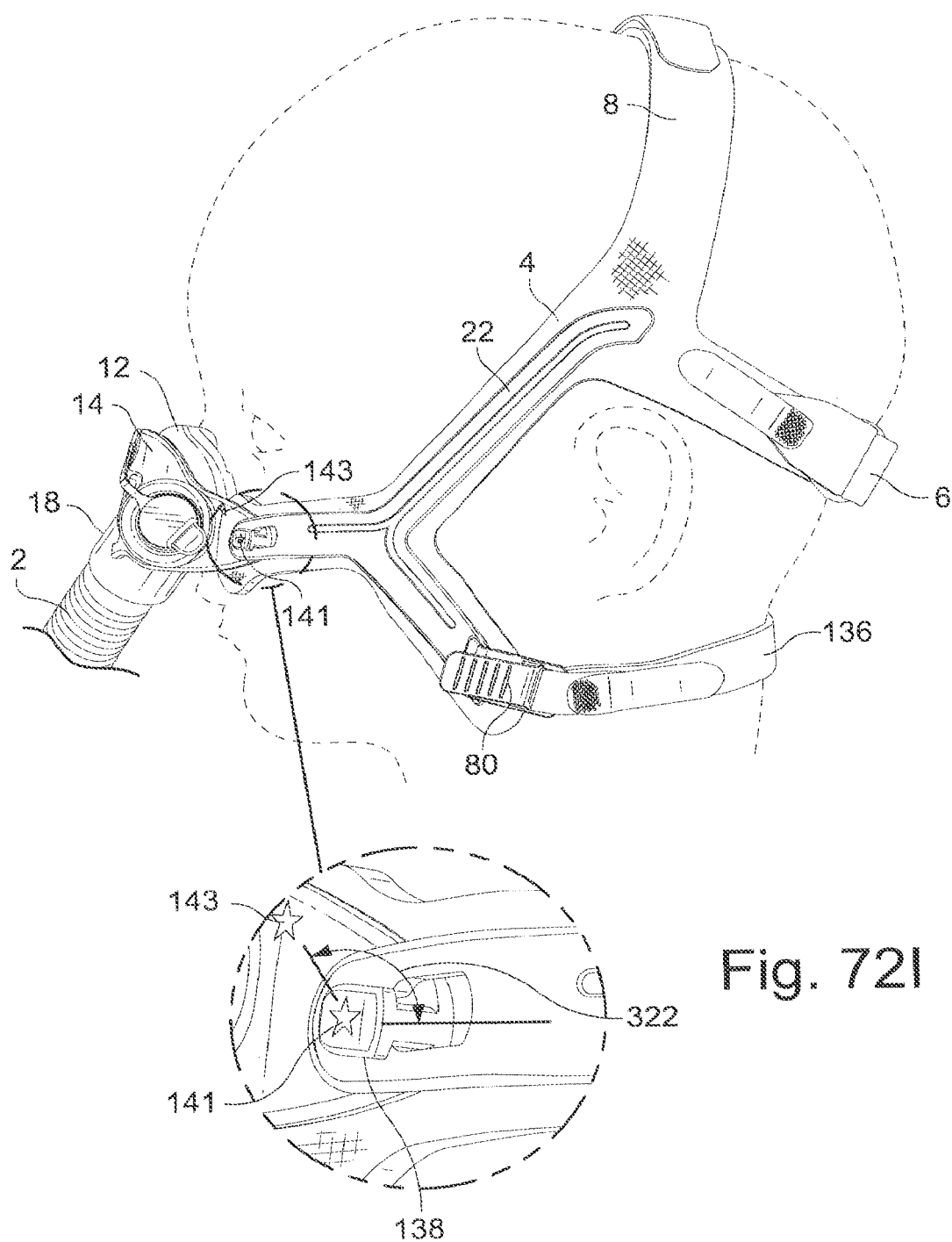

The first and second indicia 141, 143 may also serve as alignment indicators to assist the user in correctly connecting the headgear 16 to the frame 14. As shown in FIG. 72I, an angled connection between the headgear 16 and the frame 14 may be provided, as shown by the angle 322 between the first and second indicia 141, 143 and the rigidizer 22, to increase the force applied to the nose bridge region of the cushion 12 to improve the sealing function of the cushion. As shown in FIG. 72I, the angle may be 20°. However, it should be appreciated that the angle may be, for example, 2.5°, 5°, 7.5°, 10° or 15°.

1.3 Patient Interface Structure/Cushion

Referring now to FIGS. 3-10 and 20-36, the cushion 12 may be formed from a flexible, elastomeric material, for example silicone, that is designed to provide comfort to the patient while forming an adequate seal. The cushion defines an air chamber 26 into which the patient's nose is inserted in use. The cushion 12 locates above the patient's nasal vents and below the patient's nostril openings so that it does not impinge upon them. This allows a ready flow of air around the air chamber 26 to assist breathing and exhalation.

The cushion 12 may be configured to fit a patient population between the ages of, for example, about two to seven years.

The cushion 12 may be generally trapezoidal in shape and has a front side 28 facing away from the patient, a rear side 30 in contact with the patient's face in use, a top side 38, a bottom side 40 and two lateral sides 36. The top side 38 of the cushion 12 corresponds to the shorter of the substantially parallel sides of the trapezoid and is the side closest to the top of the patient's nose in use. The bottom side 40 of the cushion 12 corresponds to the longer of the substantially parallel sides of the trapezoid and is the side closest to the bottom of the patient's nares in use. The lateral sides 36 of the cushion 12 correspond to the non-parallel sides of the trapezoid and are closest to the patient's nostrils in use. The trapezoidal shape is anatomically suitable to allow the cushion 12 to surround the patient's nose without obstructing the patient's field of vision. This shape is particularly suitable for infants and children as they have 'button' style noses. This cushion shape allows the cushion to seal along the bridge of the nose which means that the cushion can fit different sizes of noses and therefore different ages of patients. It should also be appreciated that although in the embodiments depicted the cushion 12 is trapezoidal in shape, it could also be triangular, rectangular, circular or square.

The dimensions of the cushion 12 may be as disclosed in International Application PCT/AU2008/000270 (WO 2008/106716 A1), the entire contents of which are incorporated herein by reference. It should be appreciated that the dimensions may be otherwise. One reason for the provision of cushions within these dimensional ranges is that different patients (e.g. infants, children, babies born prematurely, teenagers and adults) present differently sized facial features. In order to provide a "one size fits all" cushion for patients in the range of 2-7 years of age, the dimensional ratio of length-to-width remains substantially constant while the depth changes very little. Children, for example children 2-7 years of age, generally have foreheads that protrude further from the face than the nose. During puberty, patient's noses grow more rapidly than during their preceding years, thus necessitating a mask of increased depth.

The facial shape of children, for example children 2-7 years of age, makes it difficult to provide an adult mask with a forehead support that has just been shrunk or made smaller. In order to maintain the mask on the patient's face in a sealed position, higher headgear forces are required to be applied due to the lack of a forehead support. However, young children still have relatively soft facial bones and the continuous application of pressure by the headgear during treatment may deform the patient's facial bones. This problem may be alleviated by changing the shape, or form, of the cushion. For example, the cushion(s) described herein may be substituted for a nasal pillows cushion, i.e. a cushion having a pair of nasal pillows configured to engage and seal the nares of the patient. As another example, nasal cannulae may be used to deliver the flow of breathable gas.

The rear side 30 of the cushion 12 comprises at least one thin flexible membrane 50 (FIG. 6) and at least one base wall 52 that connects the at least one membrane 50 with a dome portion 54 of the cushion 12 (i.e. at the front side 28 of the cushion 12). In the depicted sample embodiments, one membrane 50 and one base wall 52 are provided and together form part of the lateral sides 36, the top 38 and the bottom 40 of the air chamber 26 of the cushion 12.

The word "curvature" as used herein means the angle of a circle subtended by the membrane 50. A greater curvature allows the cushion membrane 50 to bend more easily since it rolls more easily. This, in turn, allows a greater degree of compression for a given force (i.e. the membrane 50 is softer). Thus, regions of high curvature have been incorporated into the top and bottom portions 56 and 60 of the mask cushion 12 which contact sensitive areas of the patients face (i.e. nasal bridge region and region between the patient's nose and mouth). This increases patient comfort and reduces the possibility of pressure sores. The advantage of the thicker bottom portion 60 is that it provides the mask 10 with greater stability.

In the depicted sample embodiments the base wall 52 is substantially aligned to the forward-aft direction of the mask 10 and varies in width around the perimeter of the mask 10. The base wall 52, like the membrane 50 comprises three main parts: a top portion 62; a bottom portion 64; and two side portions 66. The base wall 52 has a maximum width at its top and bottom portions 62 and 64. The base wall 52 tapers down to a minimum width at its side portions 66.

Figure 20:
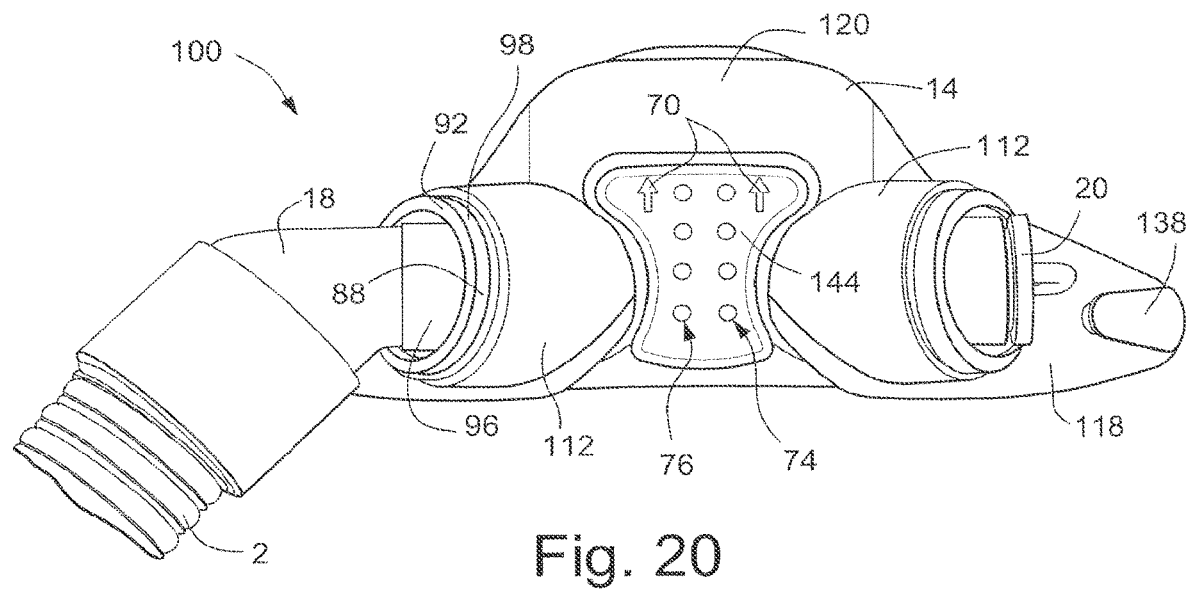
FIGS. 20 and 21 schematically depict front views of a respiratory mask assembly according to embodiments of the technology.

The thickness of the side portions 66 of the base wall 52 may be relatively constant. The thickness of the top and bottom portions 62 and 64 of the base wall 52 may taper down from a thickness about equal to the side portions 66 at the base of the base wall 52 to a transition region where the base wall 52 transitions into the membrane 50. The thickened portion 144 of the base wall 52 may serve a positioning function as the shape of the thickened portion generally corresponds to shape defined by the wing portions 118 and the arched bridge 120 of the frame 14. For example, as shown in FIGS. 20 and 21, the shape of the thickened portion 144 of the base wall 52 of the cushion 12 fits between the wing portions 118 and under the arched bridge 120 when the cushion 12 is correctly assembled on the frame 14. As the top portion 62 of the thickened portion 144 of the base wall 52 is wider than the bottom portion 64, if the cushion 12 is inserted incorrectly, e.g. upside down, the person assembling the mask will get a tactile indication that the cushion 12 is being improperly attached to the frame 14. The bridge 120 also may aid alignment due to the shape of the bridge matching the shape of raised portion 114.

The cushion 12 may be integrally formed from, for example, silicone or foam by an injection molding process. The cushion 12 may also be formed by compression molding. The cushion may be formed, for example, by compression molding a flexible material, for example, silicone rubber. The cushion may be post cured. The cushion 12 may have a hardness of, for example, about 35 to 50, for example about 39 to 45, on the Shore A hardness scale. As the cushion 12 includes the base wall 52, the aperture 55 in the membrane 50 may be formed in the mold. Alternatively, the aperture 55 may be removed in a post processing step such as cutting. This post processing step could be done in the mold or off the mold. The cushion 12 may include a lip or bead 68 on the membrane 50 that serves to prevent tearing of the membrane 50 as it is removed from the mold.

1.3.1 Membrane

The membrane 50 forms a seal against the adjacent portion of the patient's face around the patient's nose while the base wall 52 elevates the front side 28 of the cushion 12 above the patient's nose. This allows pressurised air (e.g. CPAP therapy) to be delivered to the patient. Although one membrane is shown, it should be appreciated that the cushion 12 may be a double membrane cushion, or that any number of membranes greater than one may be provided.

Figure 7:
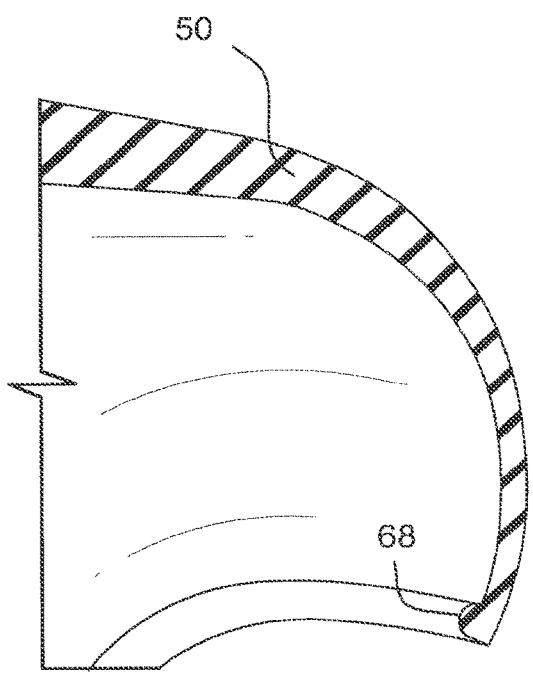
FIG. 7 schematically depicts an enlarged cross-sectional view of a portion of the patient interface, or cushion, of FIG. 6.

As shown in FIG. 7, the end of the membrane 50 may be provided with a lip or bead 68 to reduce, or minimize, tearing of the membrane 50, for example during demolding of the cushion 12 as described in more detail below. The lip 68 may be, for example, about 0.10 to 0.20 mm wide, for example about 0.15 mm wide.

Figure 6:
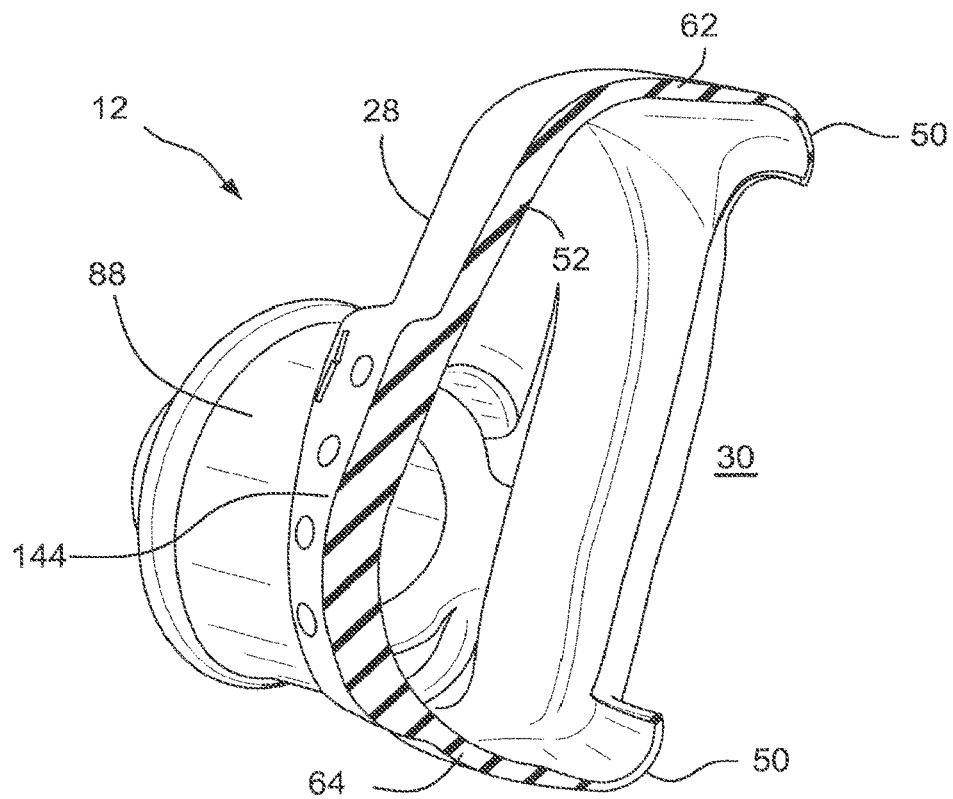
FIG. 6 schematically depicts a cross-sectional section view of the patient interface, or cushion, of FIGS. 3-5.

As shown in FIGS. 6 and 7, the cushion 12 may consist of a single membrane 50 having a thickness in the sealing area that may vary from, for example, about 0.10 to 0.70 mm, for example about 0.20 to 0.58 mm. The cushion 12 provides a comfortable seal on the face of the patient with a minimum force.

The membrane 50 defines an aperture 55 (FIG. 4) for receiving the patient's nose. The shape of the aperture 55 is similar to the shape of the cushion 12. The dimensions of the aperture 55 may be as disclosed in International Application PCT/AU2008/000270 (WO 2008/106716 A1), the entire contents of which are incorporated herein by reference. It should be appreciated that the dimensions may be otherwise.

The membrane 50 generally has three portions, each having a different cross-sectional shape. A top portion 56 is located substantially over the patient's nasal bridge in use, two side portions 58 are located substantially at either side of the patient's nares in use, and a bottom portion 60 is located substantially under the patient's nose in use. The exterior dimensions of the membrane 50 from a rear perspective are the same as the corresponding overall dimensions of the cushion 12 as detailed above.

The cross-sections of each of these three portions 56, 58 and 60 of the membrane 50 are generally C-shaped but they vary with respect to radius, curvature and material thickness. By way of a general comparison, the top and bottom portions 56 and 60 have a larger curvature or roll than the side portions 58 and the bottom portion 60 is thicker than the top 56 and side portions 58.

Figure 79:
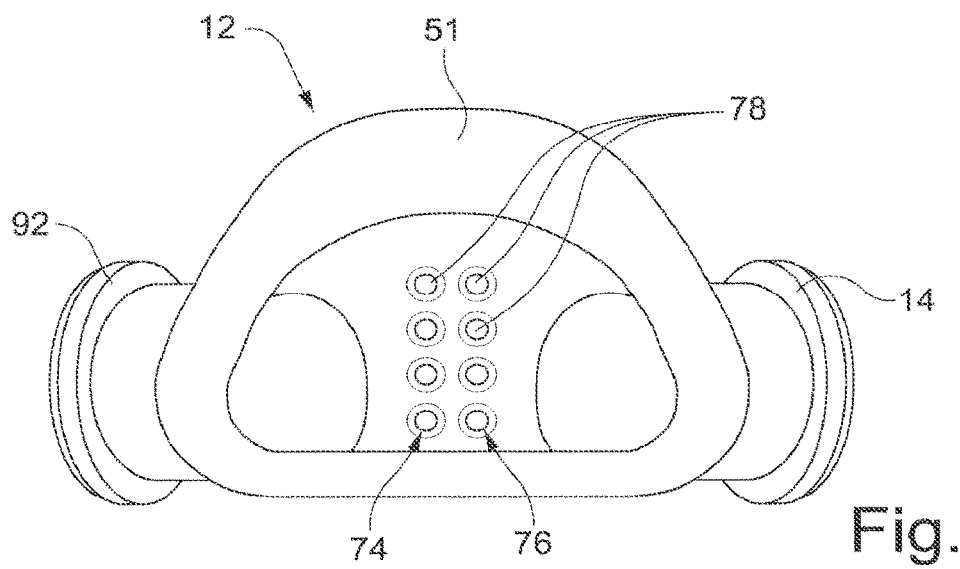
FIG. 79 schematically depicts a rear view of a cushion according to another sample embodiment of the technology.
Figure 80:
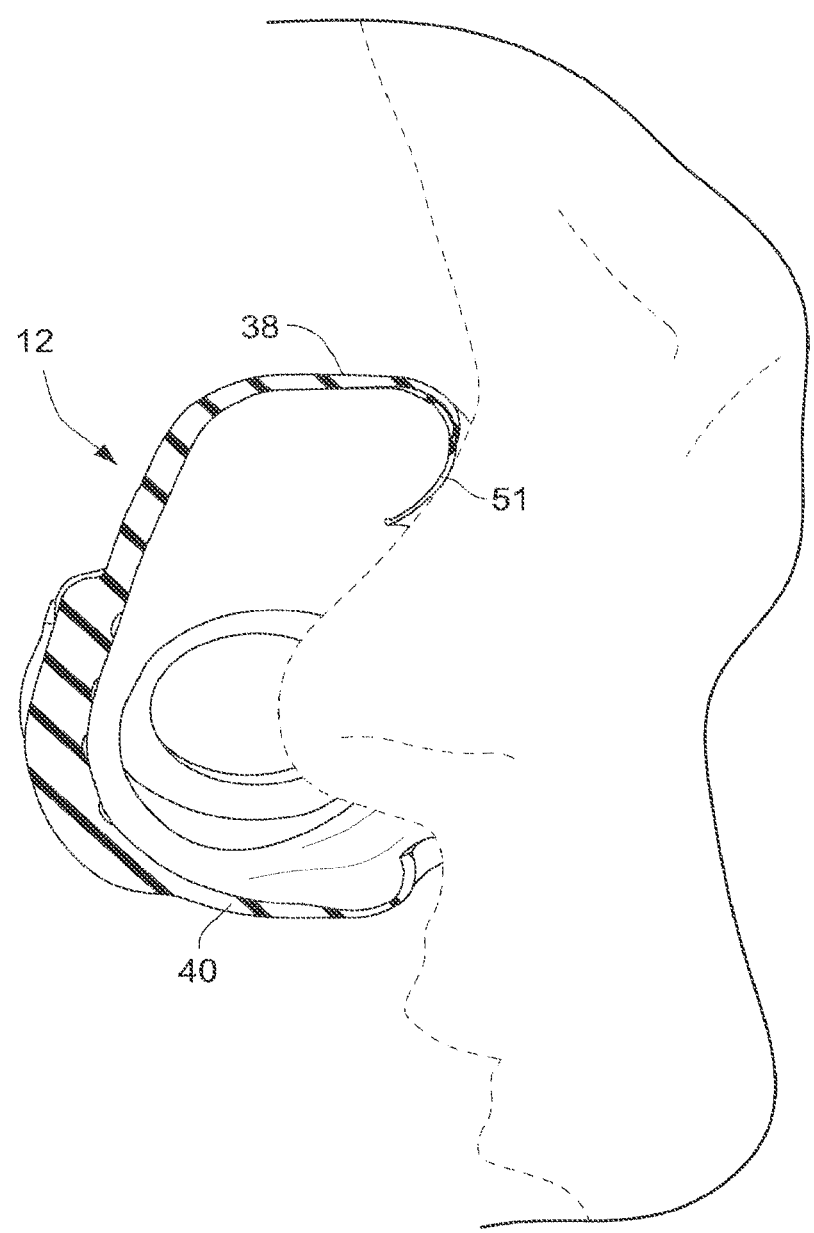
FIG. 80 is a cross-sectional view of a cushion on a model patient's head according to another sample embodiment of the technology.
Figure 81:
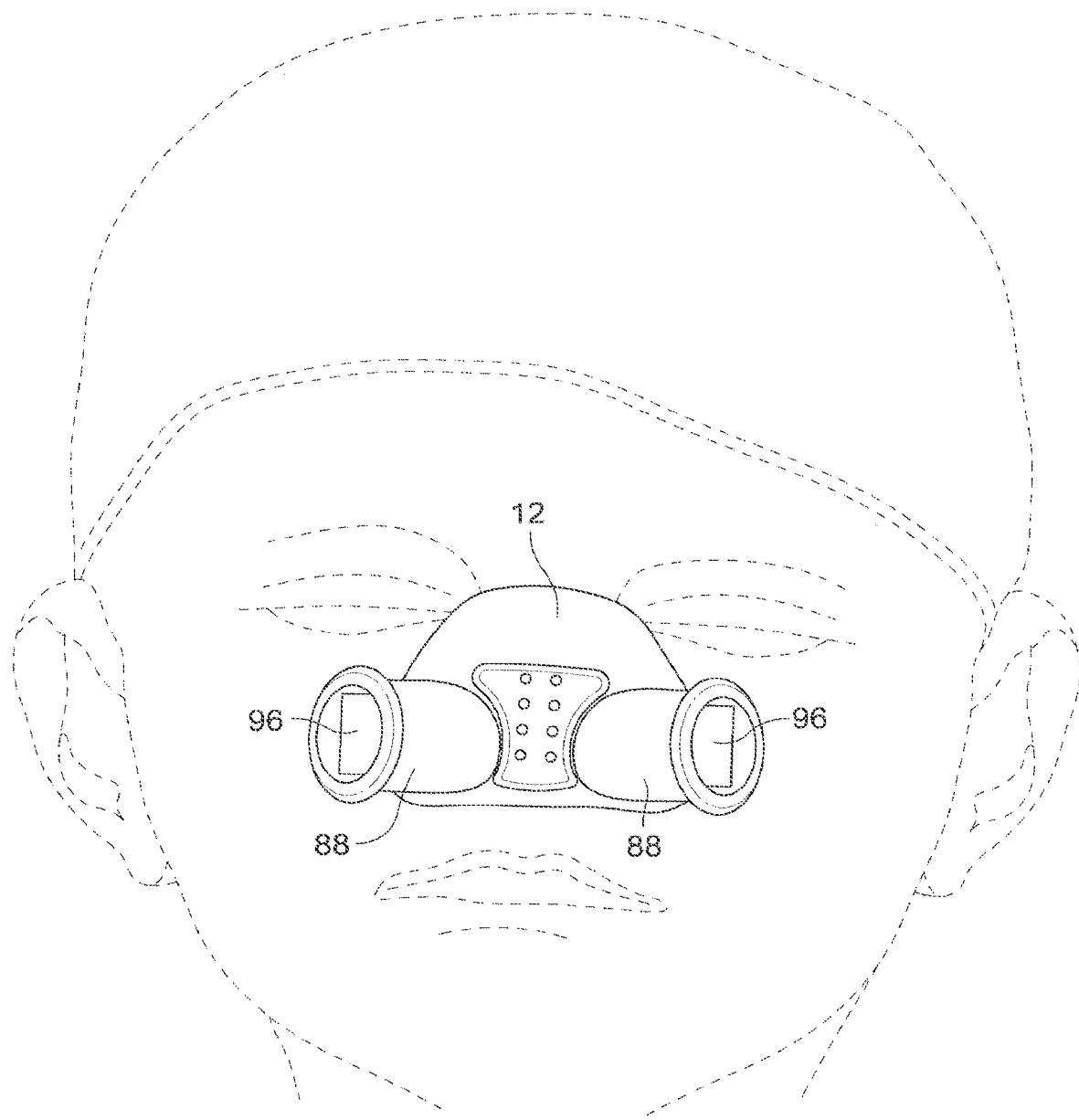
FIG. 81 schematically depicts a cushion and frame on a model patient's head.
Figure 82:
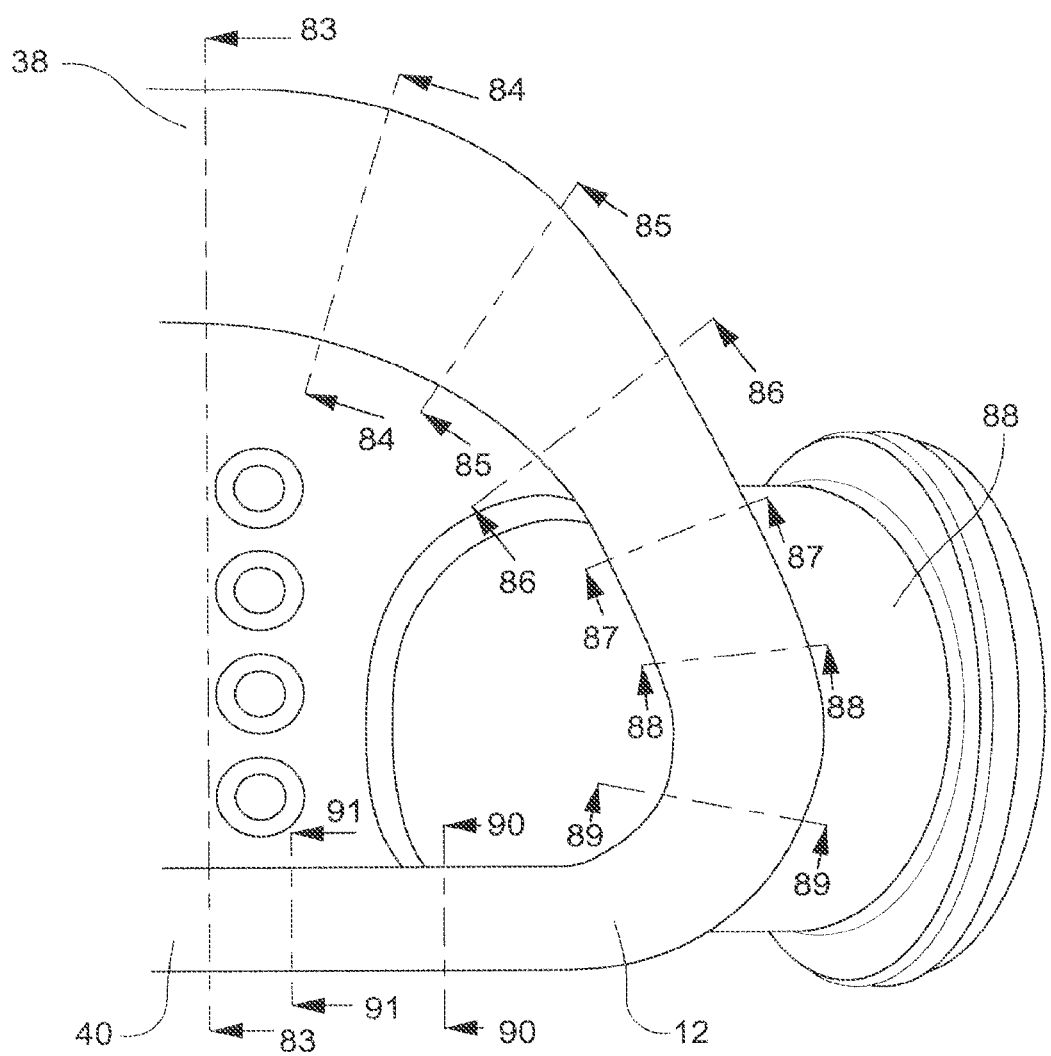
FIG. 82 schematically depicts a partial rear view of a cushion.
Figure 83:
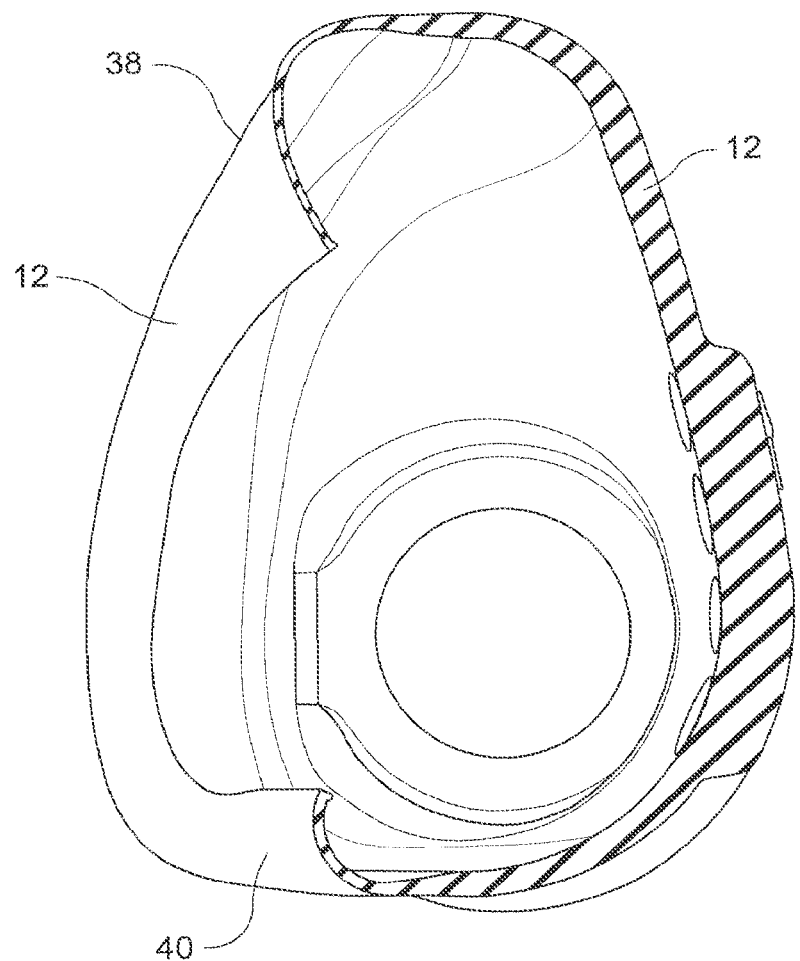
FIG. 83 schematically depicts a cross-sectional view of the cushion of FIG. 82 along line 83-83.
Figure 84:
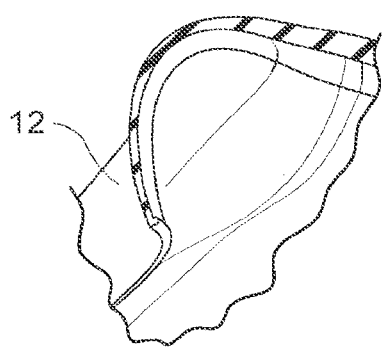
FIG. 84 schematically depicts a cross-sectional view of the cushion of FIG. 82 along line 84-84.
Figure 85:
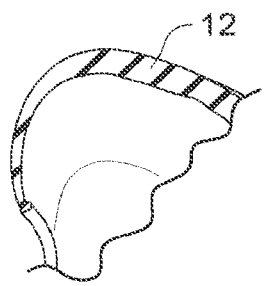
FIG. 85 schematically depicts a cross-sectional view of the cushion of FIG. 82 along line 85-85.
Figure 86:
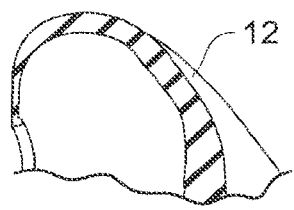
FIG. 86 schematically depicts a cross-sectional view of the cushion of FIG. 82 along line 86-86.
Figure 87:
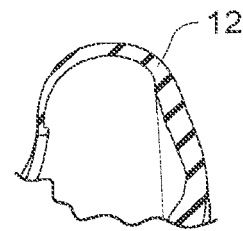
FIG. 87 schematically depicts a cross-sectional view of the cushion of FIG. 82 along line 87-87.
Figure 88:
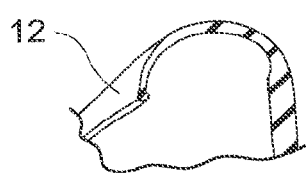
FIG. 88 schematically depicts a cross-sectional view of the cushion of FIG. 82 along line 88-88.
Figure 89:
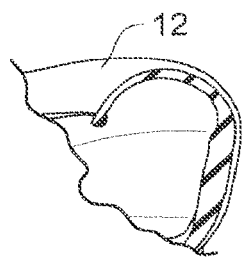
FIG. 89 schematically depicts a cross-sectional view of the cushion of FIG. 82 along line 89-89.
Figure 90:
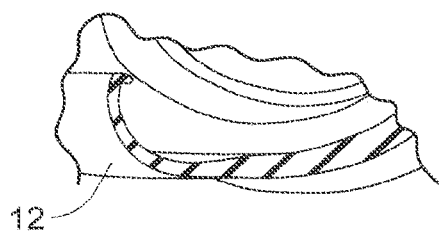
FIG. 90 schematically depicts a cross-sectional view of the cushion of FIG. 82 along line 90-90.
Figure 91:
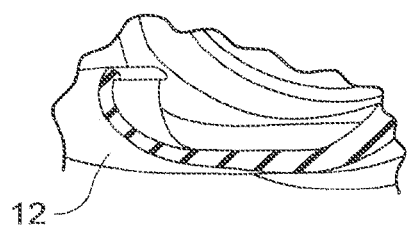
FIG. 91 schematically depicts a cross-sectional view of the cushion of FIG. 82 along line 91-91.

Referring to FIG. 79, the cushion 12 may include a membrane 51 that is increased in length compared to the membrane 50 shown in FIG. 6. The increased membrane length provides sealing contact between the membrane 51 and the face of the patient over a larger surface area and is more stable. The increased length of the membrane 51 also prevents disruption of the seal if the child moves the cushion, for example, during sleep. Furthermore, the increased length of the membrane 51 prevents or reduces the likelihood of the cushion inverting which would make it difficult to seal the cushion on the patient.

1.3.2 Cushion Transparency

In one sample embodiment, the cushion 12 is substantially transparent or water clear such that a parent or clinician can inspect the patient's nares. This is particularly useful in the case of children to ensure that there are no physical obstructions to nasal breathing (e.g. mucus). Additionally, a clear path of sight may also assist in fitting the mask to the patient by a third party (for example, nurse or parent). In other sample embodiments, the cushion 12 is translucent or frosted so that any obvious obstructions to breathing can still be identified and rectified. The membrane 50 may be translucent or frosted also, or the membrane 50 may be clear or transparent. The membrane may also have a polished finish which provides increased friction against the face of the patient, to assist in maintaining a seal between the membrane 50 and the patient's face.

1.3.3 Vent

The cushion 12 includes an exhalation vent 72 in the form of two arrays 74 and 76 of apertures 78 disposed along respective parallel rows. The apertures 78 are provided in the thickened portion 144 of the base wall 52 of the cushion. The arrays 74, 76 of vent holes 78 provide a predetermined vent flow from the cushion 12 when the cushion 12 is sealed with the elbow 18 and the plug 20. The parallel rows of vent apertures also facilitate tooling of the machinery for forming the cushion. It should be appreciated that other known venting arrangements could be incorporated into the cushion 12 and frame 14 of the respiratory mask assembly 10. The vent holes 78 may have a diameter of, for example, about 1.50 mm or about 1.60 mm. It should be appreciated that the diameter of the vent holes may be other than as shown and described.

1.3.4 Cushion Orientation

Figure 3:
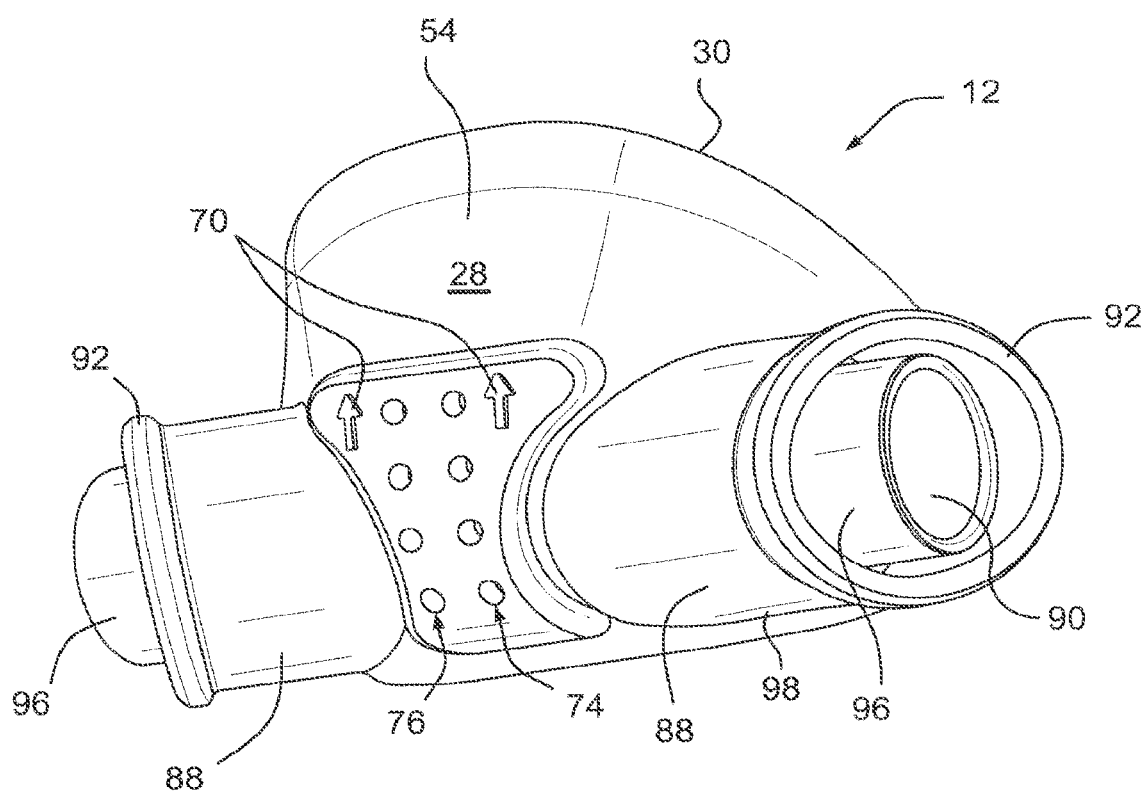
FIG. 3 schematically depicts a front perspective view of a patient interface, or cushion, of the respiratory mask assembly of FIG. 1.
Figure 4:
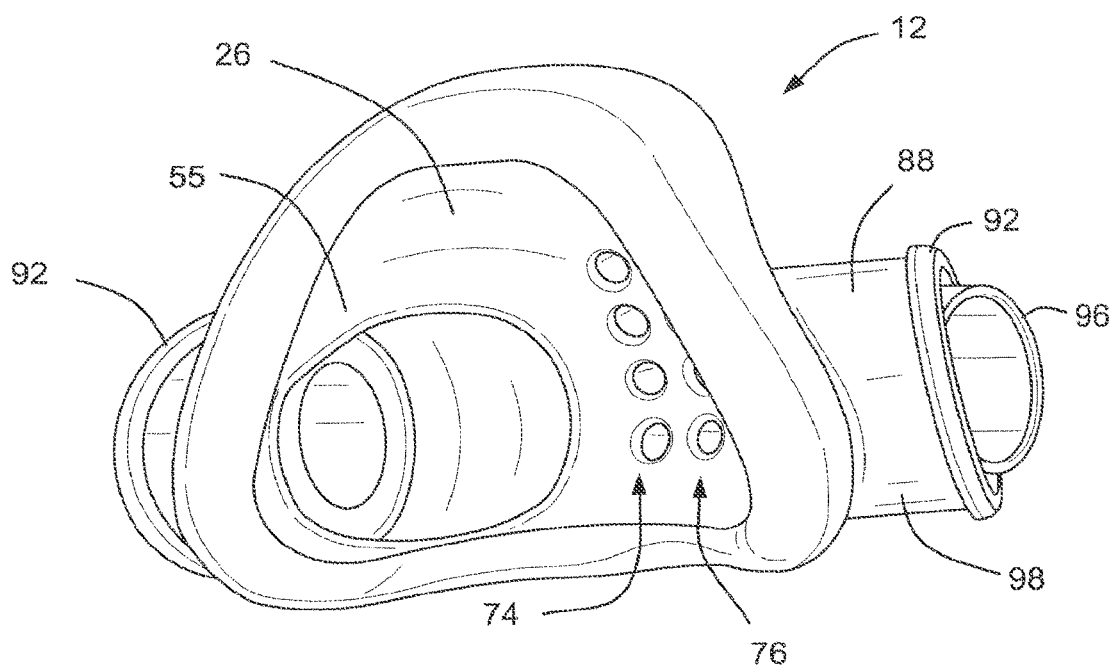
FIG. 4 schematically depicts a rear perspective view of the patient interface, or cushion, of FIG. 3.
Figure 5:
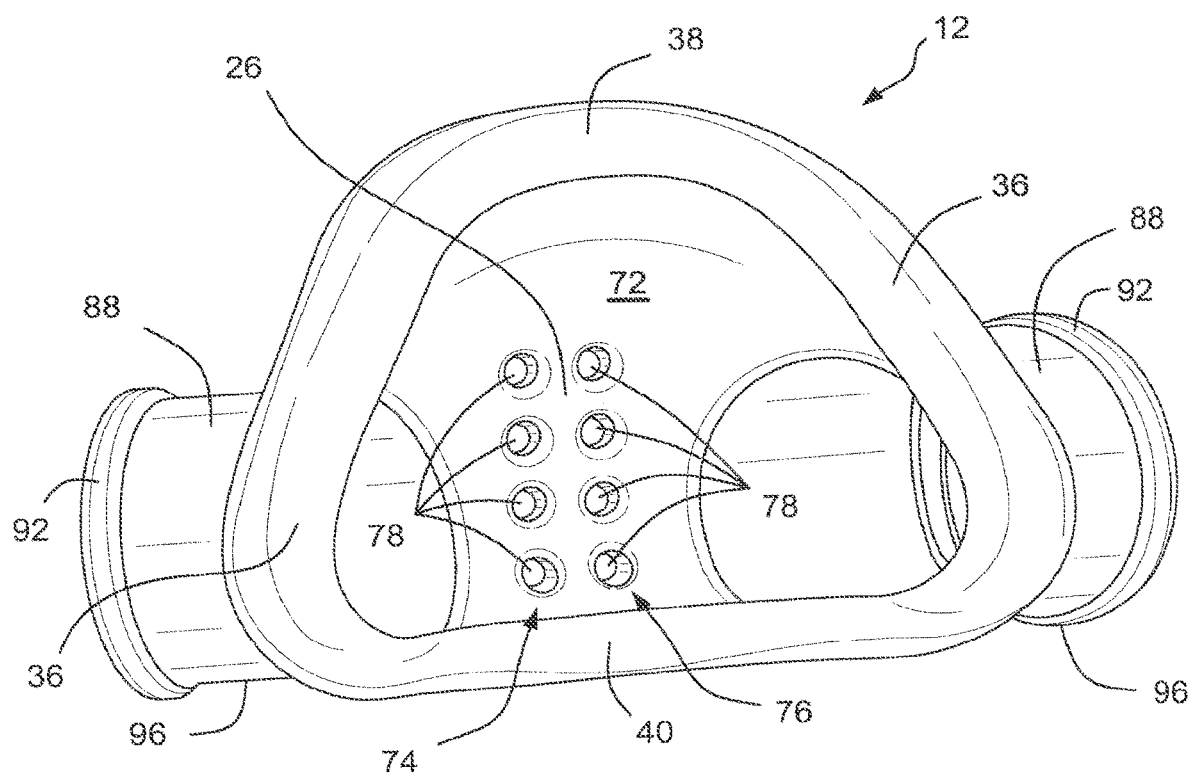
FIG. 5 schematically depicts a rear perspective view of the patient interface, or cushion, of FIG. 3.

The front surface 28 of the cushion 12 may also include at least one orientation element, such as indicia 70 that is/are configured to indicate the correct direction or orientation for assembling the cushion 12 with the frame 14. As shown in FIG. 3, the indicia 70 may be provided adjacent the arrays 74, 76 of vent holes 78. However, it should be appreciated that the indicia may be provided at another portion of the cushion 12.

Figure 10:
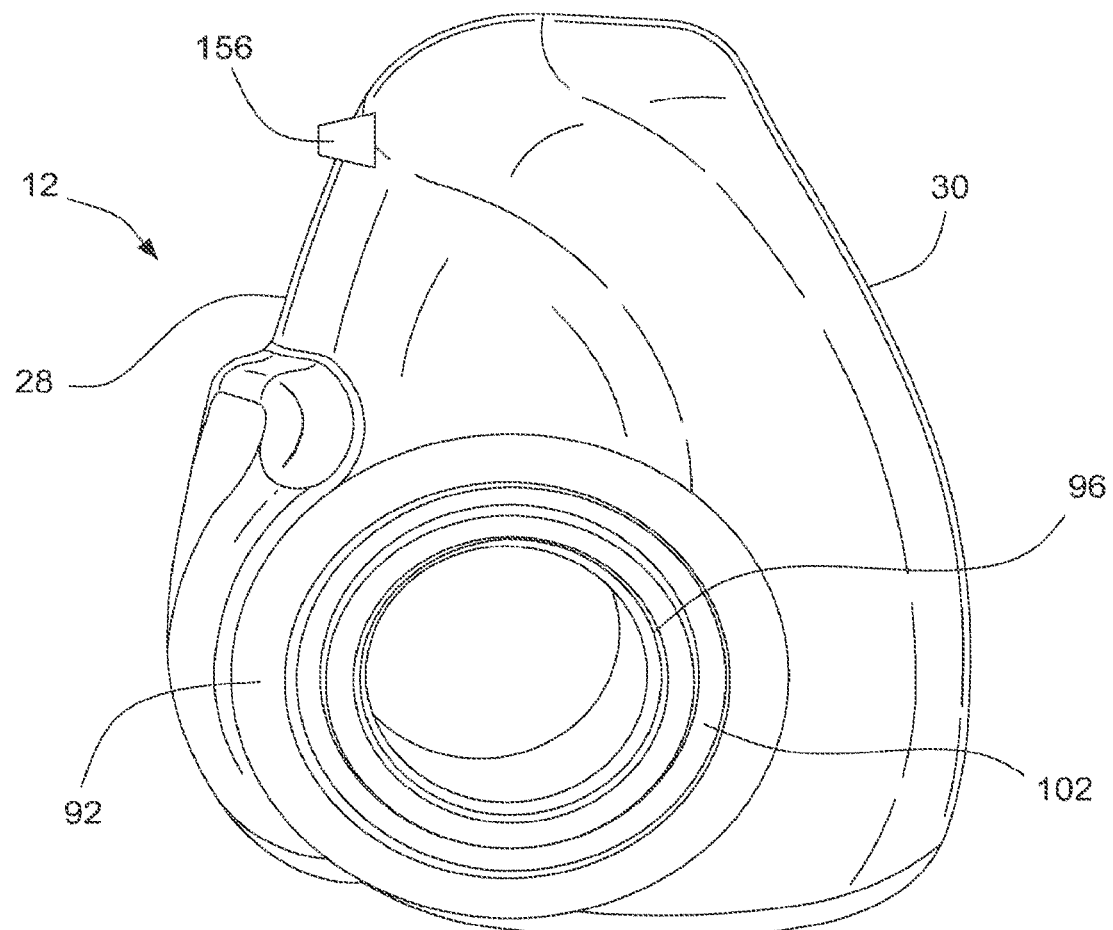
FIG. 10 schematically depicts a side view of a patient interface, or cushion, according to another embodiment of the technology.

Referring to FIG. 10, according to another embodiment of the technology, the cushion 12 may comprise other orientation elements such as a lug, or lugs 156 that are configured to be engaged in a hole or holes, on the frame 14 to indicate correct assembly of the cushion 12 with the frame 14.

Referring to FIGS. 20 and 21, the thickened portion 144 of the base wall 52 may serve a positioning function as the shape of the thickened portion generally corresponds to shape defined by the wing portions 118 and the arched bridge 120 of the frame 14. For example, as shown in FIGS. 20 and 21, the shape of the thickened portion 144 of the base wall 52 of the cushion 12 fits between the wing portions 118 and under the arched bridge 120 when the cushion 12 is correctly assembled on the frame 14. As the top portion 62 of the thickened portion 144 of the base wall 52 is wider than the bottom portion 64, if the cushion 12 is inserted incorrectly, e.g. upside down, the person assembling the mask will get a tactile indication that the cushion 12 is being improperly attached to the frame 14.

Figure 78:
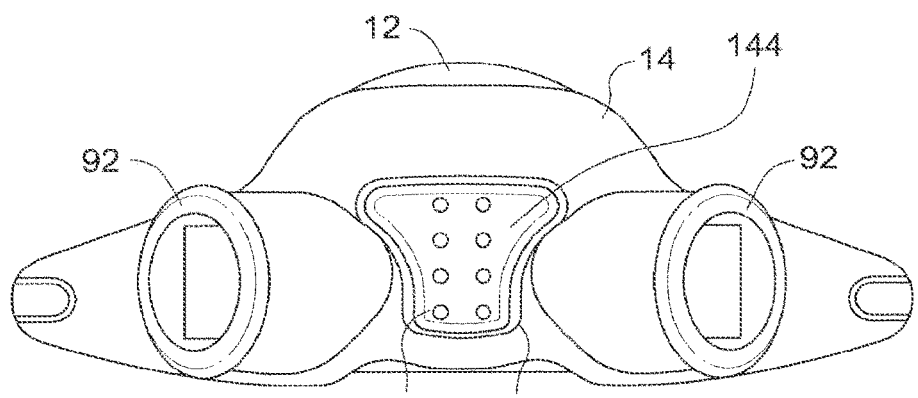
FIG. 78 schematically depicts a front view of a cushion and frame according to another sample embodiment of the technology.

Referring to FIG. 78, a patient interface according to another sample embodiment includes a frame 14 and a cushion 12. The shoulders 92 of the cushion 12 are configured to engage the frame 14 to secure the cushion 12 to the frame 14. The exhalation vents 72 of the cushion 12 may be provided in a thickened portion 144 of the cushion so that the vents can nest or slot into an aperture 214 provided in the frame 14. This assembly provides an extra visual and/or tactile cue for correct assembly of the cushion 12 to the frame 14. The thickened portion 144 of the cushion and the aperture 214 provided in the frame 14 thus provide another orientation element.

Figure 123:
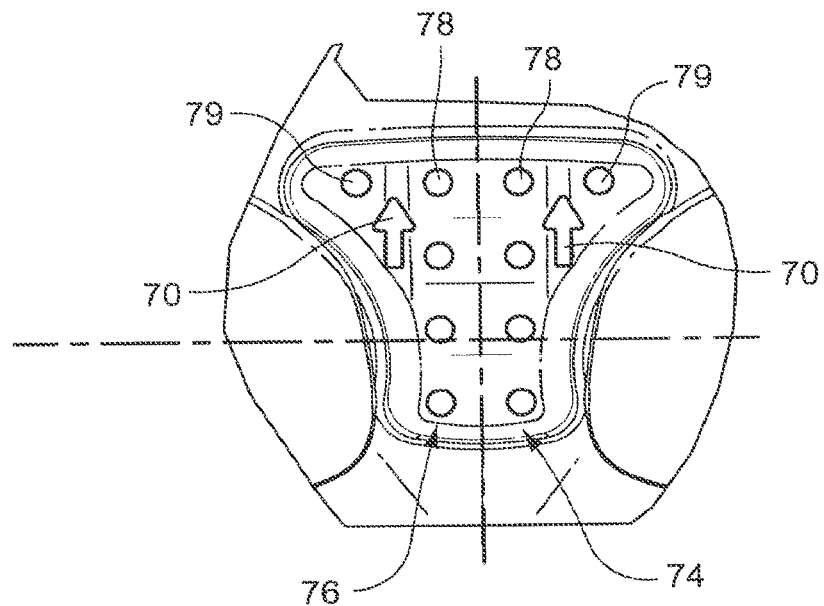
FIGS. 123-127 depict a patient interface structure (e.g. cushion) and patient interface system (e.g. respiratory mask assembly) according to another sample embodiment of the technology.
Figure 124:
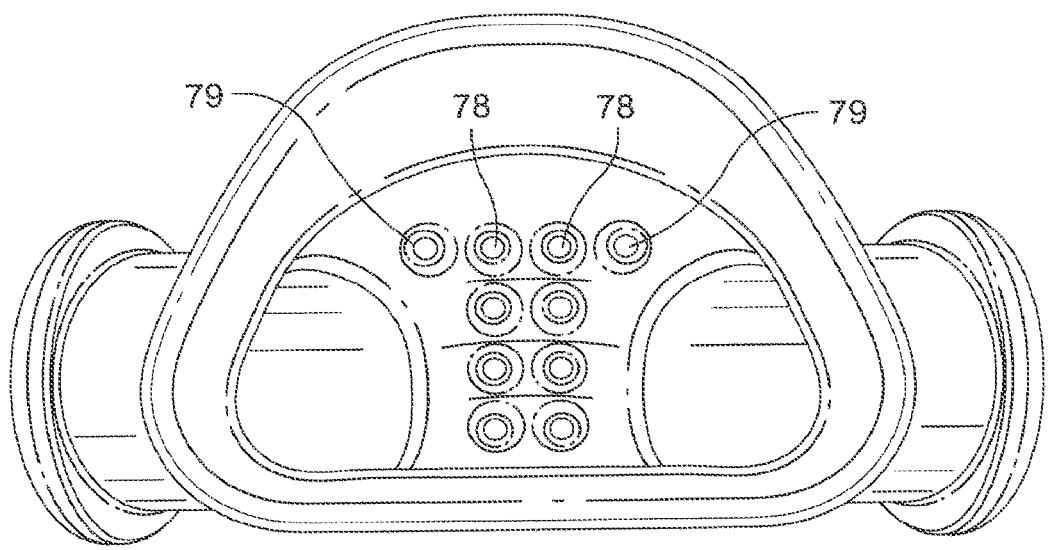
Figure 125:
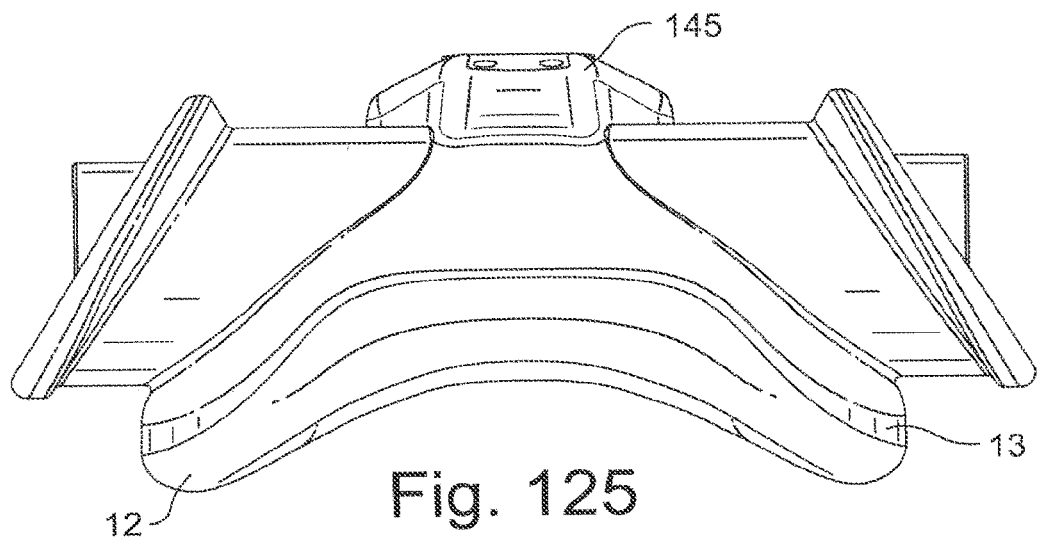
Figure 126:
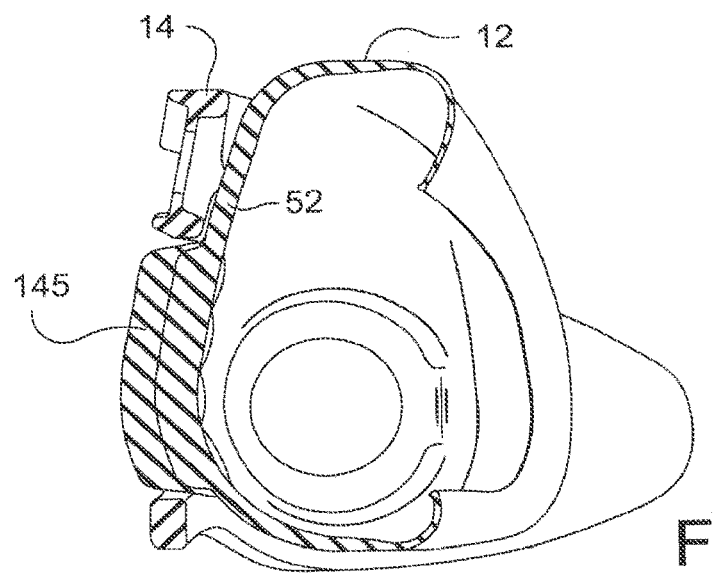
Figure 127:
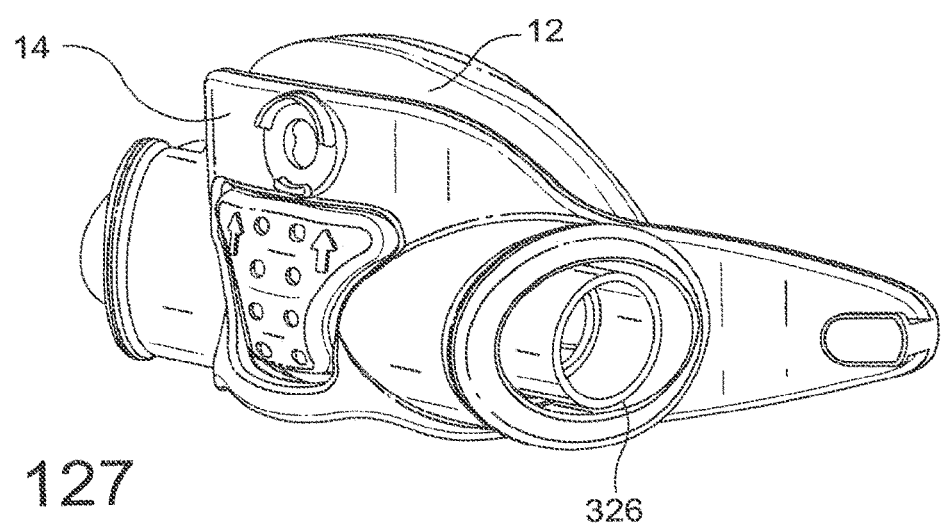

Referring to FIGS. 123-128, a patient interface system according to another sample embodiment may comprise a cushion 12 having at the vent region thickened portion 145 of the base wall 52 to increase the length of the vent holes 78, 79. The vent holes 78, 79 may have an aspect ratio of 1.6/5.0, or 0.32. The thickened portion 145 of the cushion 12 also aids in aligning the cushion with the frame 14 as the thickened portion 145 of the cushion 12 extends past the bridge 120 and the crossbar 48 of the frame 14, as shown in FIGS. 126-128. Referring to FIGS. 123 and 124, the vent apertures or holes 78, 79 may be configured to provide a vent flow within 30.7 to 41.0 L/min at 12 cm of $H_2O$. Referring to FIG. 126, the cushion 12 may include a parting line 13 which separates the sealing area from the remainder of the cushion. The sealing area of the cushion may be polished to improve the sealing function of the cushion with the patient's face.

1.3.5 Connection between Cushion and Air Delivery Tube

Figure 15:
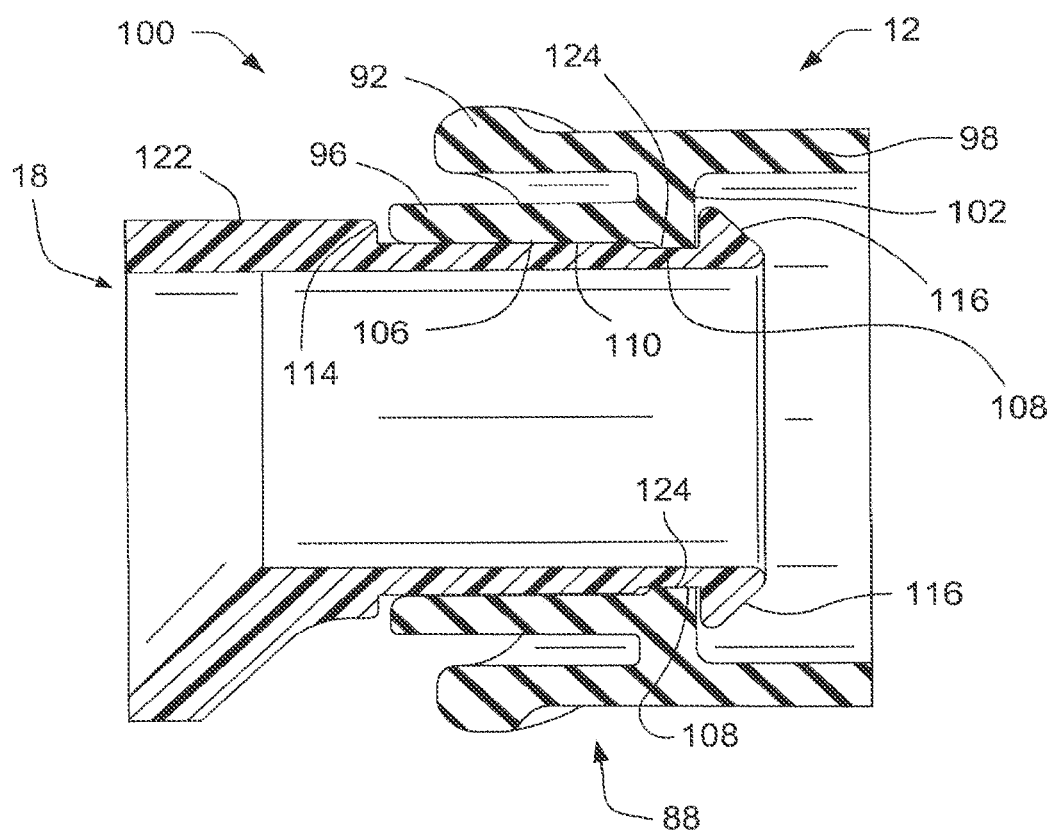
FIG. 15 schematically depicts a cross-sectional view of a connection between the elbow of FIGS. 11-14 and the patient interface, or cushion, of FIGS. 3-7.
Figure 16:
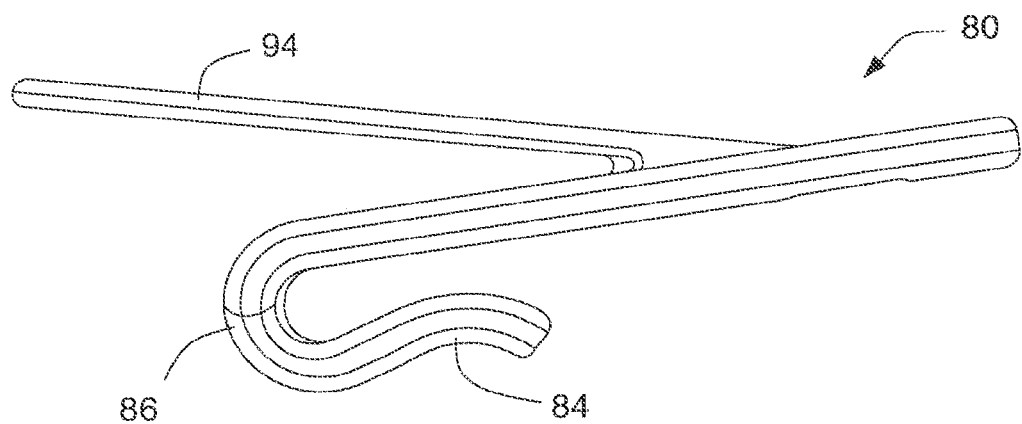
FIGS. 16-18 schematically depict a quick release buckle according to an embodiment of the technology.

Advantageously, the mask 10 also provides a connection arrangement 100 (FIGS. 20 and 21) between the cushion 12 and air delivery tube 22 that at least partially decouples movement of the tube 22 from the cushion 12 and support structure 14. This means that lateral and some axial movement of the tube 22 (e.g., from tube drag) and tube rotation do not substantially move the cushion 12. Subsequently, movement of the cushion 12 and support structure, or frame, 14 on the patient's face due to tube drag is reduced. This serves to reduce disturbance to the patient, particularly as it aids maintenance of the cushion seal with the patient's face. The connection arrangement 100 comprises two parts: the cylindrical protrusions 88 and the elbow 18, as shown in FIGS. 15, 20 and 21.

The cushion 12 has a short, hollow cylindrical protrusion 88 extending from each of its lateral sides 36 for receiving an elbow 18 or plug 20. The hollow 90 of each protrusion 88 is in fluid communication with the air chamber 26 of the cushion 12. In this case, the dimensions of the hollows 90 are the same such that the elbow 18 and plug 20 can be fitted into either hollow 90. This allows the elbow 18 and air delivery tube 2 to connect to the most convenient side of the mask 10. With such an arrangement, the patient may lie on their stomach with their head facing to one side without occluding the air delivery tube by placing the plug 20 in the hollow 90 on the side of the mask corresponding to the side the patient's head is lying on. Additionally, a line of sight to the patient's nose is possible as there is no elbow or air delivery tube positioned on the front of the mask as with other breathing masks. If the cushion is not water clear and thereby prevents the clinician from seeing the patient's nose, it is still possible to see if the patient is in distress as the mouth is uncovered i.e. the lips may begin to turn blue.

Figure 9:
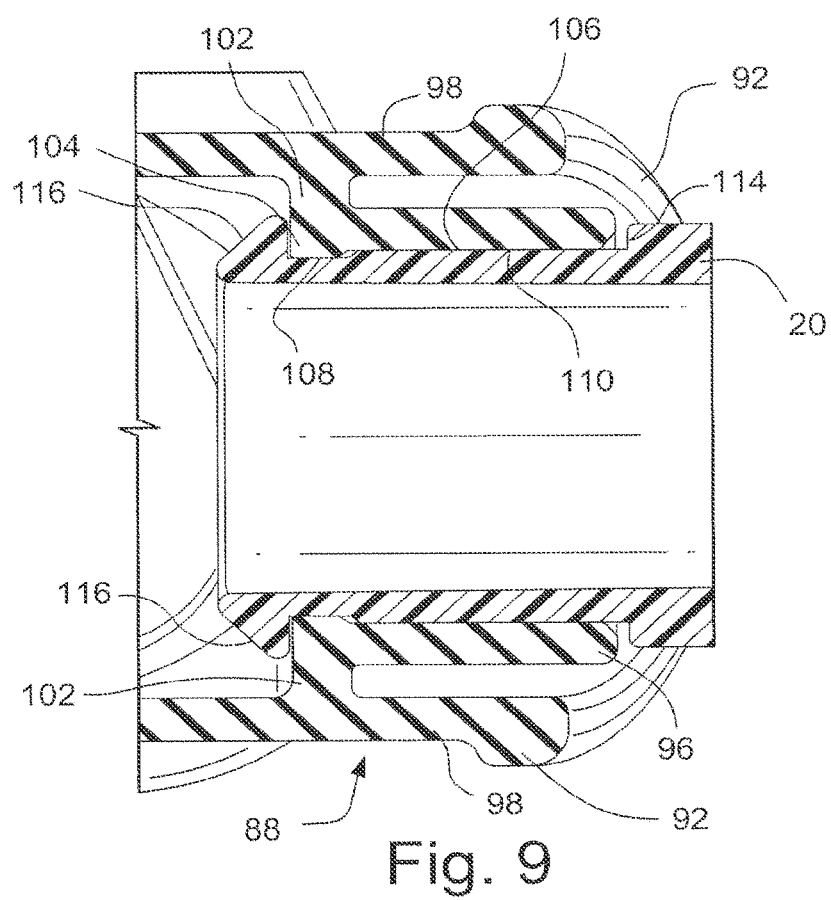
FIG. 9 schematically depicts a cross-sectional view of a connection of a plug, and the patient interface, or cushion, of the respiratory mask assembly of FIG. 1.

The elbow 18 is releasably and rotatably connected to the cushion 12 and the air delivery tube 2. Each cylindrical protrusion 88 comprises an inner cylinder 96 and an outer cylinder 98 that are substantially concentric and joined at an end closest to the support structure 14 by a thin flexible cylindrical membrane 102, as shown in FIGS. 9 and 10. The desired and suitable dimension ranges for the inner and outer cylinders 96 and 98 may be as provided in International Application PCT/AU2008/000270 (WO 2008/106716 A1), the entire contents of which are incorporated herein by reference. It should be appreciated that the dimensions may be otherwise.

By virtue of the flexibility and elastic properties of the thin membrane 102, the inner cylinder 96 can rotate laterally with respect to the outer cylinder 98, about the thin membrane 102, by a small angle, and also move axially with respect to the outer cylinder 98 by a small distance. In the depicted sample embodiment, the maximum angle of rotation and the axial displacement may be as described in International Application PCT/AU2008/000270 (WO 2008/106716 A1), the entire contents of which are incorporated herein by reference. It should be appreciated that the angle and displacement may be otherwise. Thus, the inner cylinder 96 is substantially decoupled from the outer cylinder 98. In the depicted sample embodiment, the thin membrane 102 is made from silicone, but it should be appreciated that it could be made from any other suitable material that is flexible and biocompatible.

To aid in further decoupling tube drag, a highly flexible tube may be attached to elbow 18. For example, a tube as disclosed in US patent application US 2009/0078259, the entire contents of which are incorporated herein by reference.

The outer diameter of the elbow 18 forms a snug fit with the inner diameter of the inner cylinder 96. The inner cylinder 96 includes a circumferential rib 104 on its inner surface 106 (see FIG. 9) that is configured to mate with a cooperating circumferential groove 108 disposed on the outer surface 110 of the elbow 18. Accordingly, when the elbow 18 is inserted into the soft inner cylinder 96, the rib 104 interlocks with the groove 108 to axially fix the elbow 18 in the inner cylinder 96. By virtue of the fact that the inner cylinder 96 is substantially decoupled from the outer cylinder 98, the elbow 18 and air delivery tube 2 are substantially decoupled from the cushion 12. In another sample embodiment, the rib 104 and groove 108 arrangement could be reversed (i.e. rib 104 on elbow 18, groove 108 on inner cylinder 96).

The free end of the outer cylinder 98 is angled by an angle A towards the center of the front side of the mask 10 so that a portion of the inner cylinder 96 extends beyond the end of the outer cylinder 98. This allows the inner cylinder 96 to be laterally displaced towards the front side of the mask 10 to a greater degree since it is not blocked by the outer cylinder 98 to the same extent. This provides better decoupling of the tube 2 from the cushion 12. Another advantage is that this angle provides the mask with better aesthetics, in that the mask appears more streamlined to the face. The angle may be as disclosed in International Application PCT/AU2008/000270 (WO 2008/106716 A1), the entire contents of which are incorporated herein by reference. It should be appreciated that the angle may be otherwise.

The decoupling mechanism is also supported by the frame 14 since the outer cylinders 98 of the cushion 12 are snugly seated in respective, relatively cylinders 112 provided in the support structure 14.

1.3.6 Assembly of Cushion to Frame and Elbow

Figure 8:
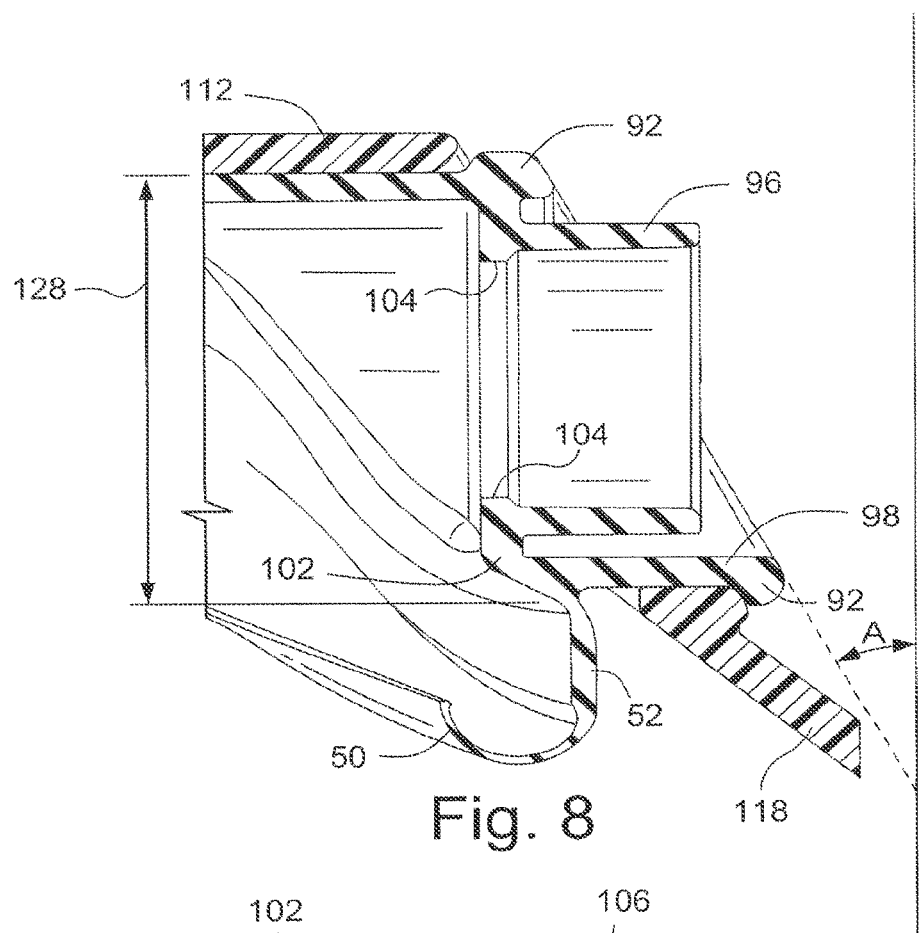
FIG. 8 schematically depicts a cross-sectional view of a connection of the support structure, or frame, and the patient interface, or cushion, of the respiratory mask assembly of FIG. 1.

The cushion 12 is assembled to the frame 14 by inserting each short, hollow cylindrical protrusion 88 through the respective cylinder 112 of the frame 14 as shown in FIG. 8. Each short, hollow cylindrical protrusion 88 comprises the inner cylinder 96 and the outer cylinder 98, which are connected by the thin membrane 102. The cushion 12 has a bearing diameter 128 that is chosen to provide a balance between ease of assembly of the cushion 12 with the frame 14 and restricted rotational movement of the cushion 12 when assembled into the cylinders 112 of the frame 14.

The elbow 18 is assembled to the cushion 12 by inserting the elbow 18 into the inner cylinder 96 as shown in FIG. 15. The outer surface 110 of the elbow 18 comprises a circumferential groove 108 that receives a circumferential rib 104 (FIG. 8) of the membrane 102 of the cushion 12. The circumferential rib 104 and the circumferential groove 108 provide an interference fit that seals the connection between the elbow 18 and the cushion 12. The inner surface 106 of the inner cylinder 96 may also engage the outer surface 110 of the elbow 18 to provide a sealing surface as shown in FIG. 15.

Lug or bead 92 on cushion 12 may be adapted to engage with the frame 14 to maintain the cushion and frame assembly.

1.3.7 Valve

Figure 38:
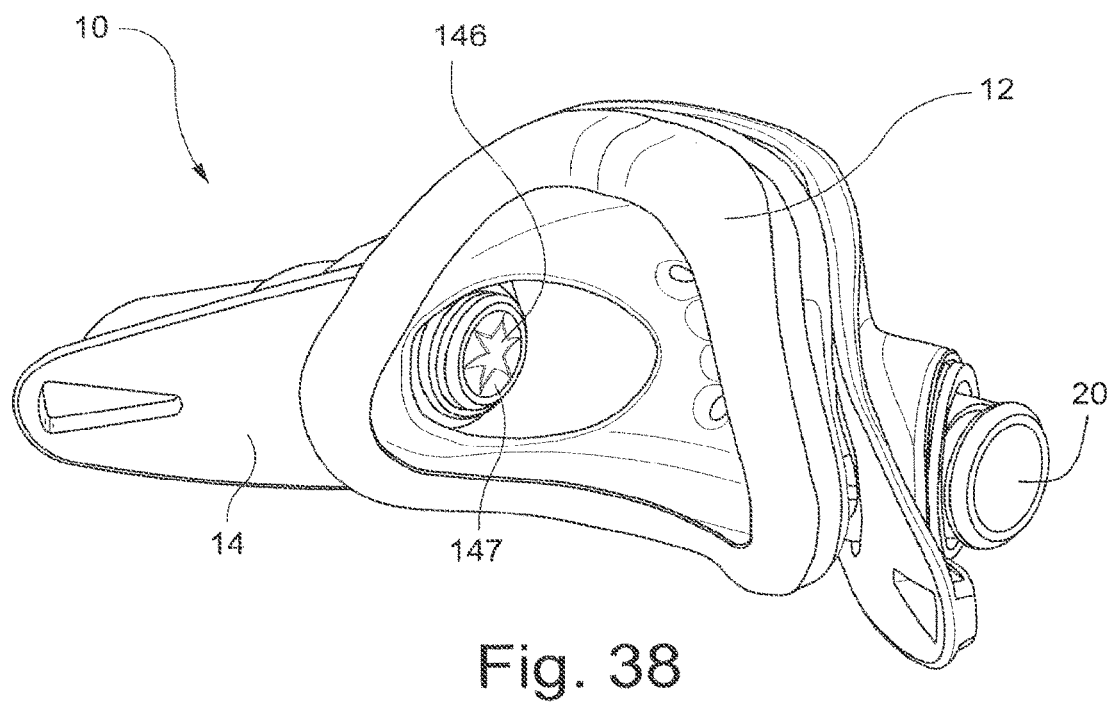
FIG. 38 schematically depicts a rear perspective view of the respiratory mask assembly of FIG. 37 with open valve flaps.
Figure 39:
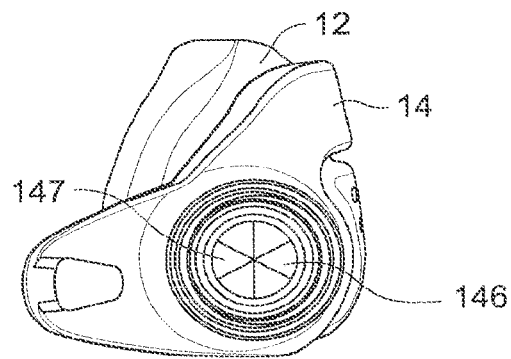
FIG. 39 schematically depicts a side view of the respiratory mask assembly of FIG. 37 with closed valve flaps.
Figure 40:
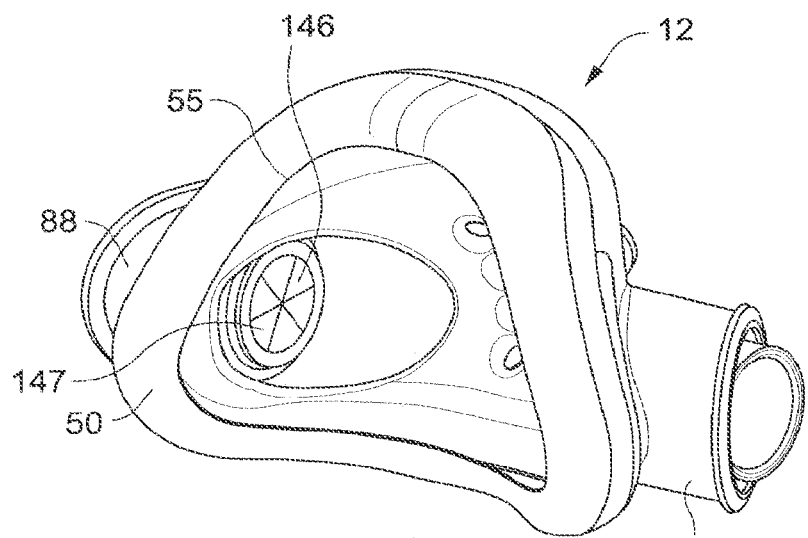
FIG. 40 schematically depicts a rear perspective view of the cushion of the respiratory mask assembly of FIG. 37 with closed valve flaps.

Referring to FIGS. 37-40, a cushion and respiratory mask assembly according to another sample embodiment includes a valve 146 in each inner cylinder 96 of each short, hollow cylindrical protrusion 88 of the cushion. The valve 146 may be integrally formed with the cushion 12 and include a plurality of individual flaps 147 that are "closed" (in contact with each other) to seal the inner cylinder 96 when a positive pressure (i.e. pressurized flow of breathable gas) is applied to the mask. As shown in FIG. 38, the flaps 147 are "open" when the elbow 18 is inserted into the inner cylinder 96 to deliver the flow of gas. As shown in the drawings, each valve 146 includes six flaps 147. It should be appreciated that the valves may include any number of flaps.

The provision of the valves 146 in the cushion eliminates the need for a plug to seal the side of the cushion opposite the elbow, thus reducing parts, inventory, and costs. It also reduces the need for small components (such as a plug) that a child could choke on. The provision of the valves 146 also assists in assembling the mask and reduces assembly errors. For example, machine vision equipment configured to detect correct assembly of masks on a production assembly line may incorrectly conclude that a plug is properly inserted when the plug is improperly inserted into the cushion. The provision of the valves 146 in the cushion 12 eliminates such errors.

Figure 41:
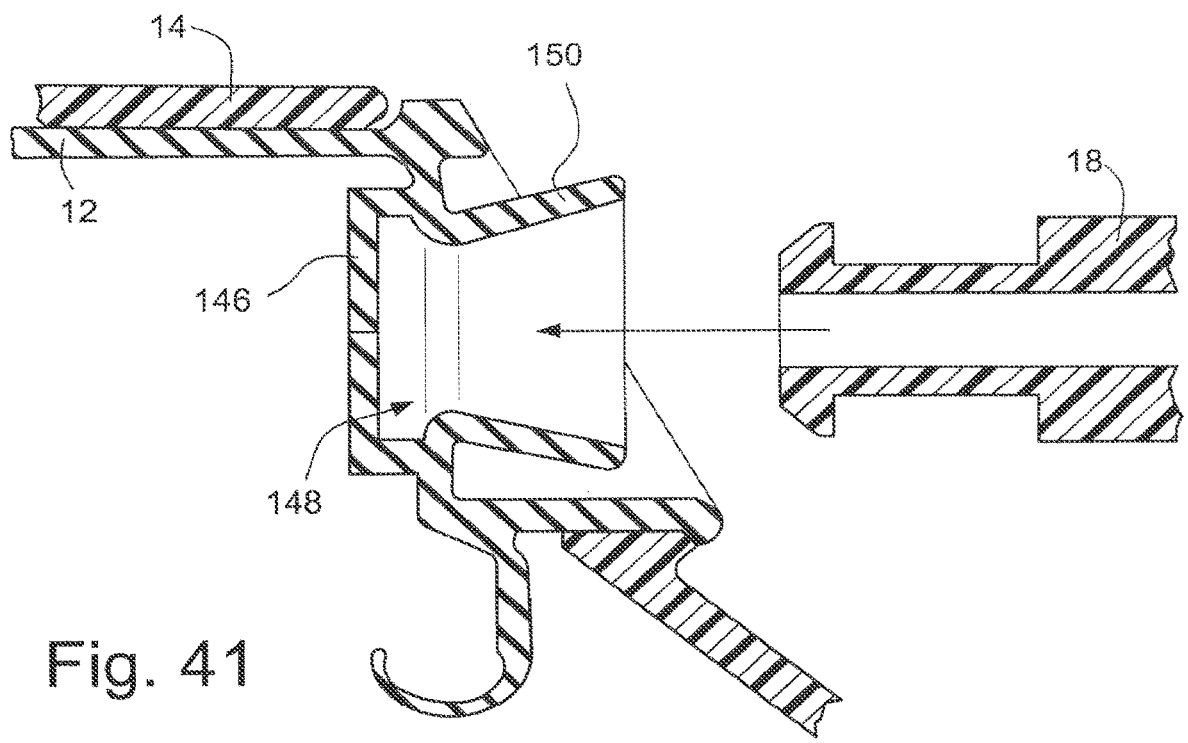
FIG. 41 schematically depicts a cross-sectional view of a cushion and an elbow according to another sample embodiment of the technology.
Figure 42:
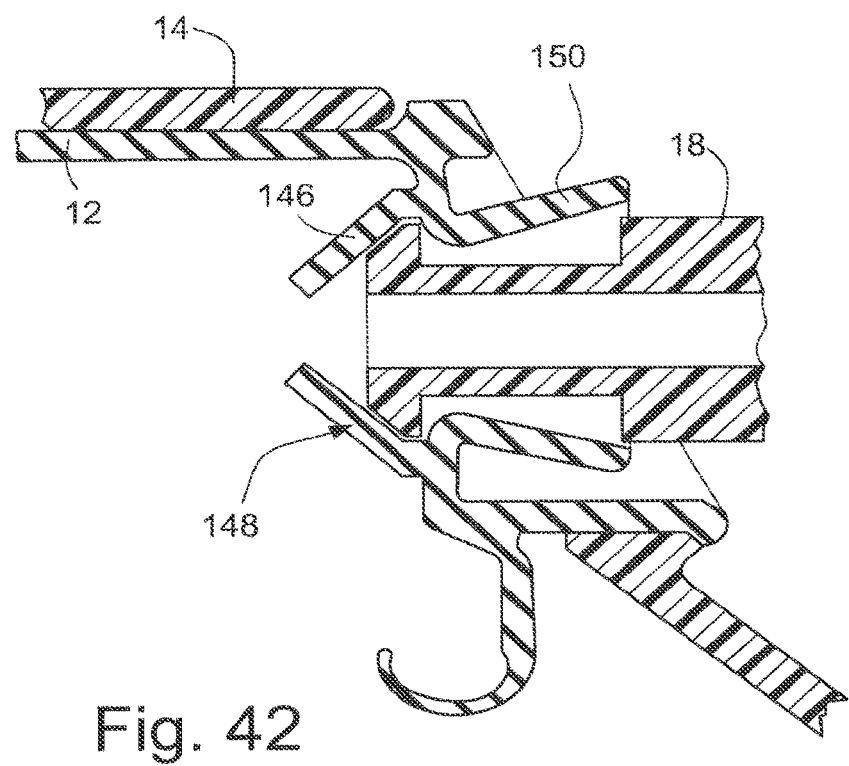
FIG. 42 schematically depicts a cross-sectional view of the cushion of FIG. 41 with the elbow attached.

Referring to FIGS. 41 and 42, the inner cylinder of the hollow protrusion of the cushion 12 may be provided as a conical inner cylinder 150. The tapered opening of the conical cylinder 150 aids insertion of the elbow 18 or plug 20 into the cushion 12. A recess 148 may be provided between the flaps 147 of the valve 146 and the conical cylinder 150 to provide a seal at the contacting surfaces of the elbow 18 and the flaps 147 as shown in FIG. 42.

Figure 43:
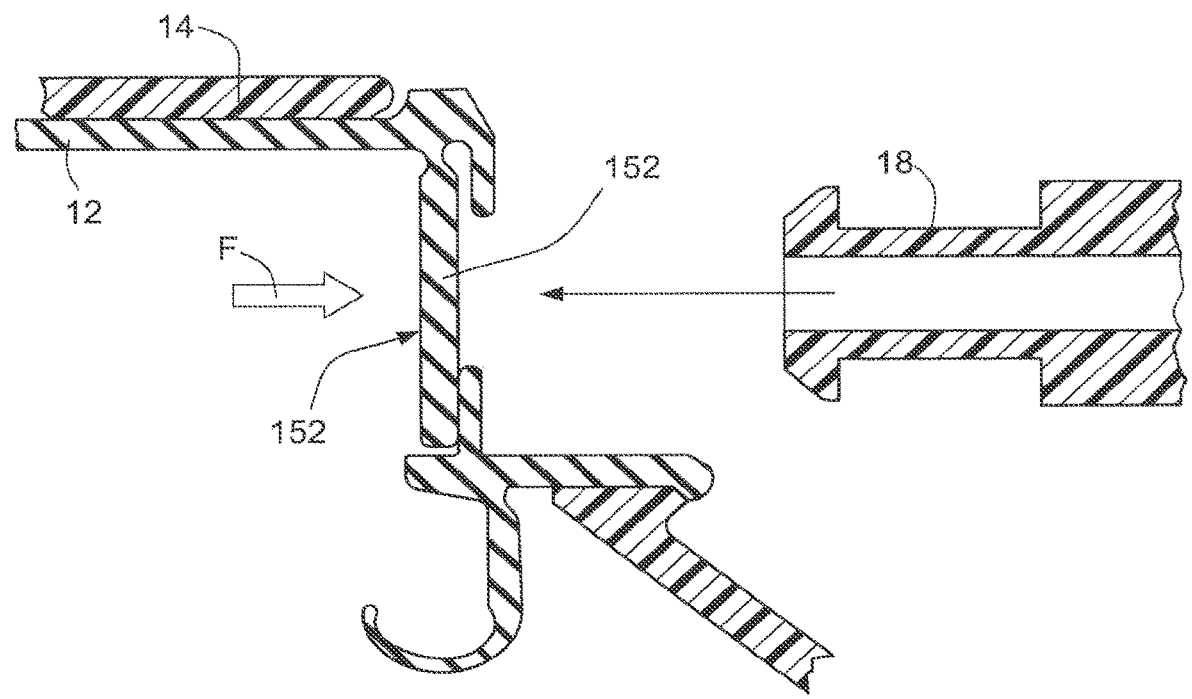
FIG. 43 schematically depicts a cross-sectional view of a cushion and an elbow according to another sample embodiment of the technology.
Figure 44:
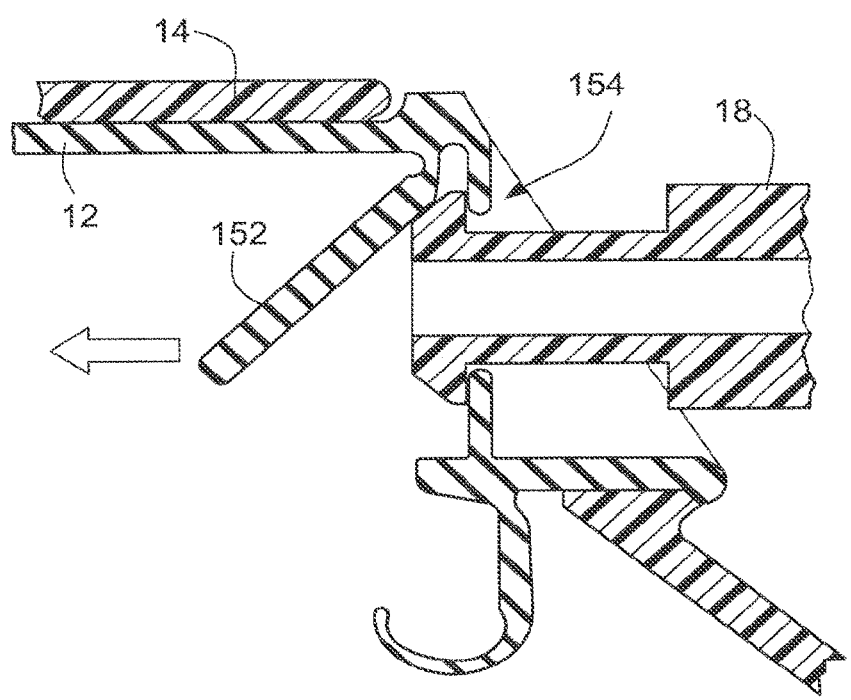
FIG. 44 schematically depicts a cross-sectional view of the cushion of FIG. 43 with the elbow attached.

Referring to FIGS. 43 and 44, according to another sample embodiment the valve 152 may be similar to an anti-asphyxia valve (AAV) that is sealed at pressure by the flow F of breathable gas in the cushion. A lip seal 154 may be provided to seal the end of the elbow 18 when the elbow 18 is inserted into the cushion.

1.3.8 Plug

The cushion 12 has a short, hollow cylindrical protrusion 88 extending from each of its lateral sides 36 for receiving an elbow 18 on one side and a plug 20 on the other side. As shown in FIG. 1, the plug 20 may have a handle 21 that is adapted to be gripped by a user, to be pulled out of or pressed into one of the cylindrical protrusions 88 of the cushion 12.

As illustrated in FIG. 9, the outer surface 110 of the plug 20 comprises a circumferential groove 108 that receives the circumferential rib 104 of the thin membrane 102 of the cushion 12. The circumferential rib 104 and the circumferential groove 108 provide an interference fit that seals the connection between the plug 20 and the cushion 12. The inner surface 106 of the inner cylinder 96 may also engage the outer surface 110 of the plug 20 to provide a sealing surface.

The plug 20 may include a beveled flange 116 that is configured to aid insertion of the plug 20 into the short, hollow cylindrical protrusion 88 of the cushion 12. As shown in FIG. 9, a circumferential edge 114 is provided between the outer sealing surface 110 of the plug 20 and the outer surface 122 of the plug 20. The inner cylinder 96 of the short, hollow cylindrical protrusion 88 of the cushion 12 is captured between the beveled flange 116 and the circumferential edge 114 to provide secure attachment of the plug 20 to the cushion 12. Preferably, the plug is more easily gripped by an adult than by a child.

Figure 71:
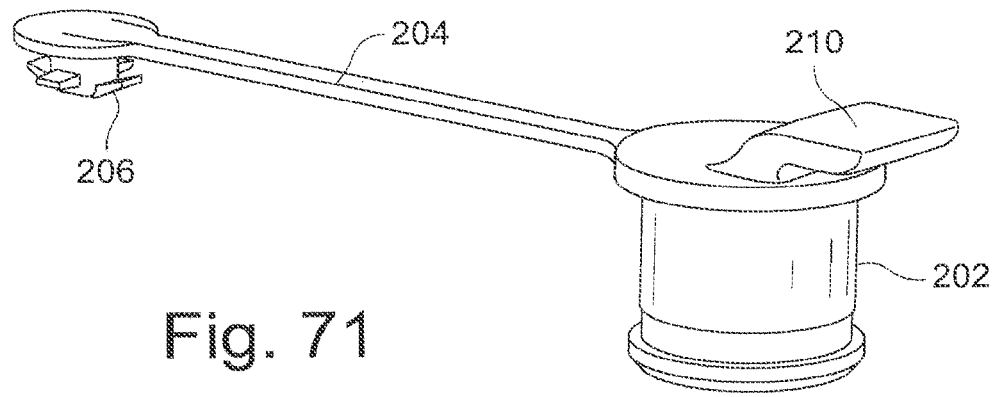
FIG. 71 schematically depicts a tether with retention lugs and a handle according to another sample embodiment of the technology.

Referring to FIG. 71, in an alternative sample embodiment of the present technology, the plug 202 may include a handle 210 to assist in inserting and removing the plug from the cushion of the patient interface. The handle 210 may extend from a top surface of the plug 202, and be adapted for gripping by a user. For example, the handle 210 may extend a predetermined distance from an end of the plug 202 and be shaped for ease of gripping by the user.

The plug 202 is configured to seal to the cushion with substantially no leak. The plug 202 is adequately retained to the cushion at pressures up to, for example, about 40 cm $H_2O$. The plug 202 provides ease of assembly and disassembly to and from the left and right side of the cushion, depending on which side the patient connects to the air delivery tube.

Figure 45:
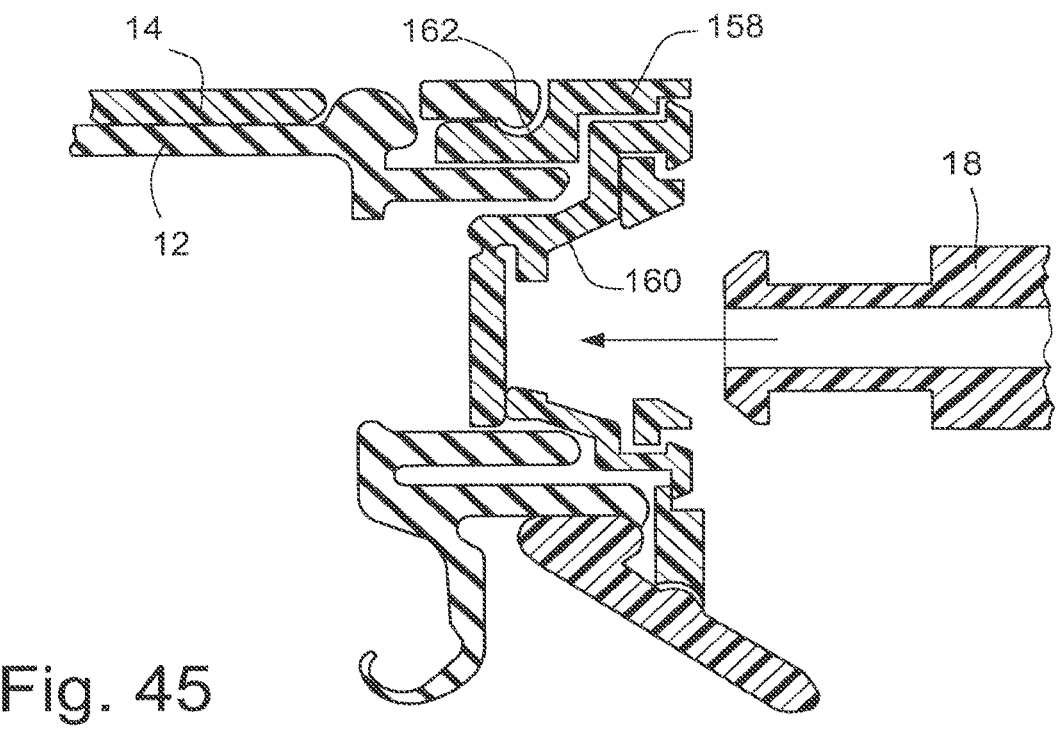
FIG. 45 schematically depicts a cross-sectional view of a cushion, a cap including a valve and an elbow according to another sample embodiment of the technology.
Figure 46:
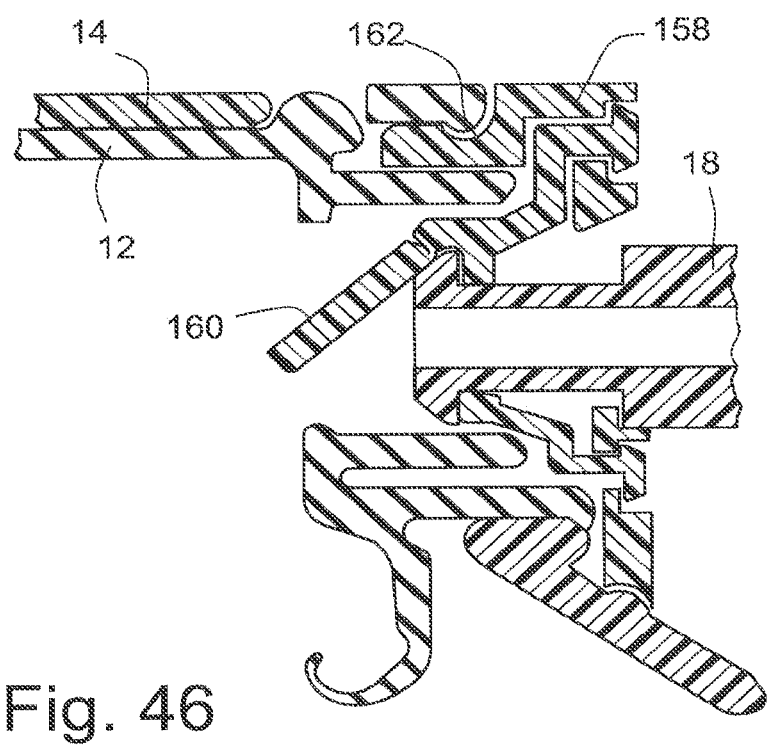
FIG. 46 schematically depicts a cross-sectional view of the cushion and the cap of FIG. 45 with the elbow attached to the cap.
Figure 47:
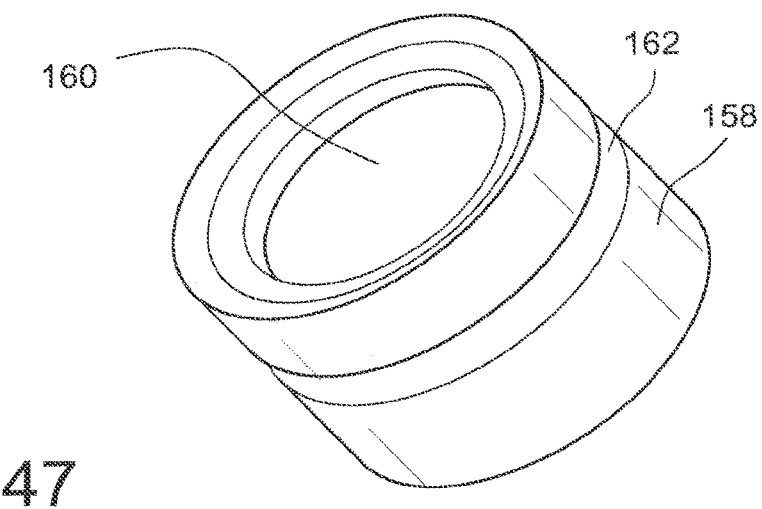
FIG. 47 schematically depicts a perspective view of the cap of FIG. 45.
Figure 48:
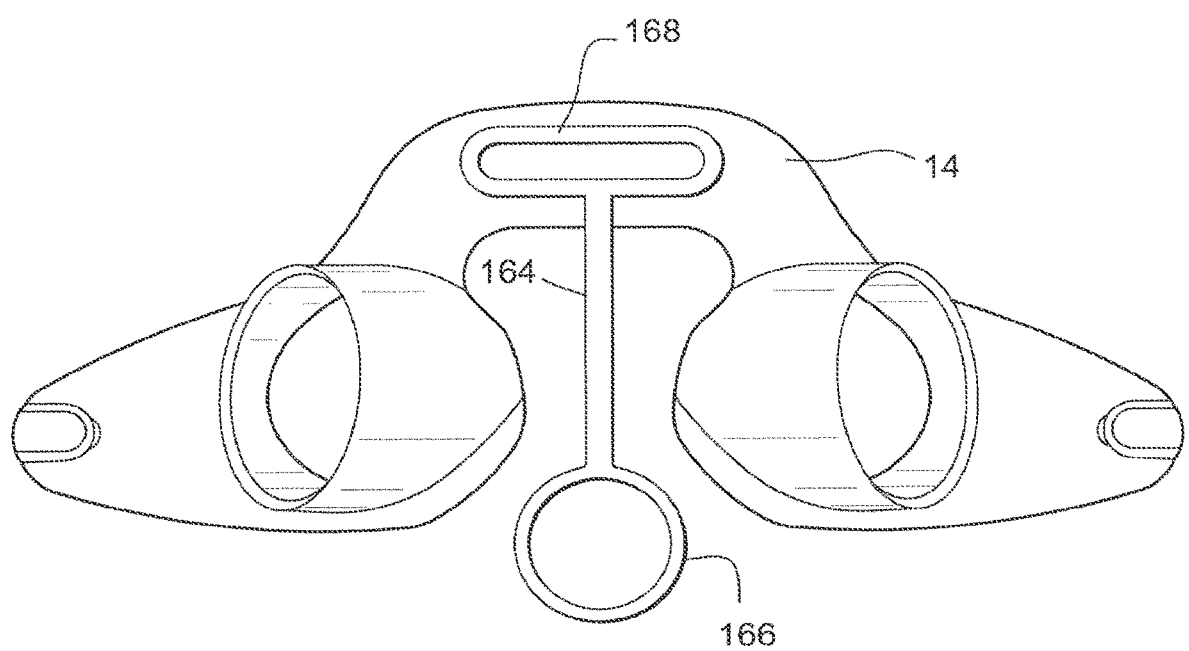
FIG. 48 schematically depicts a front view of a frame, or support structure, and a tether according to a sample embodiment of the technology.
Figure 49:
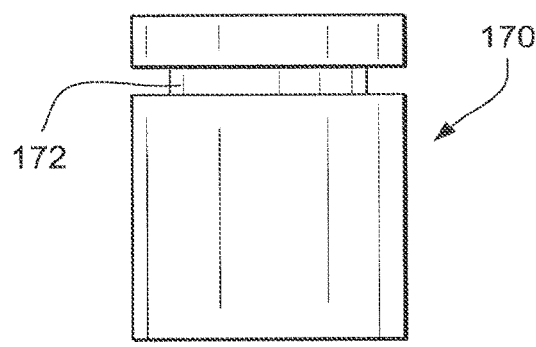
FIGS. 49 and 50 schematically depict a plug adapted to connect to the tether of FIG. 48.
Figure 50:
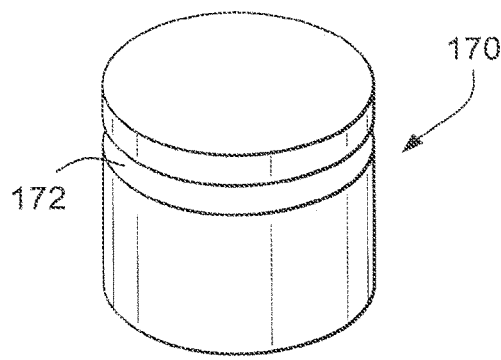

Referring to FIGS. 45-47, a cap 158 may be provided with a valve 160. As shown in FIGS. 45 and 46, the valve 160 may be similar to the valve 152 shown in FIGS. 43 and 44. It should be appreciated that the valve 160 may be similar to the valve 146 shown in FIGS. 37-42. The cap 158 may be preassembled with the valve 160 and the cap may then be inserted into the cushion 12. The cap 158 may include a groove 162 configured to snap fit the cap 158 into the frame 14 and prevent the cap 158 from being inserted too far into the hollow cylindrical protrusions 88 of the cushion 12. The cap 158 could also be molded into the frame 148, for example by a living hinge. The cap 158 is adapted to receive and retain the elbow 18, at which time the valve 160 is opened.

1.3.8.1 Tether

Figure 51:
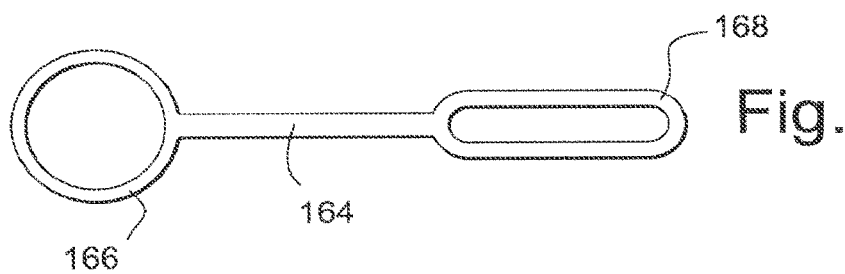
FIG. 51 schematically depicts a tether according to another sample embodiment of the technology.

Referring to FIGS. 48-54, an alternative plug or cap 170 adapted to connect to a tether may include a groove 172 in its outer surface. A tether 164 may include a ring 166 at one end configured to be received in the groove 172 and a connector 168 at an opposite end for connection of the tether 164 to the frame 14. An alternate configuration of the connector 168 is shown in FIG. 51. The groove 172 allows rotation of the cap 170 with respect to the ring 166 for easier orientation of the cap 170. The tether 164 may be formed of, for example, PTFE, nylon, polycarbonate.

Figure 52:
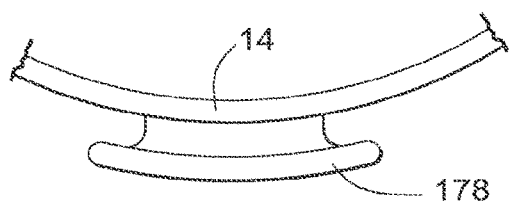
FIG. 52 schematically depicts a connection arrangement for a tether to the frame of the respiratory mask assembly according to a sample embodiment of the technology.
Figure 53:
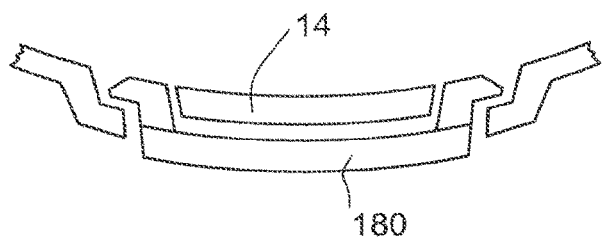
FIG. 53 schematically depicts a connection arrangement for a tether according to another sample embodiment of the technology.
Figure 54:
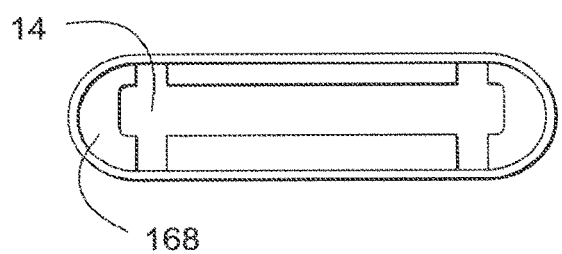
FIG. 54 schematically depicts a connection arrangement for a tether according to still another sample embodiment of the technology.
Figure 55:
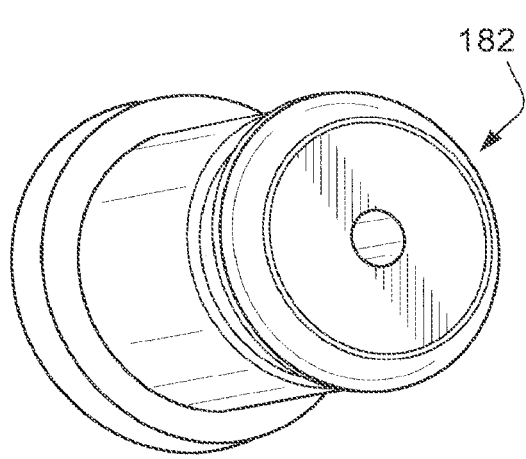
FIGS. 55 and 56 schematically depict perspective views of a port for use with a respirator mask assembly according to a sample embodiment of the technology.
Figure 56:
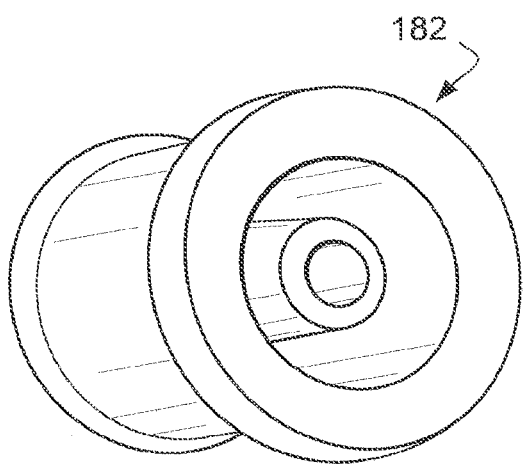

FIG. 52 depicts a connecting structure 178 provided on the frame 14 that is configured to receive the connector 168 of the tether 164 to connect the tether 164 to the frame 14. FIG. 53 depicts a connector 180 of the tether 164 according to another sample embodiment that snap fits into place on the frame 14 to connect the tether 164 to the frame. FIG. 54 depicts the connector 168 of the tether 164 molded into the frame 14.

Figure 69:
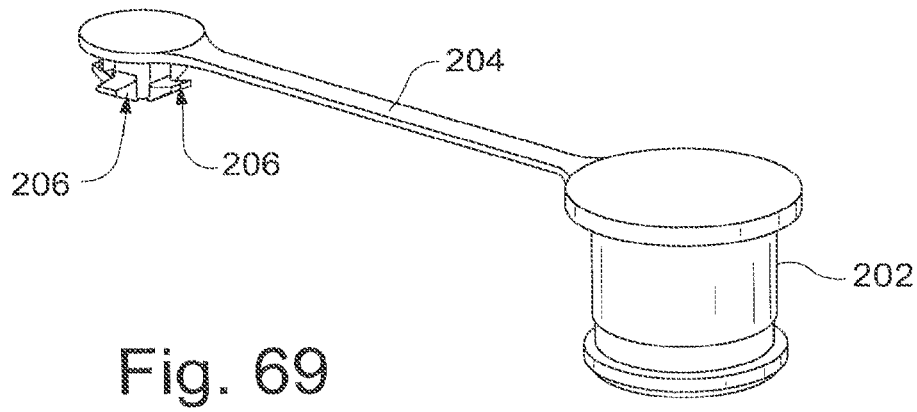
FIG. 69 schematically depicts a tether with retention lugs according to another sample embodiment of the technology.
Figure 70:
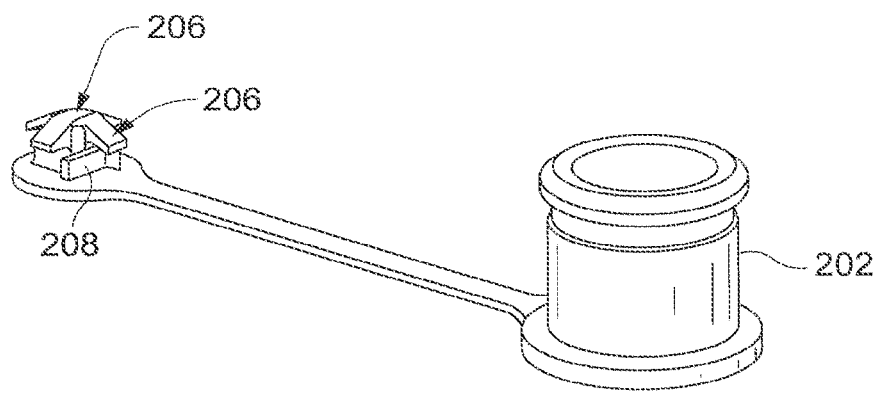
FIG. 70 schematically depicts a tether with retention lugs and a rib according to another sample embodiment of the technology.

Referring to FIGS. 69 and 70, a plug 202 for the cushion may comprise an integrally formed tether 204. The end of the tether 204 may include retention lugs 206 for securing the plug 202 to the frame. As shown in FIGS. 73-77, the retention lugs 206 are inserted through an aperture 211 in the frame 14 of the patient interface to permanently retain the plug 202 to the frame 14.

Referring back to FIG. 70, a rib 208 may be provided adjacent the retention lugs 206. As shown in FIG. 72A, the frame 14 of the patient interface may include a guide or cap 212 to prevent the tether 204 from being rotated upwards past the horizontal end to prevent the plug 202 from interfering with the user's eyes. The rib 208 is configured to locate the end of the tether 204 in the aperture 211 of frame 14 so that the tether does not move laterally when positioned within the aperture 211.

As shown in FIG. 72B, a stopper 213 may be included on the frame 14. The stopper 213 prevents the tether 204 from being positioned downwards to prevent the tether 204 from being positioned over the array of vent holes 74, 76, which could cause noise from the vented gases hitting the tether 204.

Figure 73:
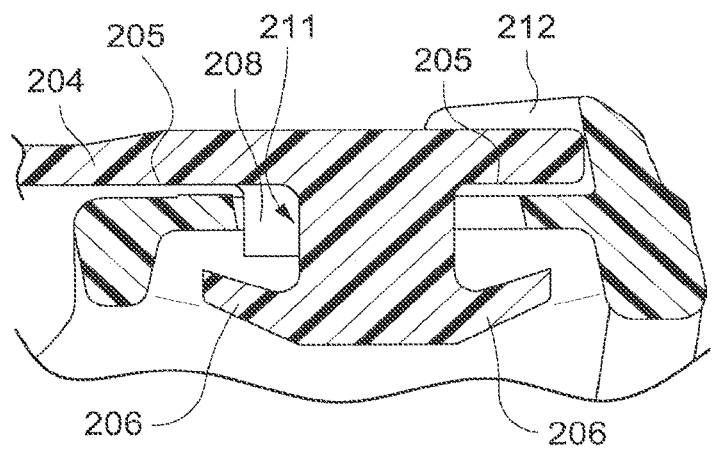
FIGS. 73 and 74 are cross-sectional views illustrating retention lugs that connect the tether to the frame according to other sample embodiments of the technology.
Figure 74:
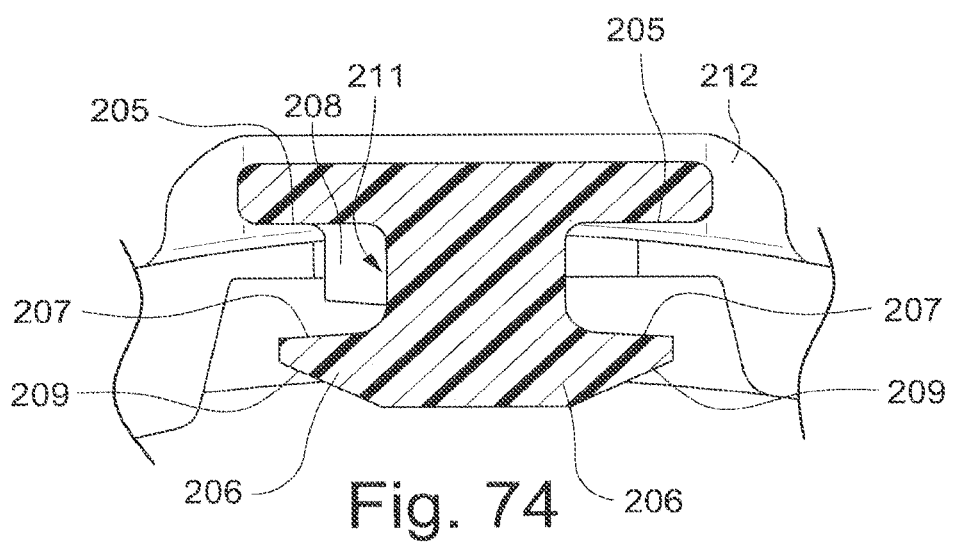
Figure 75:
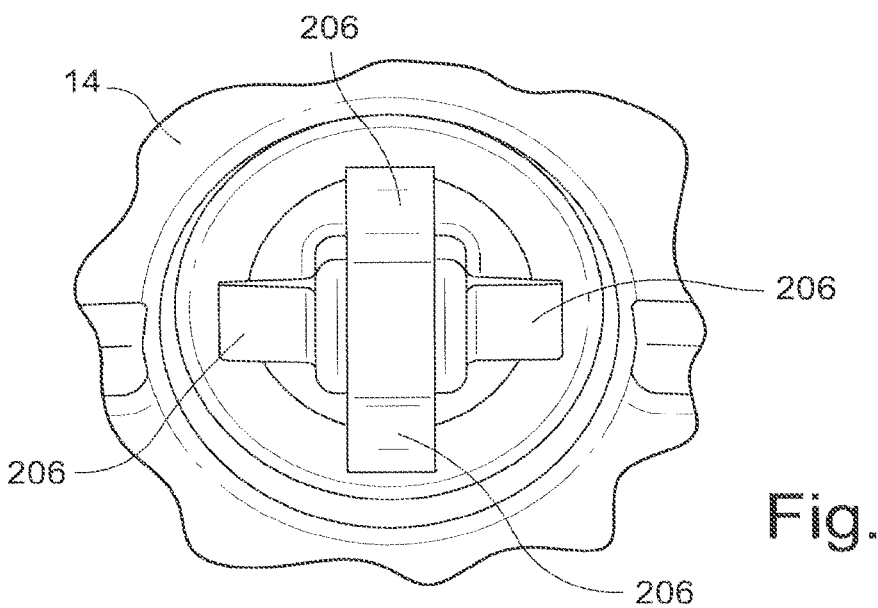
FIG. 75 schematically depicts a partial bottom view of the retention lugs of the frame according to another sample embodiment of the technology.
Figure 76:
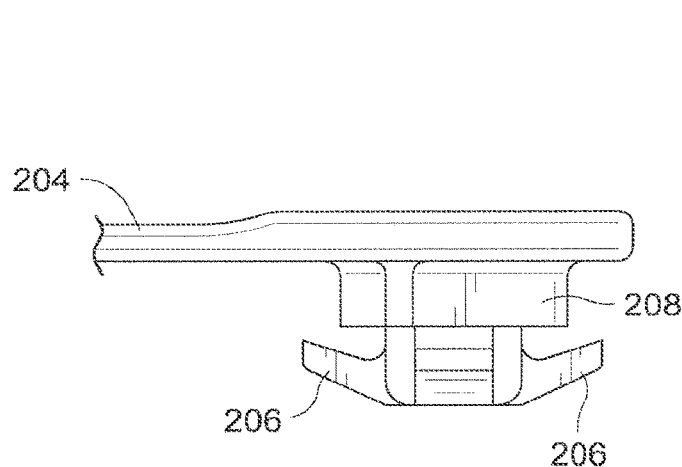
FIG. 76 schematically depicts a side view of the retention lugs of the tether.
Figure 77:
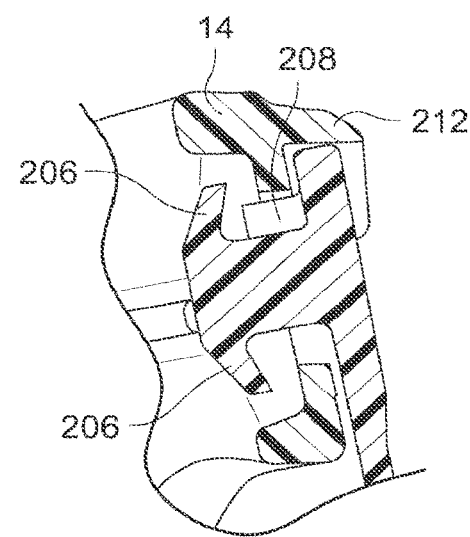
FIG. 77 is a cross-sectional view illustrating the retention lugs connected to the frame according to another sample embodiment of the technology.

Referring to FIGS. 73-77, the retention lugs 206 may be formed to provide a one way fit of the plug to the frame 14 of the patient interface. The lugs 206 may be angled upwardly as shown in FIG. 73 with respect to the tether 204. Alternatively, the lugs 206 may have a first surface facing 207 facing the lower surface of the tether 204, and a second surface 209 facing away from the lower surface of the tether 204, where the first surface 207 is substantially parallel to the lower surface 205 of the tether 204, and the second surface 209 is angled with respect to the lower surface 205 of the tether, as shown in FIG. 74. It should be appreciated that other permanent attachment or one way fit mechanisms may be provided for securing the plug 202 to the frame 14 via the tether 204.

The plug 202 is adapted to be permanently retained to the frame 14 by the tether 204 and the retention lugs 206 so as to not pose a choking hazard for a child.

The plug 202, the tether 204, the retention lugs 206 and the rib 208 may be integrally formed of, for example, polypropylene, nylon, polycarbonate, polyurethane, or silicone. It should be appreciated that other materials may be used to form the plug, tether, retention lugs, and rib.

Figure 92:
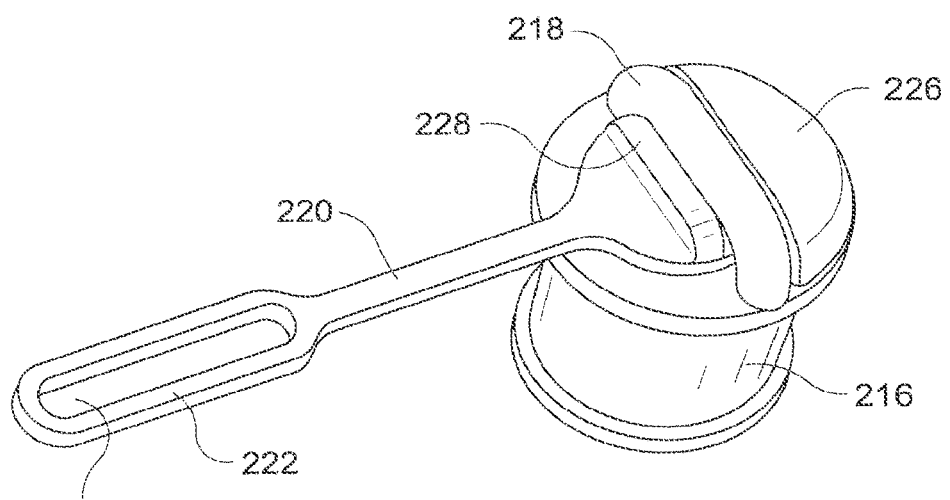
FIG. 92 schematically depicts a perspective view of a plug connected to a tether according to another sample embodiment of the technology.
Figure 93:
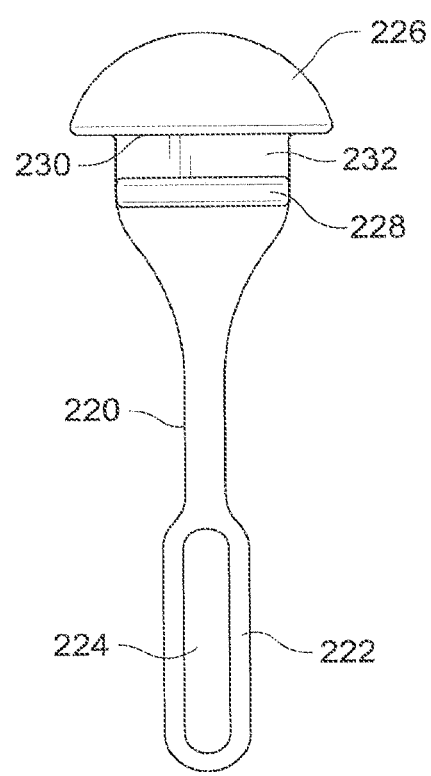
FIG. 93 schematically depicts the tether of FIG. 92.
Figure 94:
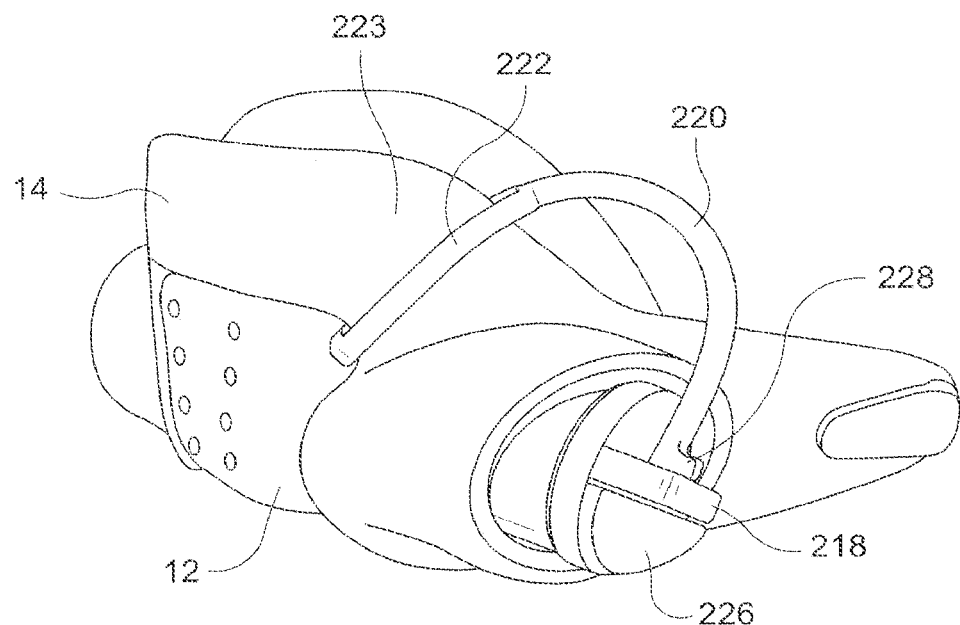
FIG. 94 schematically depicts a perspective view of connection of a plug to a frame of a mask assembly according to another sample embodiment of the technology.

Referring to FIGS. 92-94, a tether 220 may be connected to a plug 216. The plug 216 may include a handle 218, and the tether 220 may be adapted to connect to the handle 216. The tether 220 may include a recess 232, formed between flanges 228 and 230, and a rounded portion 226. The recess 232 is adapted to receive the handle 218 of the plug 216, with the flanges 228 and 230 sandwiching the handle 218. The rounded portion 226 is adapted to conform to the rounded side portion of the plug 216.

The tether 220 may also include a connector 222 having an aperture 224, the connector being adapted to connect to the frame 14. The aperture 222 is configured to receive the frame 14, so the tether 220 is connected to the frame, with the plug 216 connected to the tether 220. When the plug 216 is removed from the cushion 12, the tether 220 will hold the plug 216 so that the plug 216 does not become lost or a choke hazard.

The tether 220 may be formed from molded silicone that is stretchable. The loop of the tether 220 that contains the aperture 224 may be stretched to fit over the wider part of the frame 14, and allowed to be retained on the bridge portion 223 of the frame 14. When plug 216 is removed from the cushion 12 while connected to the tether 220, the plug will not be lost because it is connected to the frame 14 by the tether 220.

Figure 95:
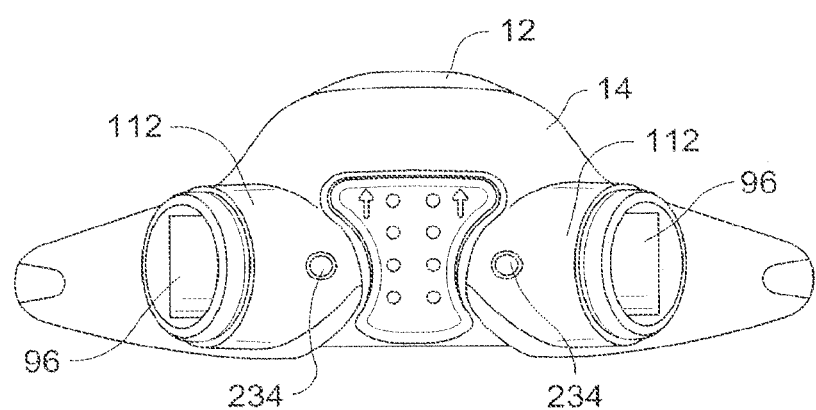
FIG. 95 schematically depicts a front view of a frame and cushion of a mask assembly according to another sample embodiment of the technology.

Referring to FIGS. 95 and 96, the frame 14 may include an aperture 234 on the cylinders 112, adapted to connect tether 238 to the frame 14. The tether 238 may include a connector in the form of a protrusion 240 adapted to fit within the aperture 234. The protrusion 240 may be adapted to be permanently held within the aperture 234, or may be adapted to be temporarily held within the aperture 234, such as through the use of a retaining mechanism. When the plug 236 is removed from the cylinder 96 of the cushion 12, the tether 238 connects the plug 236 to the frame 14. The protrusion 240 may be adapted to turn within the aperture 234 so that the plug 236 and the tether 238 may be pushed to connect in either side of the cushion.

One aperture 234 may be located on each cylinder of the frame 14. Where the protrusion 240 is removable from the aperture 234, the tether 238 and the plug 236 may be moved between either side of the frame 12. Where the protrusion 240 is adapted to be permanently held within the aperture 234, the frame may be provided with two tethers 238, each connected to a plug 236. Either one of the plugs 236 could be connected within the corresponding cylinder 96 of the cushion 12, while the other cylinder 96 would be connected to the elbow.

Referring to FIGS. 97-99, plug 248 may be connected to tether 250. Tether 250 may include connector 252, which is adapted to be received in aperture 242. Connector 252 includes a wide portion 254, and aperture 242 includes a narrow portion 246 and a wide portion 244. The wide portion 254 of the connector 252 may be received by the wide portion 244 of the aperture 242, and the wide portion 254 of the connector 252 pushed below a lower surface of the cylinder 112, and the connector 252 may be positioned so that the wide portion 254 is below the narrow portion 246 of the aperture 242, to retain the tether 250 to the cylinder 112 of the frame 14. The tether 250 may be stretchable to allow the connector 252 to stretch to reach the wide portion 244 of the aperture 242.

Figure 100:
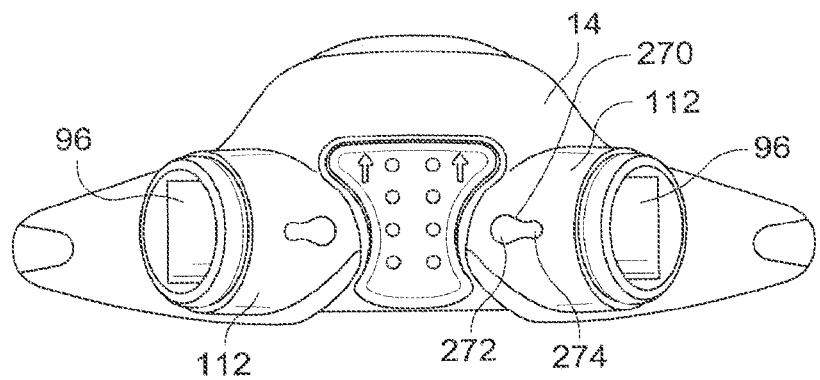
FIG. 100 schematically depicts a front view of a mask assembly illustrating an aperture for connection of a tether between a frame and a plug according to another sample embodiment of the technology.
Figure 101:
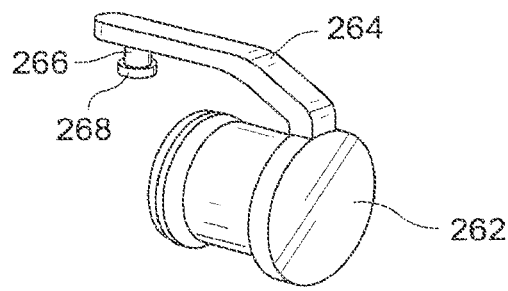
FIG. 101 schematically depicts a perspective view illustrating connection of a tether to a plug according to another sample embodiment of the technology.
Figure 102:
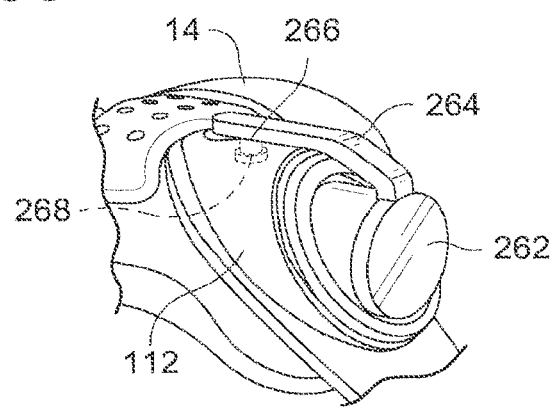
FIG. 102 schematically depicts a perspective view of a mask assembly illustrating connection of the tether and plug of FIG. 101 to a frame.

Referring to FIGS. 100-102, plug 262 may be connected to tether 264, with tether 264 adapted to connect to the frame 14. The tether 264 may include a connector 266, with a wide portion 268. The cylinder 112 of the frame 14 includes an aperture 270 having a wide portion 272 and a narrow portion 274. The wide portion 268 of the connector 266 is sized to fit into the wide portion 272 of the aperture 270. The wide portion 268 of the connector 266 may be pushed below a lower surface of the cylinder 112, and the connector 266 may be positioned so that the wide portion 268 is below the narrow portion 274 of the aperture 270, to retain the tether 264 to the cylinder 112 of the frame 14. The tether 264 may be stretchable to allow the connector 266 to stretch to reach the wide portion 272 of the aperture 270. Alternatively or in addition, the cushion 12 may be compressible or flexible to permit the plug 262 to move while connected to the cushion 12, such that connector 266 may travel from the narrow portion 274 to the wide portion 272 of the aperture 270.

Figure 103:
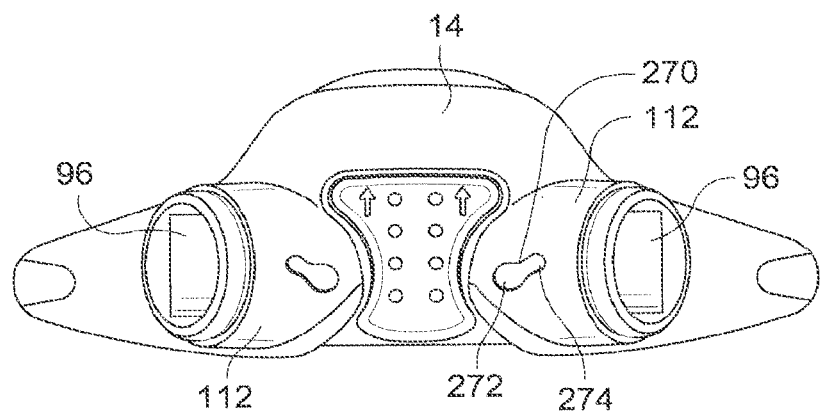
FIG. 103 schematically depicts a front view a front view of a mask assembly illustrating an aperture for connection of a tether between a frame and a plug according to another sample embodiment of the technology.

Referring to FIG. 103, an alternate configuration is illustrated, in which the aperture 270 includes a wide portion 272 and a narrow portion 274. The wide portion 272 may be offset to the side from the narrow portion 274 with respect to an axis of cylinder 96. The offset helps to retain the connector 266 in the narrow portion 274 of the aperture 270.

Figure 104:
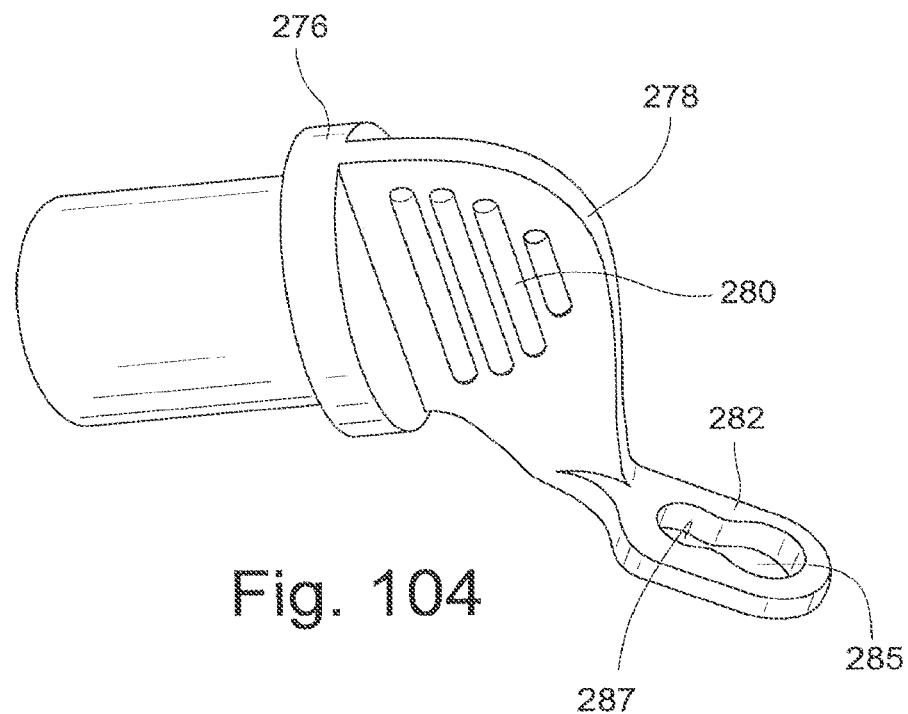
FIG. 104 schematically depicts a perspective view of a plug having a connector according to another sample embodiment of the technology.
Figure 105:
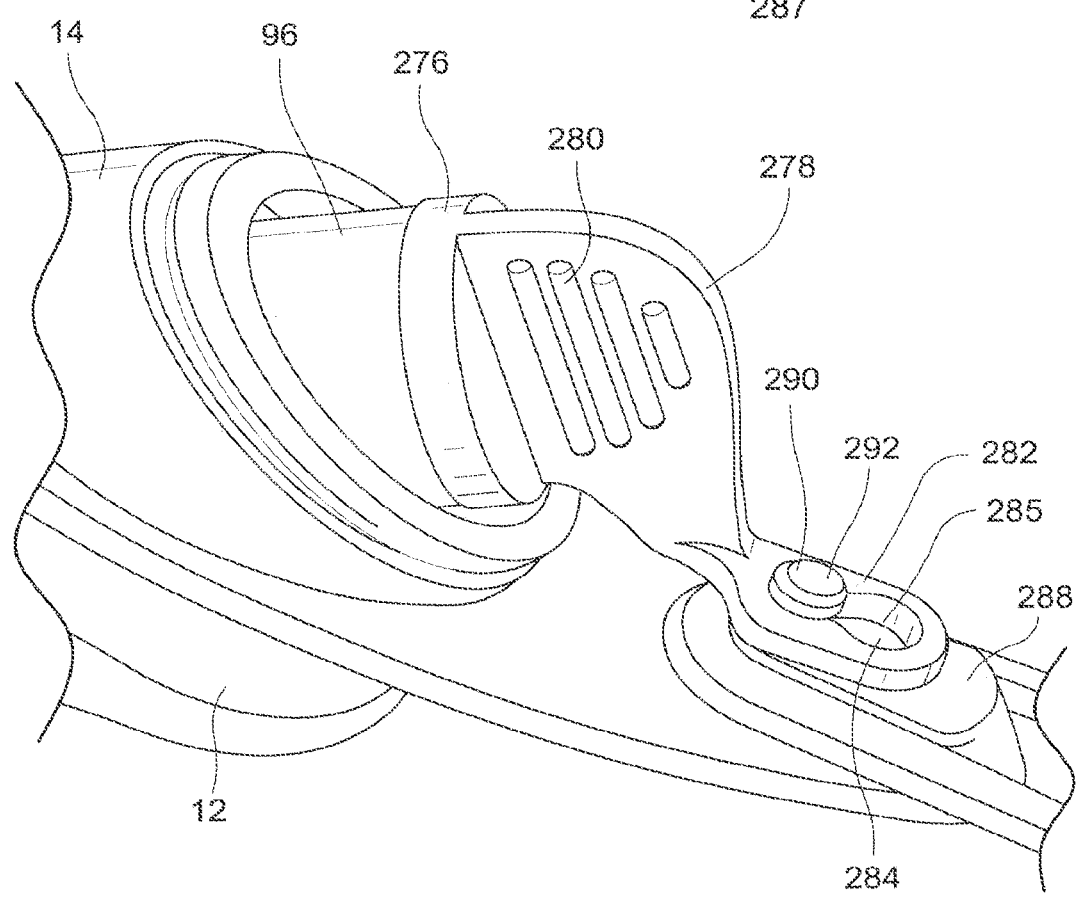
FIG. 105 schematically depicts a mask assembly having the plug and the connector of FIG. 104 connected to a frame.

Referring to FIGS. 104 and 105, plug 276 is adapted to fit within the cylinder 96 of cushion 12. The plug 276 includes a handle 278 and a connector 282 for connecting the plug to the frame 14 via post 290.

The handle 278 includes ribs 280 adapted to be gripped by a user. The connector 282 includes aperture 284 having a large aperture portion 285 and a small aperture portion 287.

The post 290 is located on the headgear connector 288. The post 290 includes a head 292 that has a diameter that is smaller than the diameter of the large aperture portion 285 but larger than the diameter of the small aperture portion 287, so that the head 292 of the post 290 can fit within the large aperture portion 285, but the head 292 of the post can be retained by the small aperture portion 287, as illustrated in FIG. 105.

Figure 107:
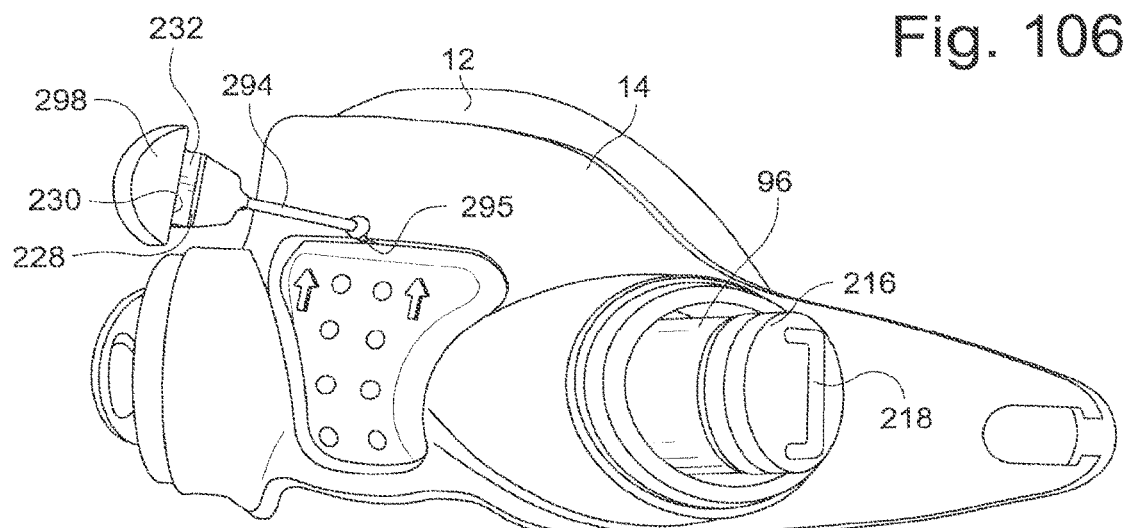
FIG. 107 schematically depicts a perspective view of a mask assembly having a post and a connector according to another sample embodiment of the technology.
Figure 108:
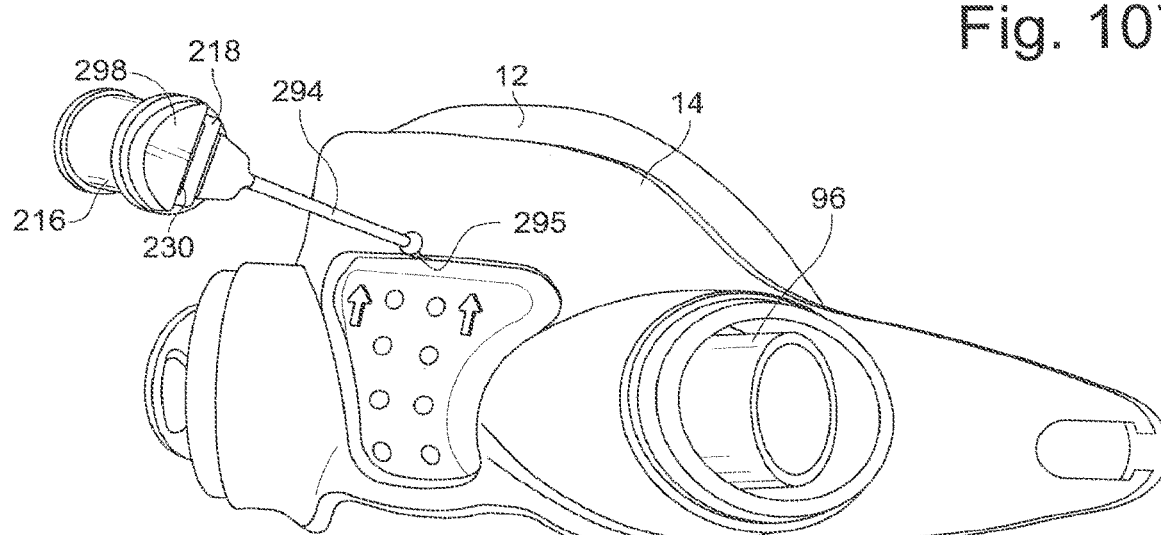
FIG. 108 schematically depicts a perspective view of the mask assembly of FIG. 107 with the plug retained onto the post according to another sample embodiment of the technology.

Referring to FIGS. 107 and 108, the post 294 has a connector 298 adapted to retain the plug 216. The connector 298 includes flanges 228 and 230 and recessed groove 232, adapted to receive the handle 218 of plug 216. Post 294 may constructed in one piece with cushion 12.

Figure 106:
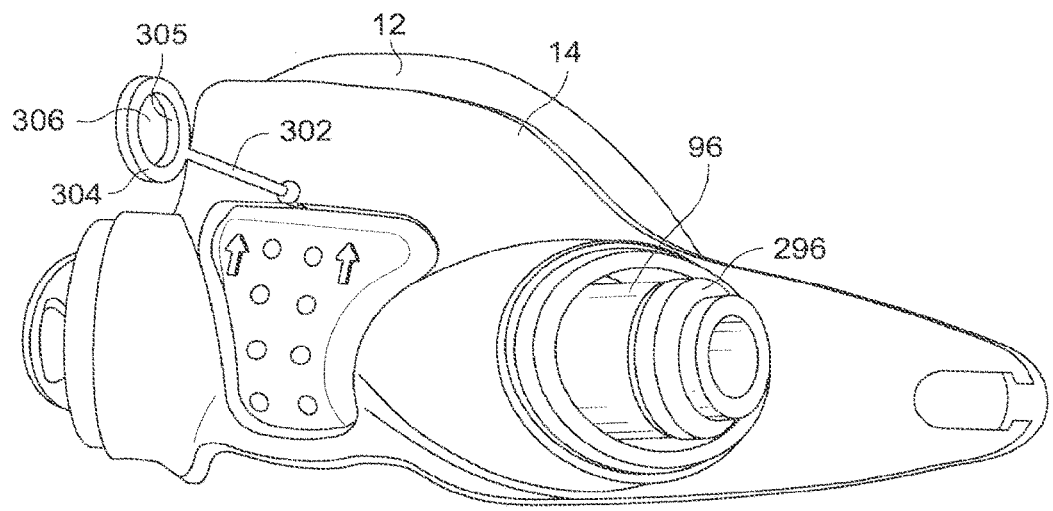
FIG. 106 schematically depicts a perspective view of a mask assembly having a post and a connector according to another sample embodiment of the technology.
Figure 109:
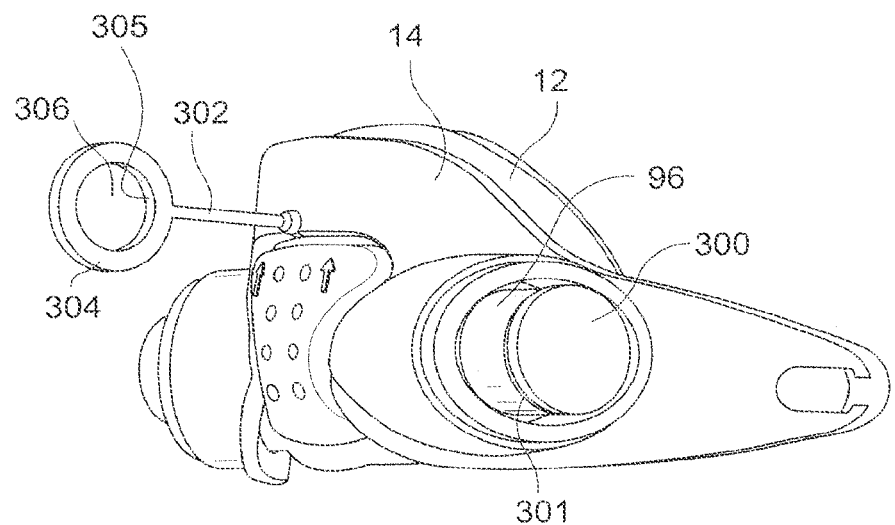
FIG. 109 schematically depicts a perspective view of a mask assembly having a post and a connector according to another sample embodiment of the technology.
Figure 110:
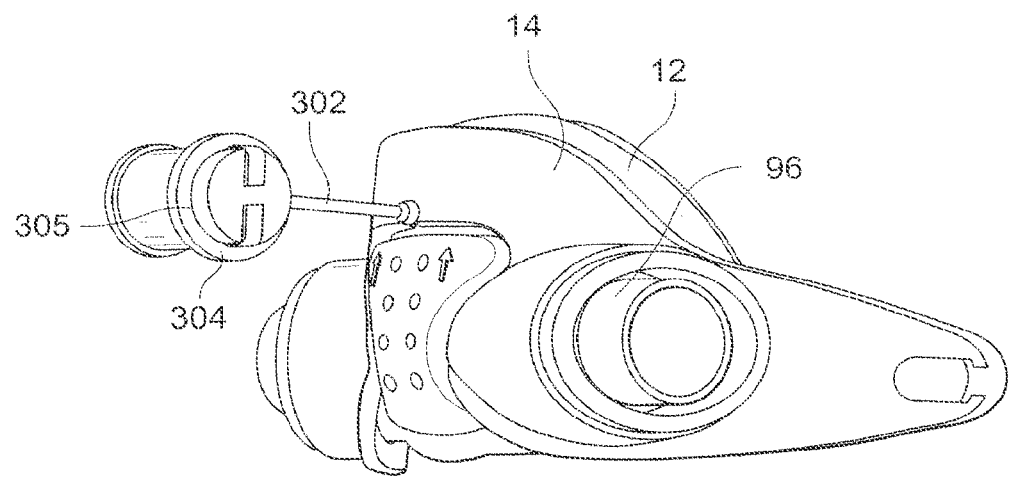
FIG. 110 schematically depicts a perspective view of the mask assembly of FIG. 109 with the plug retained onto the post according to another sample embodiment of the technology.

Referring to FIGS. 106, 109 and 110, plug 300 may be placed in cylinder 96 of cushion 12. When the plug 300 is removed from the cylinder 96, the plug 300 may be connected to connector 304, which is attached to frame 14 via post 302, as shown in FIG. 110. The connector 304 has an aperture 306, which is adapted to receive the plug 296, with the groove 301 of plug 300 adapted to receive an inner circumferential edge 305 of the connector 300.

1.3.9 Port

Figure 57:
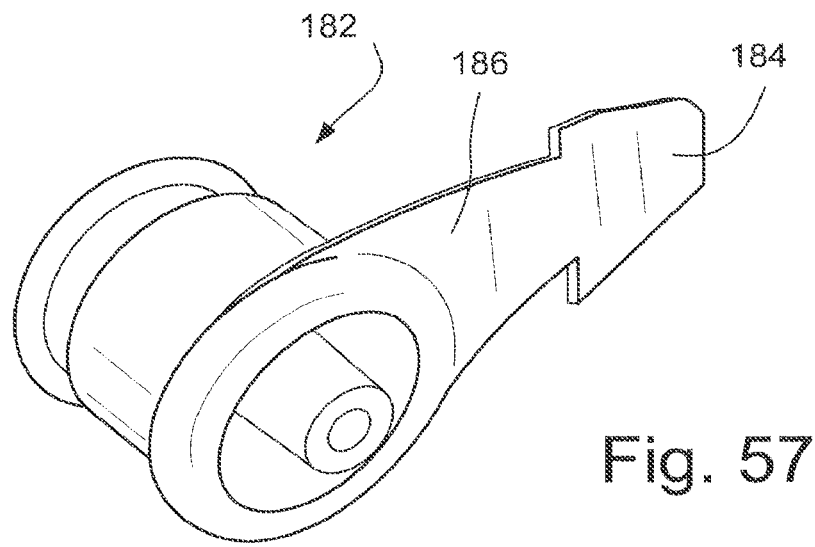
FIG. 57 schematically depicts a perspective view of a port with an extension member and barb according to another sample embodiment of the technology.
Figure 58:
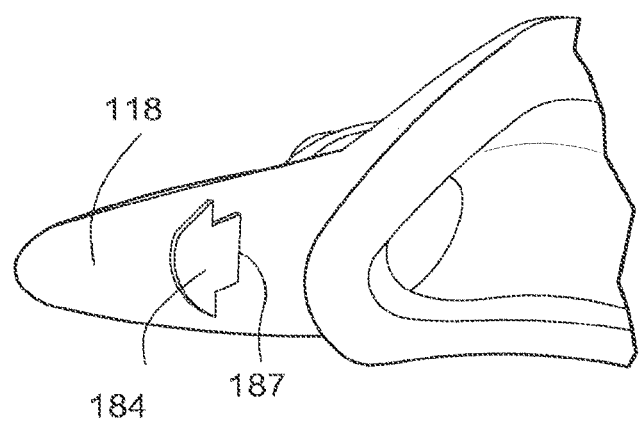
FIG. 58 schematically depicts a partial rear view of connection of the barb of FIG. 57 to a wing portion of a frame.
Figure 59:
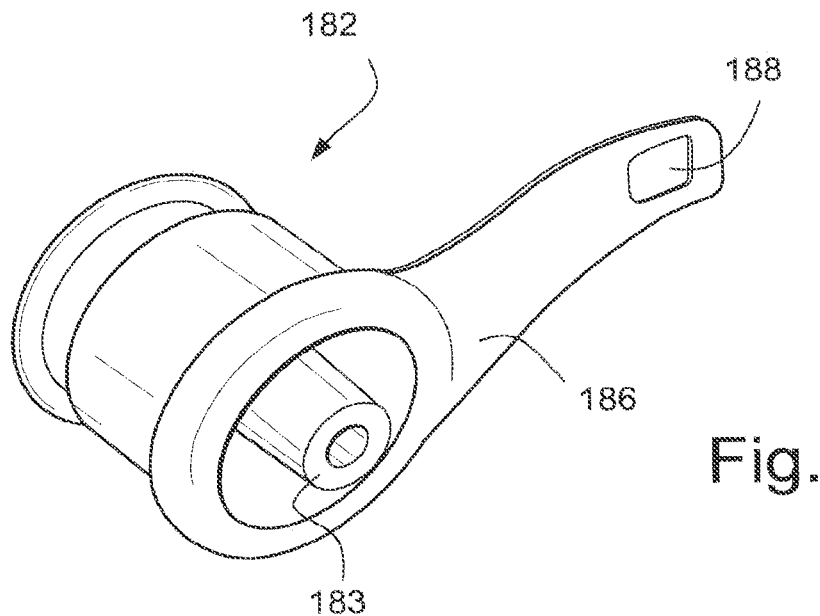
FIG. 59 schematically depicts a perspective view of a port with an extension member according to another sample embodiment of the technology.
Figure 60:
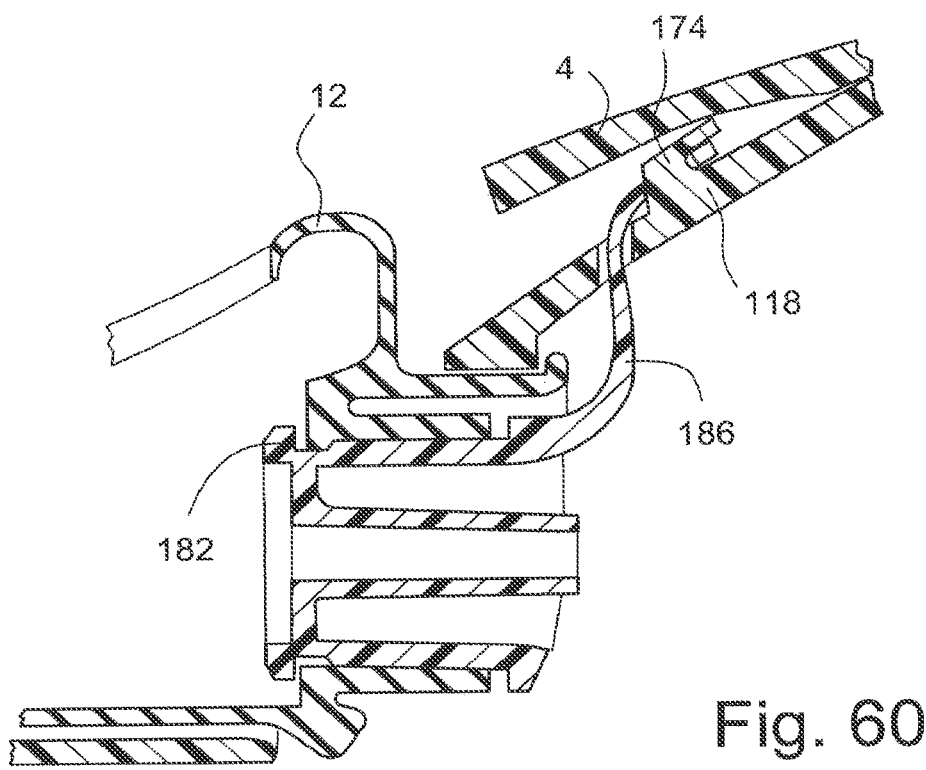
FIG. 60 schematically depicts a cross-sectional view of the port of FIG. 59 in a frame with the extension member connected to the wing portion of the frame.

Referring to FIGS. 55-68, a port 182 may be provided to one of the hollow cylindrical protrusions 88 of the cushion 12 to measure pressure or to administer breathable gas, for example oxygen. The port 182 may operate as a luer port. As shown in FIGS. 57 and 58, the port 182 may be connected to a wing portion 118 of the frame by an extension member 186 having a barb 184 received in a slot 187 in the wing portion 118. Alternatively, as shown in FIGS. 59 and 60, the port 182 may be connected to the wing portion 118 by a slot 188 in the extension member 186 that is received by a hook 174 on the rear side of the wing portion 118.

Figure 61:
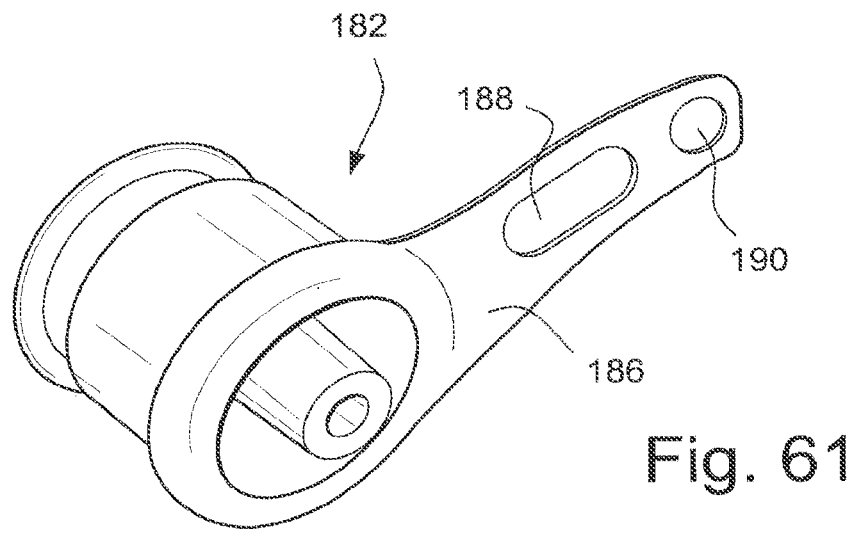
FIG. 61 schematically depicts a port with an extension member according to another sample embodiment of the technology.
Figure 62:
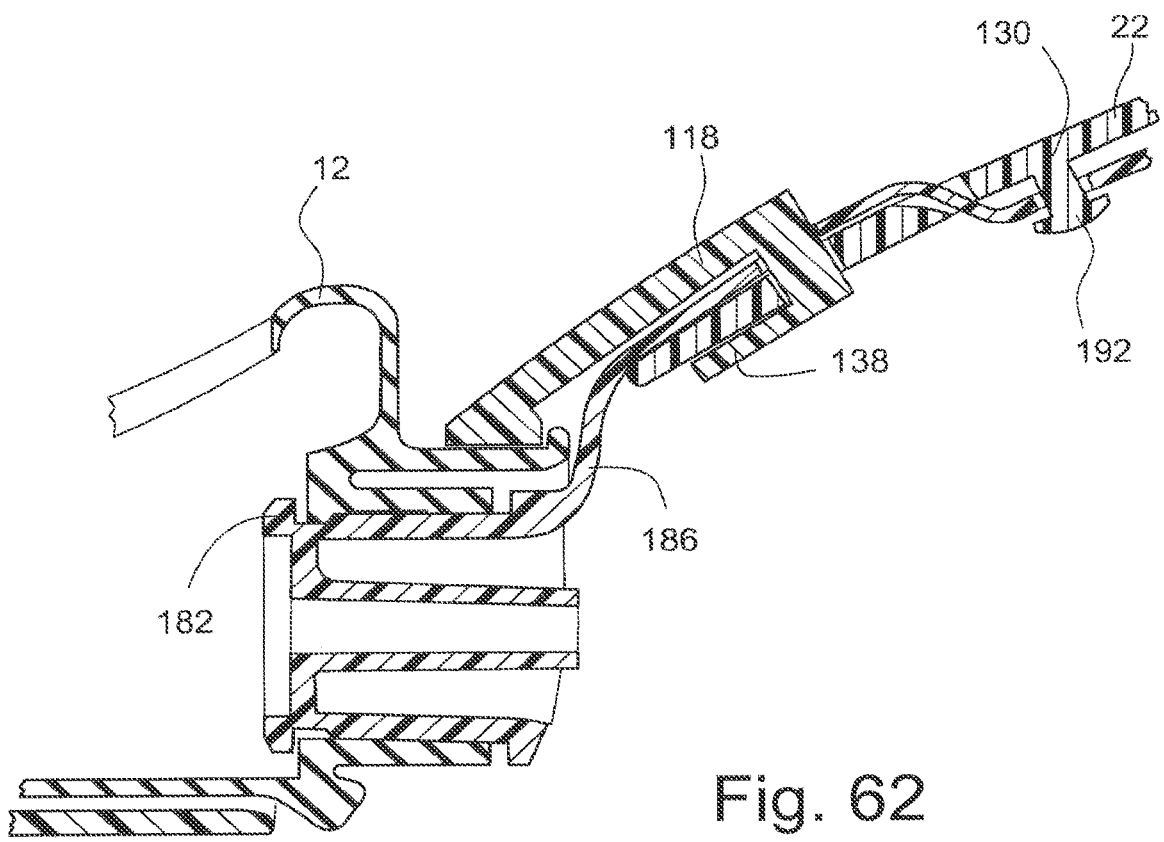
FIG. 62 schematically depicts a cross-sectional view of the port of FIG. 61 in a frame with the extension member connected to the wing portion of the frame and to a reinforcing structure of the headgear.

According to another sample embodiment shown in FIGS. 61 and 62, the extension member 186 includes a slot 188 and a hole 190. The slot 188 is received by a connector 138 of the frame 14 and the hole 190 is passed over a capped post 192 that is provided on the forward finger 130 of the reinforcing structure 22.

Figure 63:
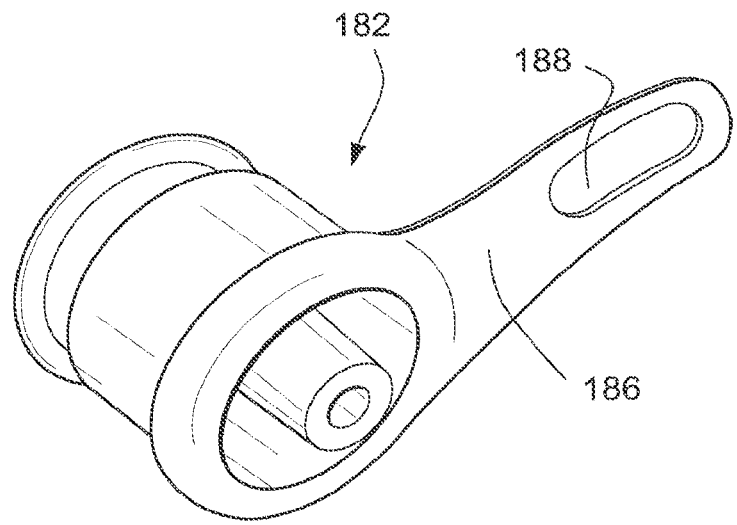
FIG. 63 schematically depicts a perspective view of a port with an extension member according to another sample embodiment of the technology.
Figure 64:
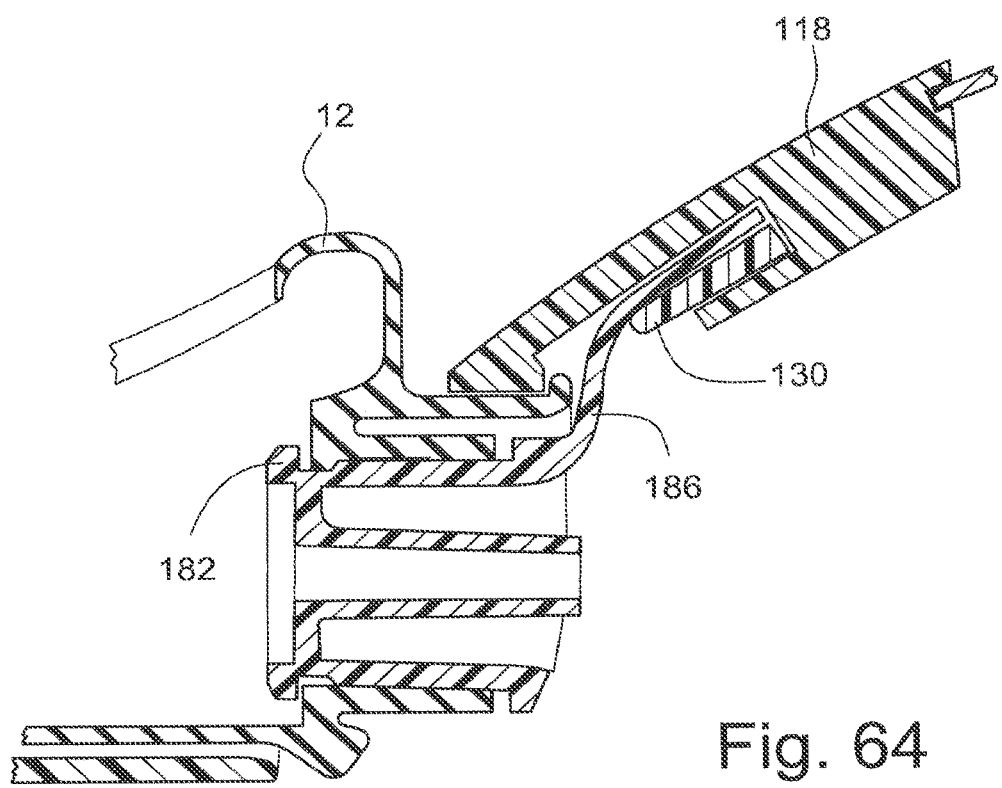
FIG. 64 schematically depicts a cross-sectional view of the port of FIG. 63 in a frame with the extension member connected to the wing portion of the frame.

As shown in FIGS. 63 and 64, the extension member 186 may include a slot 188 that secures the extension member 186 between the wing portion 118 of the frame 14 and the forward finger 130 of the reinforcing structure 22.

Figure 65:
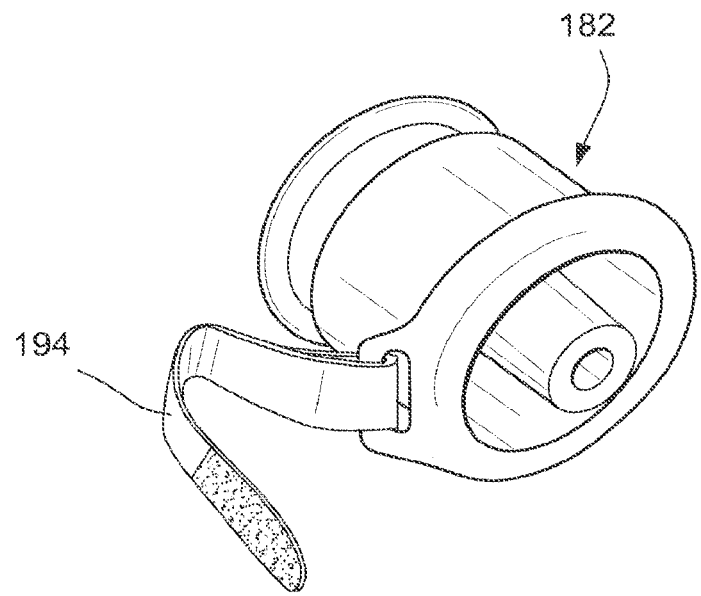
FIG. 65 schematically depicts a perspective view of a port with a tether according to another sample embodiment of the technology.

The port 182 may also be attached to the frame by a tether, for example a VELCRO® strap 194, as shown in FIG. 65.

Figure 66:
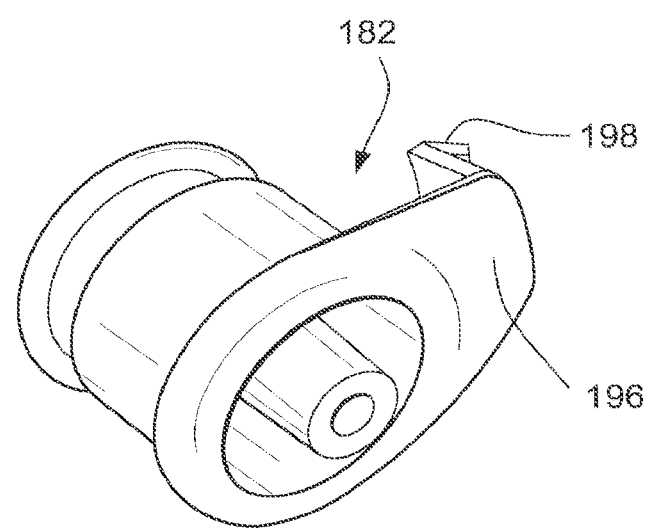
FIG. 66 schematically depicts a perspective view of a port with a snap arm according to another sample embodiment of the technology.
Figure 67:
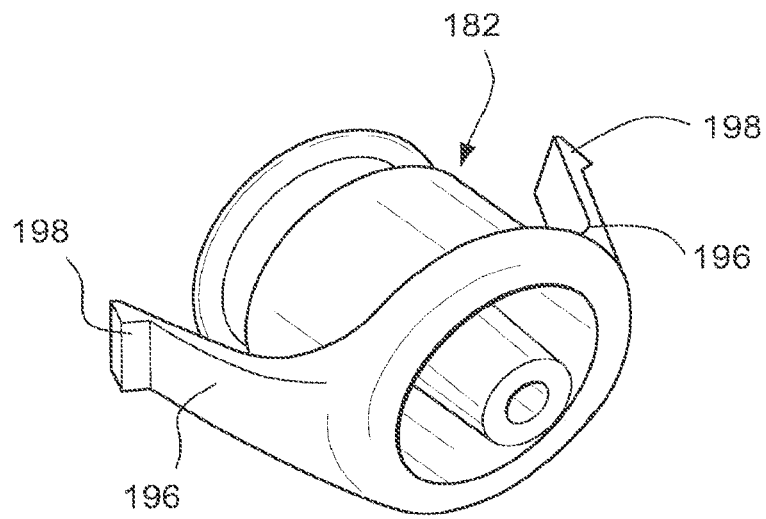
FIG. 67 schematically depicts a perspective view of a port with two snap arms according to another sample embodiment of the technology.
Figure 68:
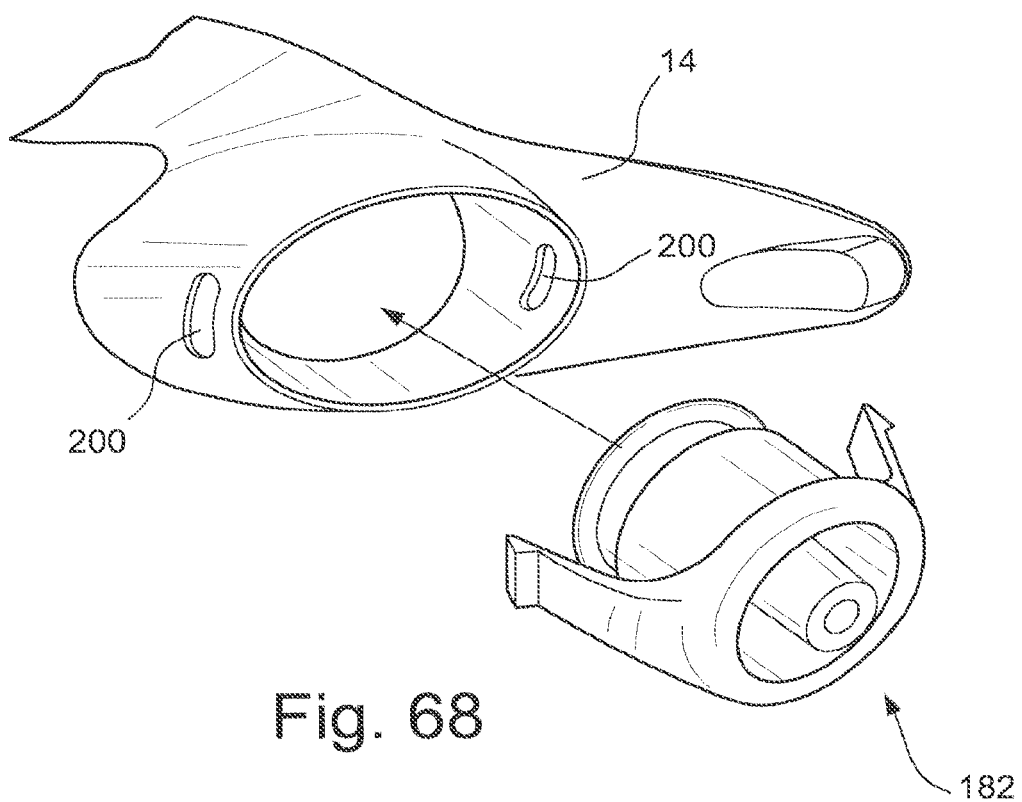
FIG. 68 schematically depicts a perspective view of the port of FIG. 67 and connection to a frame according to another sample embodiment of the technology.

FIGS. 66-68 depict a port 182 according to other sample embodiments. The port may include a snap arm 196 as shown in FIG. 66, or two snap arms 196 as shown in FIG. 67, that include a snap 198 at the end of each snap arm 196. The snap(s) 198 is (are) received in a slot(s) 200 as shown in FIG. 68 to secure the port 182 to the frame 14.

Figure 111:
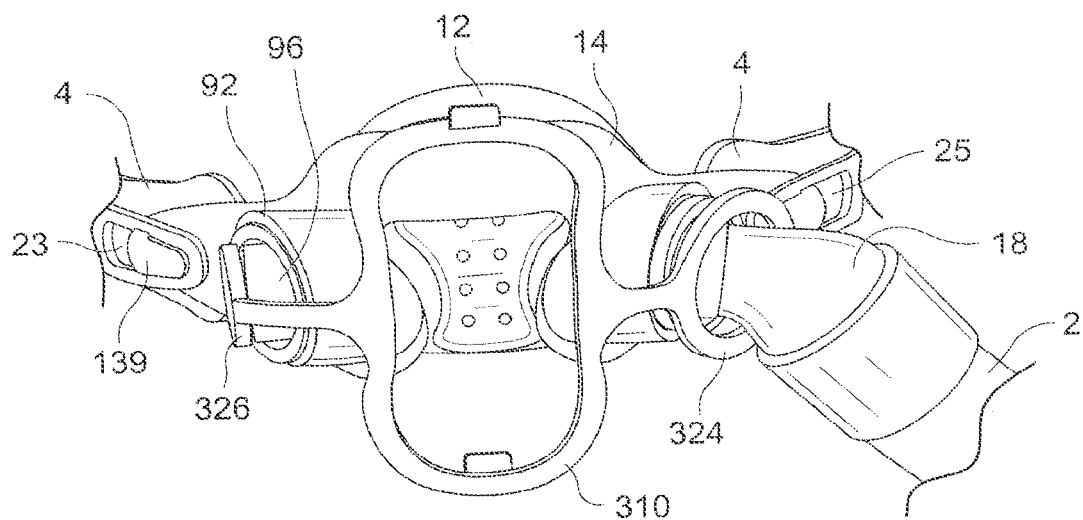
FIGS. 111 and 112 schematically depict a respiratory mask assembly according to another sample embodiment of the technology.
Figure 112:
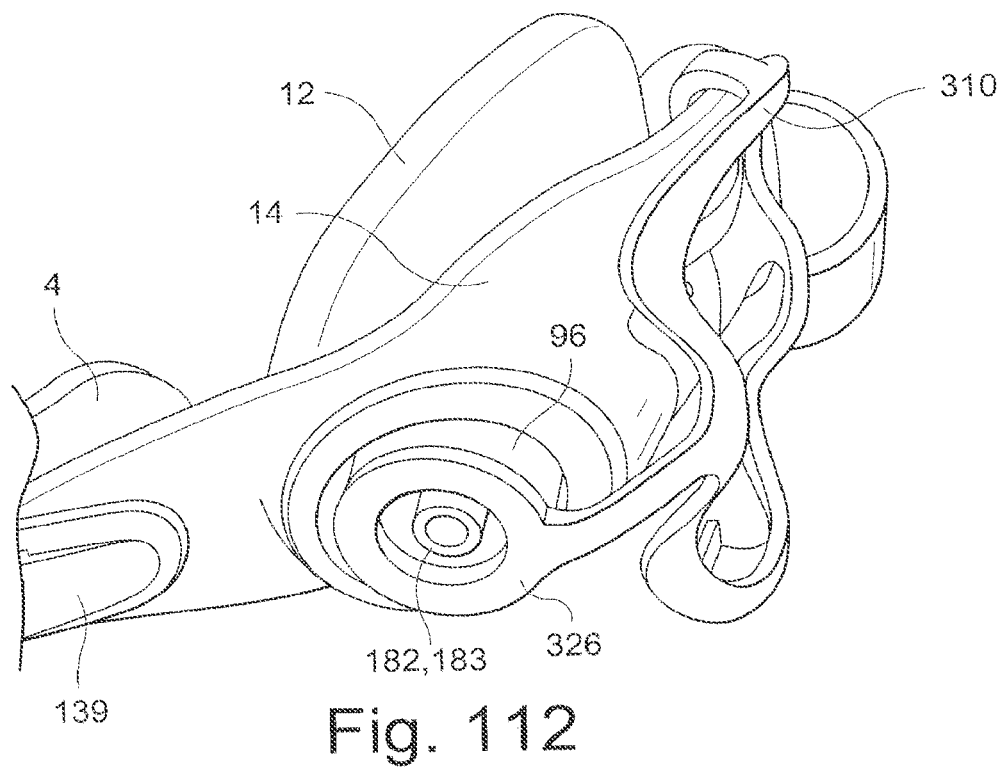

Referring to FIGS. 111 and 112, a pressure port 182 may be provided to the patient interface system. A pressure tube 312 (FIG. 113) may be attached to the outlet 183 of the pressure port 182 and to a pressure monitoring device so that pressure in the patient interface system can be determined. To prevent the pressure port 182 from being a chocking hazard for pediatric patients, the pressure port 182 may be connected to the patient interface system by a tether 310. As shown in FIG. 111, the tether 310 may include a loop portion 324 that is provided around the elbow 18 connected to the air delivery tube 2 to prevent the pressure port from being disconnected from the patient interface system. Although the looped portion 324 of the tether is shown as extending around the elbow 18, it should be appreciated that the looped portion 324 may extend around a headgear strap 4, the frame 14, or any other component of the patient interface system. The tether 310 has a snap 326 that snaps into the pressure port 182 around the outlet 183 of the pressure port 182 as shown in FIG. 112.

Figure 113:
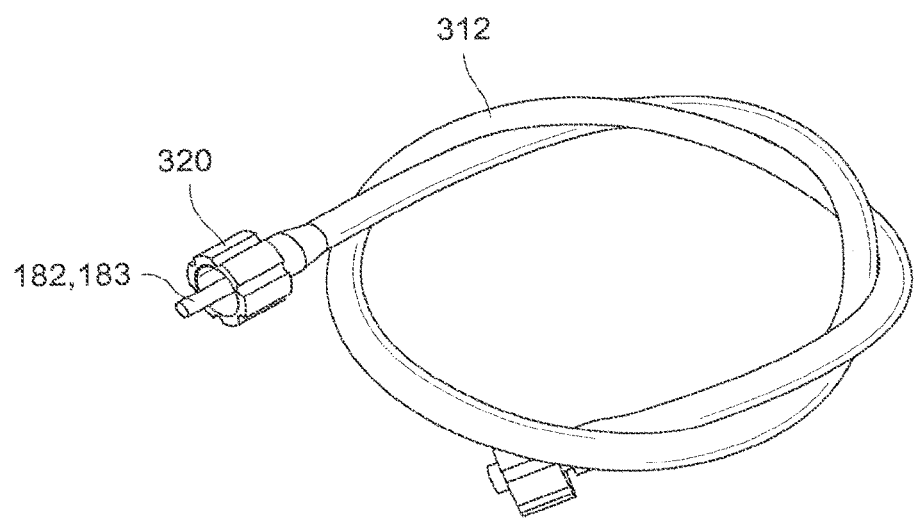
FIG. 113 schematically depicts a pressure port, a pressure tube, and an adaptor for the pressure port according to a sample embodiment of the invention.

Referring to FIG. 113, according to another sample embodiment, the pressure port 182 may be permanently affixed to the pressure tube 312 by an adaptor 320 to prevent the pressure port 182 from being a choking hazard for pediatric patients.

Figure 114:
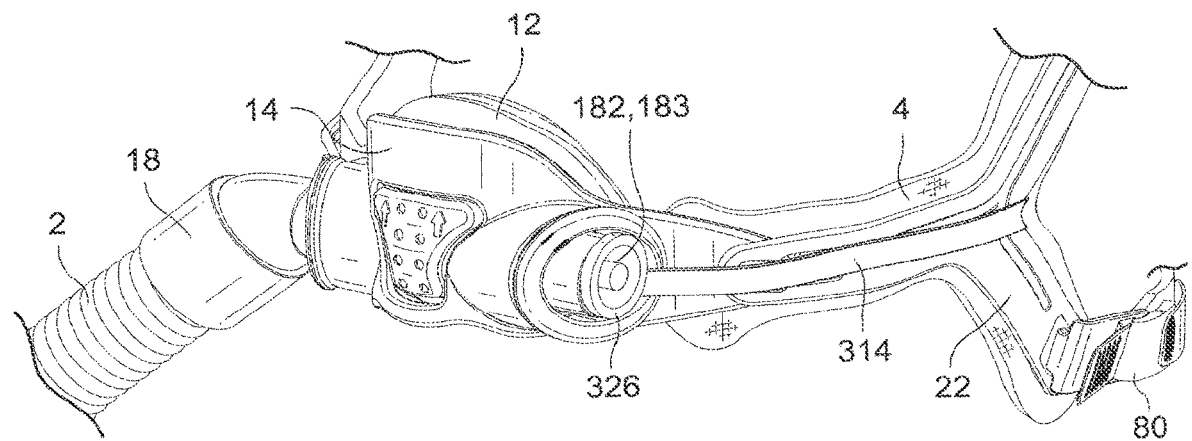
FIG. 114 schematically depicts a respiratory mask assembly including a pressure port and a tether according to another sample embodiment of the technology.
Figure 115:
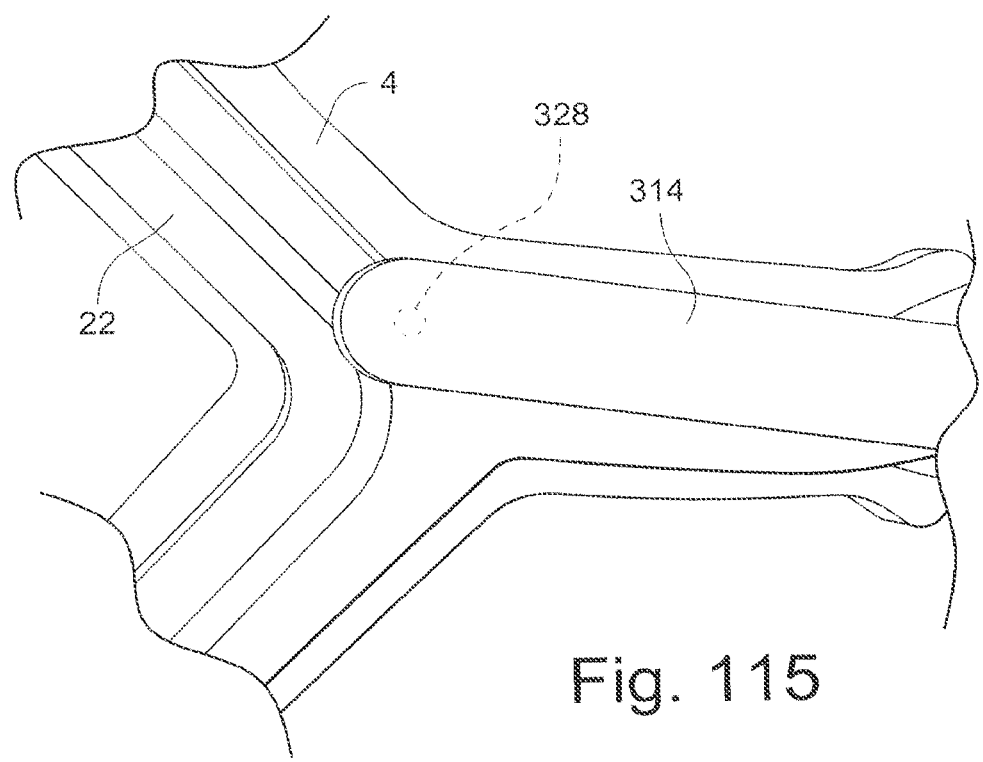
FIGS. 115 and 116 schematically depict a headgear including a tether for a pressure port, for example.
Figure 116:
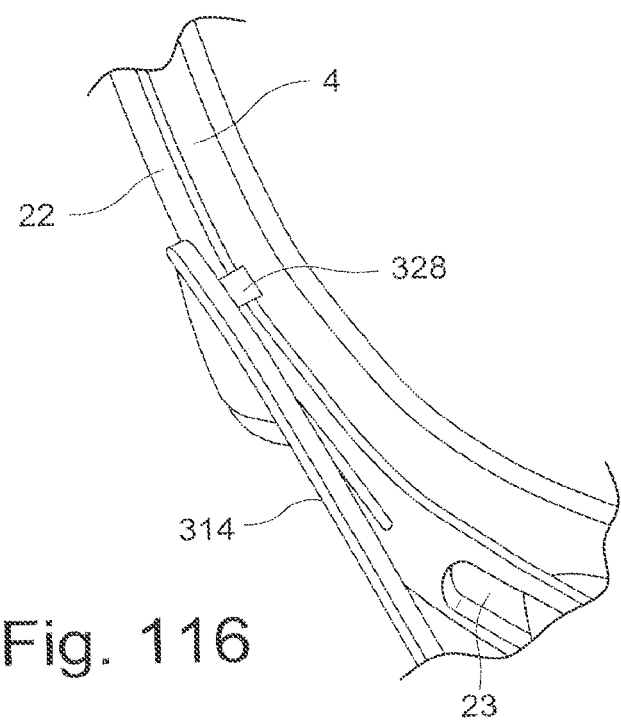

Referring to FIGS. 114-116, the pressure port 182 may be attached to a headgear strap, for example side strap 4, and/or a rigidizer 22 of the headgear 16. As shown in FIGS. 115 and 116, the pressure port 182 may be connected by a tether 314 that includes a post 328 that extends through the rigidizer 22 and the side strap 4. The pressure port 182, and the tether 314, may be provided on a side of the patient interface system on which the patient is not usually sleeping in order to improve comfort.

Figure 117:
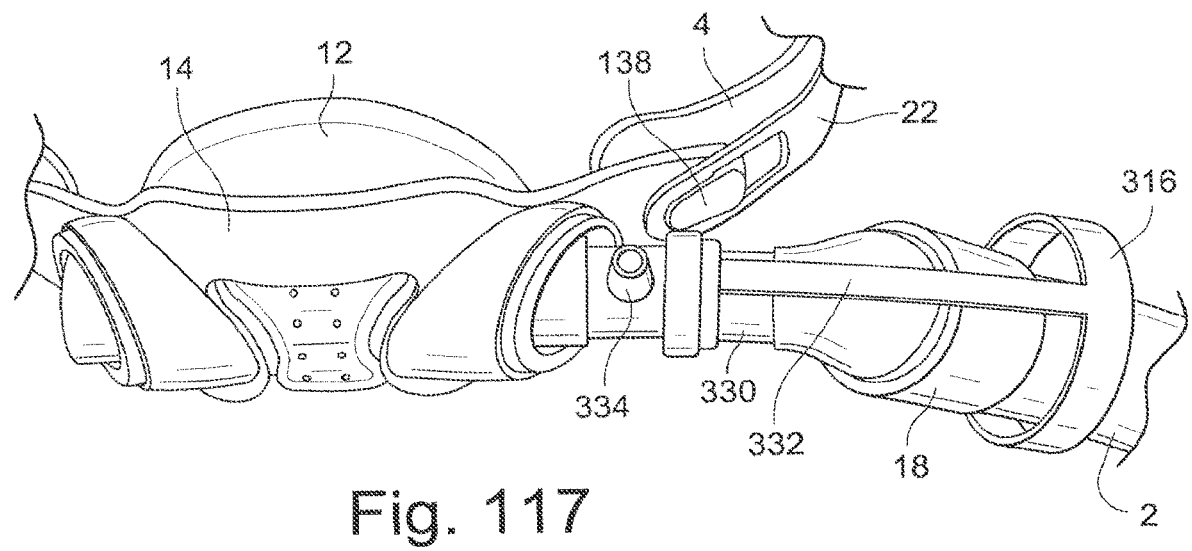
FIGS. 117 and 118 schematically depict a tether and a pressure port according to another sample embodiment of the technology.
Figure 118:
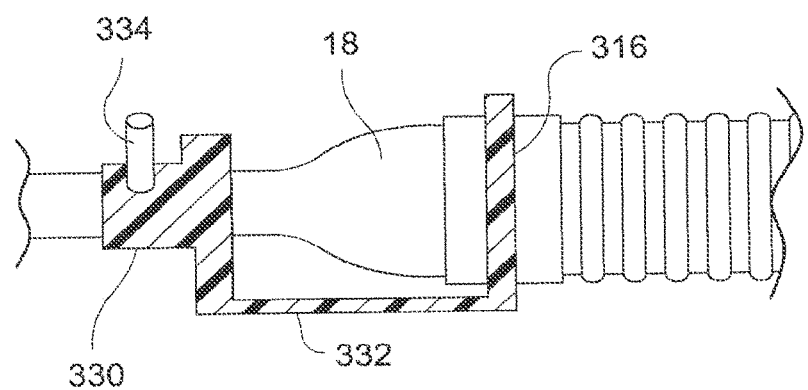
Figure 119:
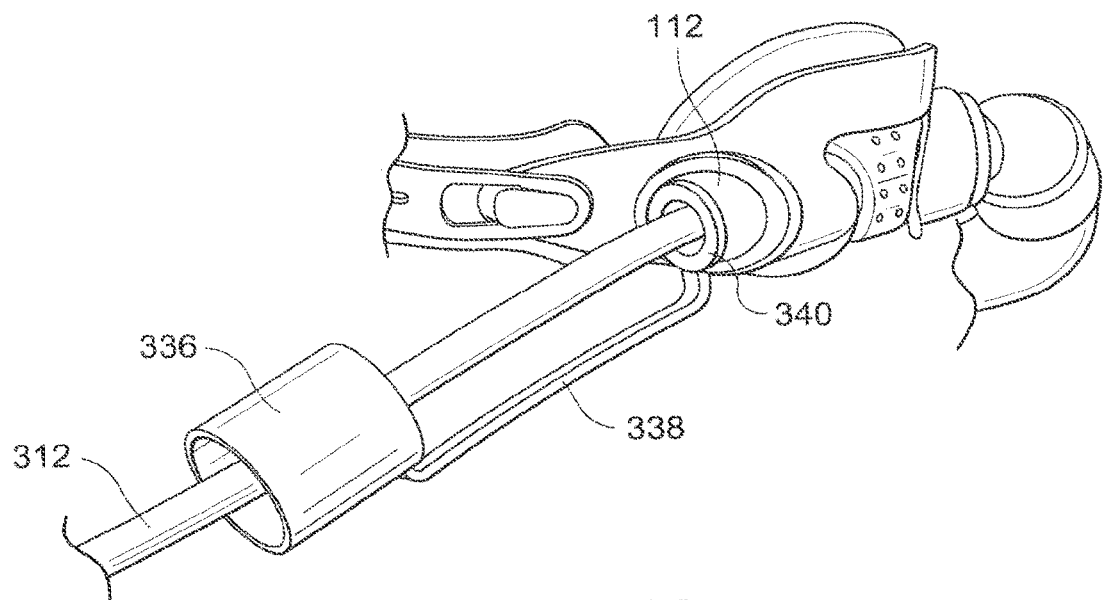
FIG. 119 schematically depicts a pressure port, a tether and a pressure tube according to another sample embodiment of the technology.

Referring to FIGS. 117 and 118, the pressure port may take the form of an adaptor 330 provided between the cushion and the elbow. The adaptor 330 has an outlet 334 for connection with a pressure measuring tube. The adaptor 330 may be retained to the patient interface system by a collar 316 that is coupled around another component, such as the elbow 18 of the air delivery tube 2. The collar 316 is connected to the adaptor 330 by a tether 332.

Referring to FIGS. 119-122, a pressure port 308 according to another sample embodiment may be secured to a pressure tube 312 by a collar 336 that is coupled around the pressure tube 312. The pressure port 308 is connected to the collar 336 by a tether 338 and a snap 340. The collar 336 may also function as a retainer for the tube 312, which may also be used as a means for delivering supplemental gas, such as oxygen.

Figure 120:
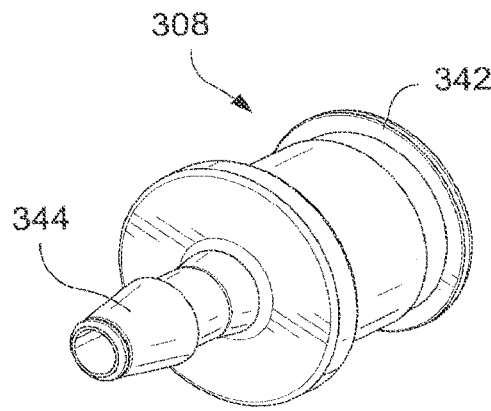
FIGS. 120-122 schematically depict a pressure port according to another sample embodiment of the technology.
Figure 121:
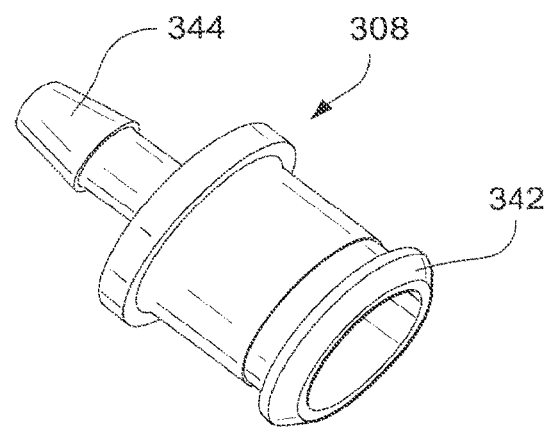
Figure 122:
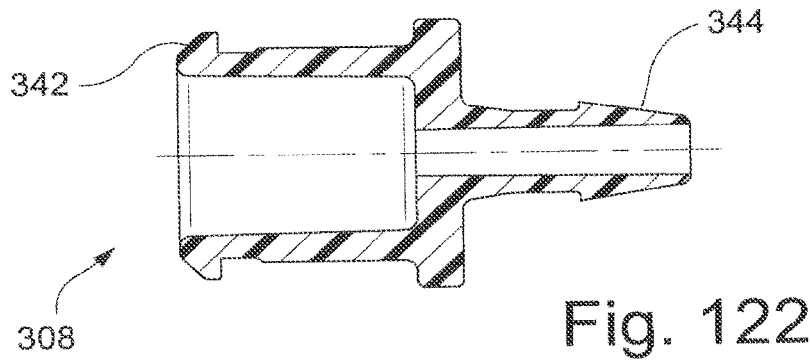

Referring to FIGS. 120-122, the pressure port 308 includes a first tapered end 342 configured for insertion into a cylinder of the cushion 12 of the patient interface system. A second end 344 of the pressure port 308 is configured to be connected to the pressure tube 312 for monitoring a pressure inside the patient interface system. As shown in FIG. 122, the second end 344 of the pressure port 308 has a tapered surface for insertion into the pressure tube 312. The tapered surface 344 may also be polished and free from flash to facilitate insertion and removal of the second end of the pressure port 308 into the pressure tube 312.

1.4 Elbow and Tube

Figure 11:
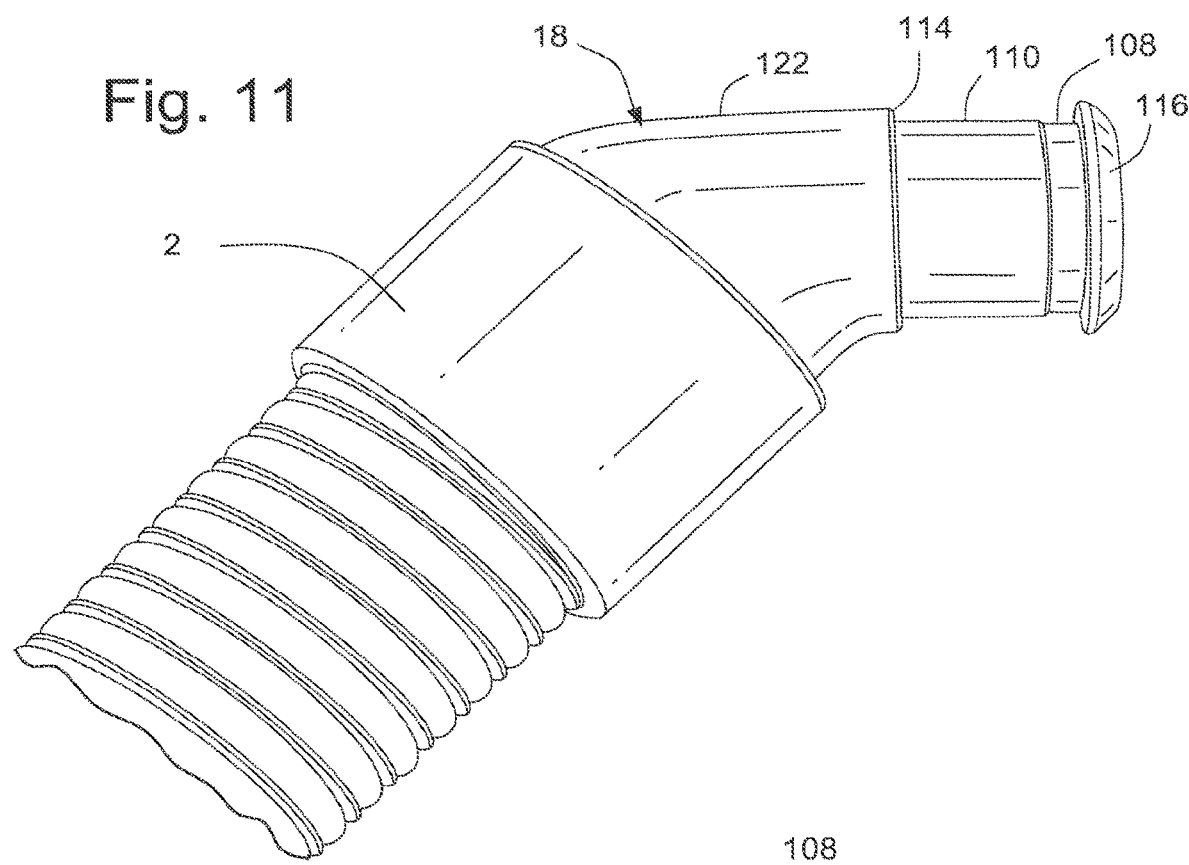
FIG. 11 schematically depicts a side view of an elbow and tube of the respiratory mask assembly of FIG. 1.
Figure 12:
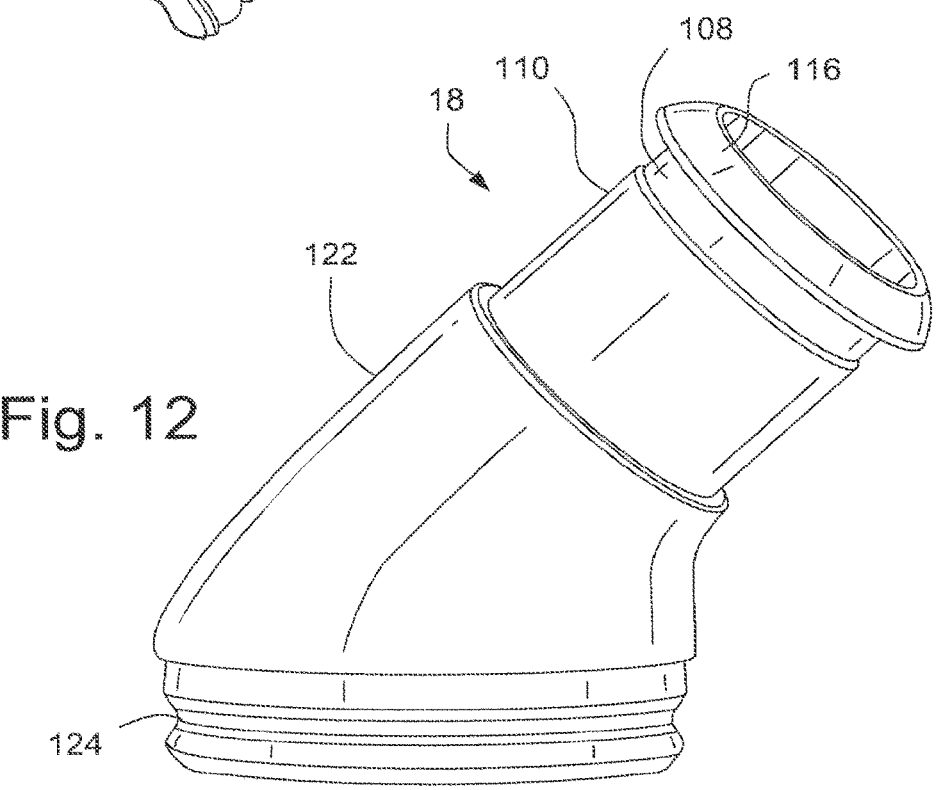
FIGS. 12 and 13 schematically depict the elbow of FIG. 11.
Figure 13:
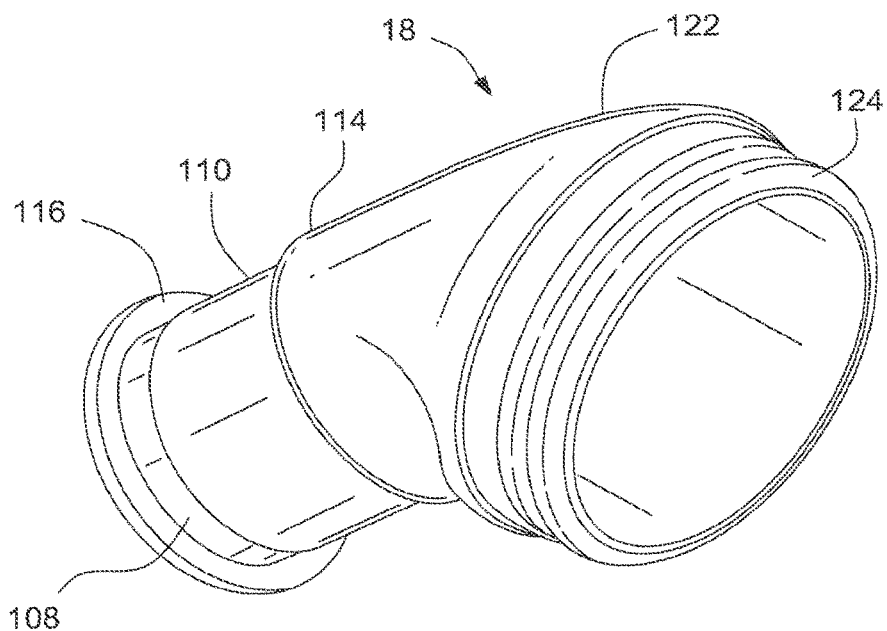

Referring to FIGS. 11-15, the elbow 18 provides a sealed but removable connection with the cushion 12. As shown in FIG. 11, the elbow 18 provides a sealed and permanent connection with the tube 2. The structure of the elbow 18 that fits within the cushion 12 may be identical to the corresponding structure of the plug 20, and like reference numerals are accordingly used. The elbow 18 includes a tube connection end 124 configured to connect the elbow 18 to the tube 2. The tube 2 may be a retractable tube as disclosed in, for example, U.S. Patent Application Publication 2009/0078259 A1, the entire contents of which are incorporated herein by reference. The tube 2 may have a length of about 2 m or less. The use of a retractable tube having a length of about 2 m or less reduces the impedance of the tube.

The elbow 18 includes a beveled flange 116 that is configured to aid insertion of the elbow 18 into the short, hollow cylindrical protrusion 88 of the cushion 12. As shown in FIG. 15, a circumferential edge 114 is provided between the outer sealing surface 110 of the elbow 18 and the outer surface 122 of the elbow 18. The inner cylinder 96 of the short, hollow cylindrical protrusion 88 of the cushion 12 is captured between the beveled flange 116 and the circumferential edge 114 to provide secure attachment of the elbow 18 to the cushion 12.

Figure 14:
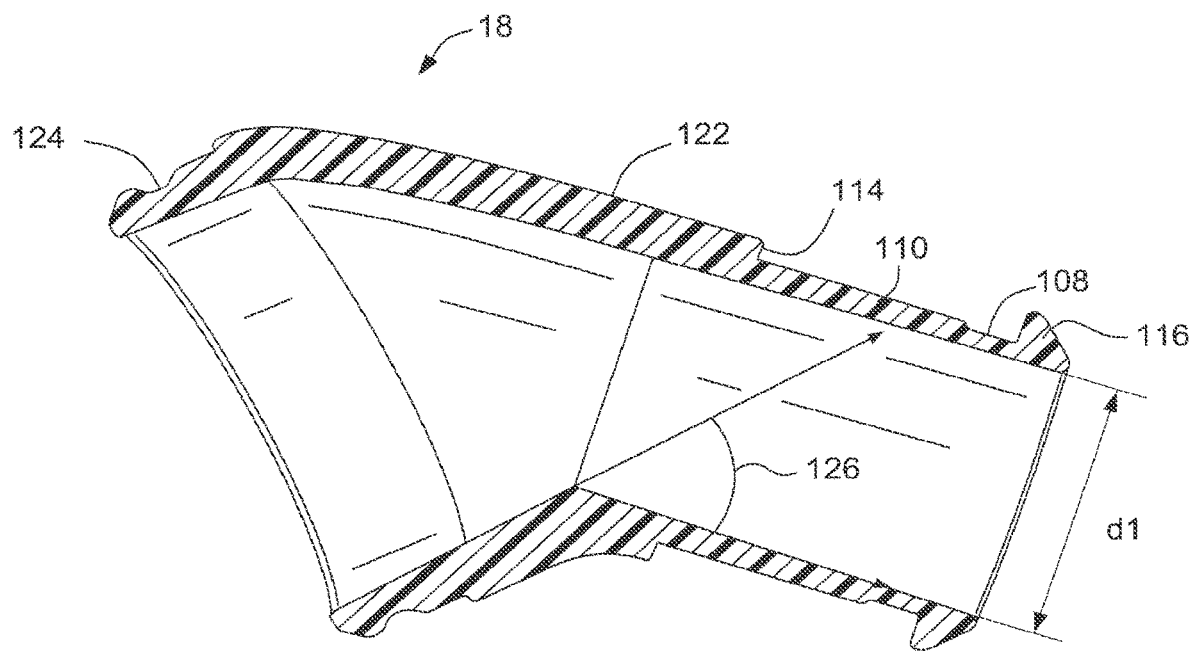
FIG. 14 schematically depicts a cross-sectional view of the elbow of FIGS. 11-13.

Referring to FIG. 14, the elbow may have a bend, or angle, 126 in the range of, for example, about 35° to 55°, for example about 39.5° to 49.5°. The elbow 18 may have an inner diameter d1 of, for example, about 7 to 10 mm, for example about 8.5 mm.

1.5 Alternate Embodiments

It should be appreciated that the mask or patient interface system may have other interfacing arrangements, e.g., over-the-nose interface, full-face, nasal prongs, pillows, or cannulae, or a combination of a mouth sealing structure in combination with nasal prongs, pillows, or cannulae.

The respiratory mask assembly may be configured so that no hard material is exposed. For example, the support structure and or the rigid members may be covered in a material that is softer than the material used to form the support structure and/or the rigid members. In the sample embodiments discussed above in which the cushion and the frame, or support structure, are formed as a single piece, e.g. by co-molding, the support structure may be formed to be more rigid than the cushion, but less rigid than currently used mask frames or shells made of rigid plastic material.

While the technology has been described in connection with what are presently considered to be the most practical and desirable embodiments, it is to be understood that the technology is not to be limited to the disclosed embodiments, but on the contrary, is intended to cover various modifications and equivalent arrangements included within the spirit and scope of the invention(s). Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the technology has particular application to patients who suffer from OSA, it is to be appreciated that patients who suffer from other illnesses (e.g., congestive heart failure, diabetes, morbid obesity, stroke, bariatric surgery, congenital disease in children etc.) can derive benefit from the above teachings. Moreover, the above teachings have applicability with patients and non-patients alike in non-medical applications.

What is claimed is:

1. A patient interface configured to deliver pressurized breathable gas to a patient's airways, the patient interface comprising:
    a flexible cushion arranged to interface with and deliver air to a nose of the patient in use, the flexible cushion comprising a pair of air inlets on opposite lateral sides of a central portion of the flexible cushion, each air inlet having a circumferential flange positioned around an outer surface of said air inlet to form a circumferential channel with the central portion of the flexible cushion;
    a frame that is more rigid than the flexible cushion and is configured to support the flexible cushion, the frame comprising a pair of lateral portions, each lateral portion comprising a receptacle that receives a respective one of the air inlets and each lateral portion of the frame being received in a respective one of the circumferential channels around the air inlets; and
    a removable pressure port connectable to a pressure monitor configured to determine the pressure of the breathable gas,
    wherein each air inlet is configured to be selectively coupled to either the removable pressure port or an air delivery tube, and
    wherein the removable pressure port is configured so that when the removable pressure port is coupled to a respective one of the air inlets, the respective air inlet is prevented from receiving pressurized breathable gas from the air delivery tube.

2. The patient interface of claim 1, wherein each air inlet is self-sealing and comprises a sealing valve that is configured to be opened by the insertion of the air delivery tube into the air inlet.

3. The patient interface of claim 2 wherein the sealing valve is integrally formed with the flexible cushion.

4. The patient interface of claim 2, wherein the sealing valve comprises a plurality of flaps.

5. The patient interface of claim 4, wherein the flaps are hinged.

6. The patient interface of claim 2, wherein the sealing valve is biased to the closed position.

7. The patient interface of claim 1, wherein the flexible cushion and the frame are separable from each other.

8. A patient interface assembly configured to pressurized breathable gas to a patient's airways, the patient interface assembly comprising:
    the patient interface of claim 1; and
    the air delivery tube.

9. A patient interface configured to deliver pressurized breathable gas to a patient's airways, the patient interface comprising:
    a flexible cushion arranged to interface with and deliver air to a nose of the patient in use, the flexible cushion comprising a pair of air inlets on opposite lateral sides of a central portion the flexible cushion, each air inlet having a circumferential flange positioned around an outer surface of said air inlet to form a circumferential channel with the central portion of the flexible cushion;
    a frame that is more rigid than the flexible cushion and is configured to support the flexible cushion, the frame comprising a pair of lateral portions, each lateral portion comprising a receptacle that receives a respective one of the air inlets and each lateral portion of the frame being received in a respective one of the circumferential channels around the air inlets, the frame further comprising an upper bridge and a lower bridge extending between the air inlets, the lower bridge being positioned to resist movement of the air inlets toward each other; and
    a removable pressure port that is connectable to a pressure monitor configured to determine the pressure of the breathable gas,
    wherein each air inlet is configured to be selectively coupled to either the removable pressure port or an air delivery tube so that one of the air inlets is coupled to the removable pressure port while the other air inlet is coupled to the air delivery tube.

10. The patient interface of claim 9, wherein the removable pressure port is a luer port.

11. The patient interface of claim 9, wherein the removable pressure port is configured to receive a supply of breathable gas from a source outside of the patient interface.

12. The patient interface of claim 9, wherein the removable pressure port is attached to the frame by way of a tether.

13. The patient interface of claim 9, further comprising a pressure tube attached to the removable pressure port, the pressure tube being attachable to the pressure monitor.

14. The patient interface of claim 13, wherein the pressure tube is permanently attached to the removable pressure port.

15. The patient interface of claim 9, further comprising headgear attachable to the frame and configured to support the flexible cushion and the frame on the patient's head.

16. The patient interface of claim 15, wherein the removable pressure port is attached to the headgear by way of a tether.

17. The patient interface of claim 15, wherein the headgear comprises a rigidizer.

18. The patient interface of claim 9, wherein the flexible cushion and the frame are separable from each other.

19. A patient interface assembly configured to pressurized breathable gas to a patient's airways, the patient interface assembly comprising:
the patient interface of claim 9; and
the air delivery tube.

20. The patient interface of claim 19, wherein the air delivery tube and the removable pressure port are configured to be interchangeably coupled to each air inlet.

21. The patient interface of claim 9, wherein the pair of air inlets are self-sealing with each air inlet comprising a sealing valve configured to automatically close the air inlet when the interior of the air inlet is empty.

22. The patient interface of claim 9, wherein the flexible cushion is configured to be simultaneously coupled to the removable pressure port and the air delivery tube at different locations on the flexible cushion.

23. The patient interface of claim 22, wherein the different locations on the flexible cushion are on opposite lateral sides of the flexible cushion.

24. The patient interface of claim 9, wherein the upper and lower bridges are positioned so that there is a gap between the upper and lower bridges and between the lateral portions of the frame, wherein the flexible cushion comprises a central thickened portion at which an elastomeric wall thickness of the flexible cushion is greatest, and wherein the central thickened portion of the flexible cushion is received by and extends through the gap.

25. The patient interface of claim 24, wherein a rim of the gap in the frame has the same shape as the perimeter of the central thickened portion of the flexible cushion.

26. The patient interface of claim 24, wherein the central thickened portion of the flexible cushion comprises an array of vent openings.

27. The patient interface of claim 9, wherein a width of the upper bridge is greater than a width of the lower bridge.

* * * * *